US012590126B2

(12) United States Patent
Chahwan et al.

(10) Patent No.: US 12,590,126 B2
(45) Date of Patent: *Mar. 31, 2026

(54) COMPOUNDS FOR SELECTIVE DISRUPTION OF PROTEIN-PROTEIN INTERACTIONS

(71) Applicant: SyntheX, Inc., San Francisco, CA (US)

(72) Inventors: Charly Chahwan, San Francisco, CA (US); Maria Soloveychik, San Francisco, CA (US)

(73) Assignee: SyntheX, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/455,139

(22) Filed: Aug. 24, 2023

(65) Prior Publication Data

US 2024/0018188 A1 Jan. 18, 2024

Related U.S. Application Data

(63) Continuation of application No. 16/876,809, filed on May 18, 2020, now Pat. No. 11,780,881, which is a continuation of application No. PCT/US2018/062351, filed on Nov. 21, 2018.

(60) Provisional application No. 62/590,056, filed on Nov. 22, 2017.

(51) Int. Cl.
| *C07K 7/08* | (2006.01) |
| *A61K 9/00* | (2006.01) |
| *A61K 38/00* | (2006.01) |

(52) U.S. Cl.
CPC .............. *C07K 7/08* (2013.01); *A61K 9/0019* (2013.01); *A61K 38/00* (2013.01); *C07K 2319/10* (2013.01)

(58) Field of Classification Search
None
See application file for complete search history.

(56) References Cited

U.S. PATENT DOCUMENTS

| 5,925,523 | A | 7/1999 | Dove et al. |
| 5,955,280 | A | 9/1999 | Vidal et al. |
| 5,965,368 | A | 10/1999 | Vidal et al. |
| 6,037,125 | A | 3/2000 | Hasty |
| 6,057,104 | A | 5/2000 | Hasty |
| 6,114,111 | A | 9/2000 | Luo et al. |
| 6,200,759 | B1 | 3/2001 | Dove et al. |
| 6,303,302 | B1 | 10/2001 | Rupp et al. |
| 6,316,223 | B1 | 11/2001 | Payan et al. |
| 6,332,897 | B1 | 12/2001 | Weiner et al. |
| 6,500,636 | B1 | 12/2002 | Hecht et al. |
| 6,599,705 | B2 | 7/2003 | Rupp et al. |
| 6,610,473 | B1 | 8/2003 | Butz et al. |
| 6,610,495 | B1 | 8/2003 | Watt et al. |
| 6,790,607 | B1 | 9/2004 | Edwards et al. |
| 7,033,768 | B2 | 4/2006 | Vidal et al. |
| 7,105,341 | B2 | 9/2006 | Kinsella |
| 7,208,571 | B2 | 4/2007 | Kinsella |
| 7,252,952 | B2 | 8/2007 | Lorenz et al. |
| 7,378,248 | B2 | 5/2008 | Lorens et al. |
| 7,541,446 | B2 | 6/2009 | Hillen et al. |
| 7,566,765 | B2 | 7/2009 | Kinsella |
| 7,601,533 | B2 | 10/2009 | Vidal et al. |
| 7,892,823 | B2 | 2/2011 | Ezekiel |
| 8,597,949 | B2 | 12/2013 | Connell et al. |
| 8,759,089 | B2 | 6/2014 | Ezekiel |
| 9,040,462 | B2 | 5/2015 | Lorens et al. |
| 9,150,897 | B2 | 10/2015 | Kowalczykowski et al. |
| 9,198,914 | B2 | 12/2015 | Connell et al. |
| 9,249,410 | B2 | 2/2016 | Hill et al. |
| 9,273,100 | B2 | 3/2016 | Hallen-Adams et al. |
| 9,408,816 | B2 | 8/2016 | Adimoolam et al. |
| 9,518,097 | B2 | 12/2016 | Hallen et al. |
| 10,188,691 | B2 | 1/2019 | Chahwan et al. |
| 11,780,881 | B2 | 10/2023 | Chahwan et al. |
| 11,840,743 | B2 | 12/2023 | Soloveychik et al. |
| 12,214,008 | B2 | 2/2025 | Chahwan et al. |
| 2002/0086840 | A1 | 7/2002 | Zarling et al. |
| 2002/0197627 | A1 | 12/2002 | Vidal et al. |
| 2003/0068612 | A1 | 4/2003 | Vidal et al. |
| 2003/0211495 | A1 | 11/2003 | Hopkins et al. |
| 2003/0229004 | A1 | 12/2003 | Zarling et al. |
| 2003/0235857 | A1 | 12/2003 | Rupp et al. |
| 2004/0180325 | A1 | 9/2004 | Edwards et al. |
| 2005/0053913 | A1 | 3/2005 | Vidal et al. |
| 2006/0003391 | A1 | 1/2006 | Ring et al. |

(Continued)

FOREIGN PATENT DOCUMENTS

| AU | 716893 | B2 | 3/2000 |
| AU | 735887 | B2 | 7/2001 |

(Continued)

OTHER PUBLICATIONS

Adamovich et al. F-Box Protein-Mediated Resistance to PARP Inhibitor Therapy. Mol Cell. Jan. 17, 2019;73(2):195-196. doi: 10.1016/j.molcel.2018.12.019.

(Continued)

*Primary Examiner* — Lianko G Garyu

*Assistant Examiner* — Tara L Martinez

(74) *Attorney, Agent, or Firm* — Wilson Sonsini Goodrich & Rosati

(57) ABSTRACT

The present disclosure provides methods to treat conditions, including cancer, using compounds that can target resistant cancer cells. The compounds can be used to sensitize resistant cancer cells or decrease the proliferation of cells. The compounds can target proteins in the DNA damage repair pathway leading to a decrease in DNA damage repair and cell death.

4 Claims, 14 Drawing Sheets

Specification includes a Sequence Listing.

(56) References Cited

U.S. PATENT DOCUMENTS

| | | |
|---|---|---|
| 2006/0116316 A1 | 6/2006 | Kinsella et al. |
| 2007/0105140 A1 | 5/2007 | Lorens et al. |
| 2007/0287677 A1 | 12/2007 | Kaneda |
| 2015/0306069 A1 | 10/2015 | Connell et al. |
| 2016/0281075 A1 | 9/2016 | Hallen-Adams et al. |
| 2017/0014360 A1 | 1/2017 | Connell et al. |
| 2017/0022494 A1 | 1/2017 | Hill et al. |
| 2018/0057483 A1 | 3/2018 | Zhu et al. |
| 2019/0216879 A1 | 7/2019 | Chahwan et al. |
| 2021/0252100 A1 | 8/2021 | Chahwan et al. |
| 2024/0287626 A1 | 8/2024 | Soloveychik et al. |
| 2025/0177474 A1 | 6/2025 | Chahwan et al. |

FOREIGN PATENT DOCUMENTS

| | | |
|---|---|---|
| AU | 745504 B2 | 3/2002 |
| AU | 2001283226 A1 | 2/2003 |
| AU | 762910 B2 | 7/2003 |
| AU | 2003265864 A8 | 3/2004 |
| AU | 775227 B2 | 7/2004 |
| AU | 783233 B2 | 10/2005 |
| AU | 2001245584 B2 | 2/2007 |
| AU | 2001247296 A8 | 4/2009 |
| CA | 2217545 A1 | 10/1996 |
| CA | 2272991 A1 | 5/1998 |
| CA | 2309754 A1 | 5/1999 |
| CA | 2310624 A1 | 5/1999 |
| CA | 2417135 A1 | 5/1999 |
| CA | 2386258 A1 | 4/2001 |
| CA | 2402111 A1 | 9/2001 |
| CA | 2402855 A1 | 9/2001 |
| CA | 2325447 C | 8/2007 |
| CA | 2317816 C | 2/2009 |
| CA | 2674084 C | 5/2013 |
| CA | 2376665 C | 2/2014 |
| CN | 1768142 A | 5/2006 |
| CN | 1905864 A | 1/2007 |
| CN | 101674820 B | 9/2013 |
| DE | 60120942 T2 | 2/2007 |
| DE | 69935313 T2 | 11/2007 |
| DE | 69935539 T2 | 12/2007 |
| DK | 2099442 T3 | 2/2015 |
| EP | 0942926 A2 | 9/1999 |
| EP | 1222261 A2 | 7/2002 |
| EP | 1263777 A2 | 12/2002 |
| EP | 1263951 A2 | 12/2002 |
| EP | 1049797 | 12/2004 |
| EP | 1032590 | 4/2005 |
| EP | 1575553 A2 | 9/2005 |
| EP | 1268842 B1 | 6/2006 |
| EP | 1731609 A1 | 12/2006 |
| EP | 0830459 B1 | 1/2007 |
| EP | 1053347 B1 | 2/2007 |
| EP | 1315958 B1 | 3/2007 |
| EP | 1810028 A2 | 7/2007 |
| EP | 2009442 A2 | 12/2008 |
| EP | 1200607 B1 | 2/2010 |
| EP | 2626067 A1 | 8/2013 |
| ES | 2284245 | 11/2007 |
| ES | 2529147 T3 | 2/2015 |
| JP | H11502717 A | 3/1999 |
| JP | 2001505418 A | 4/2001 |
| JP | 2002505072 A | 2/2002 |
| JP | 2003515314 A | 5/2003 |
| JP | 2003524371 A | 8/2003 |
| JP | 2004500805 A | 1/2004 |
| JP | 2004512001 A | 4/2004 |
| JP | 2004215624 A | 8/2004 |
| JP | 2005095613 A | 4/2005 |
| JP | 2007075107 A | 3/2007 |
| JP | 2008516979 A | 5/2008 |
| JP | 4440464 B2 | 3/2010 |
| JP | 2010514777 A | 5/2010 |
| JP | 2014139181 A | 7/2014 |
| JP | 5827706 B2 | 12/2015 |
| KR | 20090101362 A | 9/2009 |
| KR | 20120090100 A | 8/2012 |
| NZ | 578428 A | 3/2012 |
| PT | 2099442 E | 2/2015 |
| RU | 2009126655 A | 2/2011 |
| RU | 2446796 C2 | 4/2012 |
| RU | 2011148293 A | 6/2013 |
| SI | 2099442 T1 | 3/2015 |
| WO | WO-9632503 A1 | 10/1996 |
| WO | WO-9640721 A1 | 12/1996 |
| WO | WO-9807845 A1 | 2/1998 |
| WO | WO-9820030 A2 | 5/1998 |
| WO | WO-9925735 A1 | 5/1999 |
| WO | WO-9925865 A1 | 5/1999 |
| WO | WO-9935282 A1 | 7/1999 |
| WO | WO-9949294 A2 | 9/1999 |
| WO | WO-0042064 A1 | 7/2000 |
| WO | WO-0053630 A2 | 9/2000 |
| WO | WO-0075347 A2 | 12/2000 |
| WO | WO-0125420 A2 | 4/2001 |
| WO | WO-0166565 A9 | 9/2001 |
| WO | WO-0166787 A1 | 9/2001 |
| WO | WO-0168846 A2 | 9/2001 |
| WO | WO-0192523 A2 | 12/2001 |
| WO | WO-02058738 A2 | 8/2002 |
| WO | WO-03013488 A2 | 2/2003 |
| WO | WO-2004019890 A2 | 3/2004 |
| WO | WO-2004020457 A2 | 3/2004 |
| WO | WO-2004074479 A1 | 9/2004 |
| WO | WO-2005095613 A1 | 10/2005 |
| WO | WO-2006052391 A2 | 5/2006 |
| WO | WO-2008082856 A1 | 7/2008 |
| WO | WO-2009018219 A2 | 2/2009 |
| WO | WO-2012019157 A2 | 2/2012 |
| WO | WO-2013016810 A1 | 2/2013 |
| WO | WO-2014085545 A1 | 6/2014 |
| WO | WO-2015138377 A1 | 9/2015 |
| WO | WO-2017205852 A2 | 11/2017 |
| WO | WO-2019104244 A1 | 5/2019 |

OTHER PUBLICATIONS

Buchhop et al. Interaction of p53 with the human Rad51 protein. Nucleic Acids Res 25(19):3868-3874 (1997).

Budke et al. An optimized RAD51 inhibitor that disrupts homologous recombination without requiring Michael acceptor reactivity. J Med Chem 56:254-263 (2013).

Budke et al. RI-1: a chemical inhibitor of RAD51 that disrupts homologous recombination in human cells. Nucleic Acids Res 40:7347-7357 (2012).

Cancer Types. NIH National Cancer Institute. Retrieved Aug. 2, 2019 at URL: "title=Link: https://www.cancer.gov/types>">https://www.cancer.gov/types. 8 pages.

Cervical Cancer: Chemotherapy. University of Rochester Medical Center. Health Encyclopedia online. Available Dec. 20, 2011. Retrieved Aug. 2, 2019 at URL: https://www.urmc.rochester.edu/encyclopedia/content.aspx?contenttypeid=34&contentid=17238 -1. 6 pages.

Chen et al. The homologous recombination protein RAD51 is a promising therapeutic target for cervical carcinoma. Oncology Reports 38:767-774 (2017).

Chiu et al. DNA Repair Protein Rad51 Induces Tumor Growth and Metastasis in Esophageal Squamous Cell Carcinoma via a p38/Akt-Dependent Pathway. Ann Surg Oncol (2019). Published online Nov. 20, 2019. DOI: https://doi.org/10.1245/s10434-019-08043-x. 12 pages.

Connell et al. Pilot study examining tumor expression of RAD51 and clinical outcomes in human head cancers. Int. J. Oncol. 28(5):1113-1119 (May 2006).

D Amino Acid Peptides. Lifetein.com. Available May 12, 2012. Retrieved Aug. 2, 2019 at URL: "title=Link: https://www.lifetein.com/Peptide-Synthesis-D-Amino-Acid.html>">https://www.lifetein.com/Peptide-Synthesis-D-Amino-Acid.html. 8 pages.

Dunlop et al. Mechanistic insights into RAD51-associated protein 1 (RAD51AP1) action in homologous DNA repair. J Biol Chem 287(15):12343-12347 (2012).

(56) References Cited

OTHER PUBLICATIONS

EP17803737.0 Extended European Search Report dated Sep. 25, 2019.

Expression of RAD51 in Cancer—Summary, The Human Protein Atlas (website). Accessed Nov. 1, 2020 at URL: https:// www. proteinatlas.org/ENSG00000051180-RAD51/pathology. 3 pages.

Friedler et al. Binding of Rad51 and other peptide sequences to a promiscuous, highly electrostatic binding site in p53. J Biol Chem. Mar. 4, 2005;280(9):8051-9. doi: 10.1074/jbc.M411176200. Epub Dec. 20, 2004.

Gachechiladze et al. RAD51 as a potential surrogate marker for DNA repair capacity in solid malignancies. Int J Cancer 141:1286-1294 (2017). Published online May 6, 2017.

GenBank Accession No. CAA93344. Version No. CAA93344.1. ATP-dependent DNA helicase, UvrD subfamily [Schizosaccharomyces pombe]. Record created Feb. 9, 1996. 2 pages. Retrieved Apr. 23, 2022 at URL: https://www.ncbi.nlm.nih.gov/protein/ caa93344.

GenBank Accession No. CAJ02961. Version No. CAJ02961.1. conserved hypothetical protein [Leishmania major strain Friedlin]. Record created Jun. 21, 2005. 2 pages. Retrieved Apr. 23, 2022 at URL: https://www.ncbi.nlm.nih.gov/protein/caj02961.

Hannay et al. Rad51 overexpression contributes to chemoresistance in human soft tissue sarcoma cells: a role for p53/activator protein 2 transcriptional regulation. Mol Cancer Ther 6(5):1650-1660 (May 2007).

Hu et al. High expression of RAD51 promotes DNA damage repair and survival in KRAS-mutant lung cancer cells. BMB Rep. Feb. 2019; 52(2): 151-156. Epub Feb. 28, 2019. doi: 10.5483/BMBRep. 2019.52.2.213.

Huang et al. Identification of specific inhibitors of human RAD51 recombinase using high-throughput screening. ACS Chem Biol 6:628-635 (2011).

Inoue et al. p53 Protein Transduction Therapy: Successful Targeting and Inhibition of Growth of the Bladder Cancer Cells. European Urology 49:161-168 (2006).

Jerabek-Willemsen et al. Molecular interaction studies using microscale thermophoresis. Assay Drug Dev. Technol. 9:342-353 (2011).

Jiang et al. Network Analysis of RAD51 Proteins in Metazoa and the Evolutionary Relationships With Their Archaeal Homologs. Front Genet, vol. 9, Article 383 (Sep. 26, 2018). DOI: https://doi. org/10.3389/fgene.2018.00383. 9 pages.

Klein. The Consequences of Rad51 Overexpression for Normal and Tumor Cells. DNA Repair (Amst). May 3, 2008; 7(5): 686-693. Published online Feb. 1, 2008. doi: 10.1016/j.dnarep.2007.12.008.

Kovalenko et al. A novel nucleic acid-binding protein that interacts with human rad51 recombinase. Nucleic Acids Res 25(24):4946-4953 (1997).

Li et al. Overexpression of Rad51 Predicts Poor Prognosis in Colorectal Cancer: Our Experience with 54 Patients. PLoS One 12(1):e0167868 (Jan. 18, 2017). doi: 10.1371/journal.pone. 0167868. 11 pages. Retraction in PLoS One. Nov. 1, 2018;13(11):e0206398. doi: 10.1371/journal.pone.0206398. eCollection 2018. One page.

Liu et al. RAD51 Mediates Resistance of Cancer Stem Cells to PARP Inhibition in Triple-Negative Breast Cancer. Clin Canc Res 23(2):514-522 (2017). Published online Dec. 29, 2016. DOI: 10.1158/ 1078-0432.CCR-15-1348.

Maacke et al. Autoantibodies in sera of pancreatic cancer patients identify recombination factor Rad51 as a tumour-associated antigen. J Cancer Res Clin Oncol 128:219-222 (2002). Published online Feb. 6, 2002. DOI: https://doi.org/10.1007/s00432-001-0321-2.

Maacke et al. DNA repair and recombination factor Rad51 is over-expressed in human pancreatic adenocarcinoma. Oncogene 19:2791-2795 (2000). DOI: https://doi.org/10.1038/sj.onc.1203578.

Martin et al. RAD51 Up-regulation Bypasses BRCA1 Function and Is a Common Feature of BRCA1-Deficient Breast Tumors. Cancer Res 67(20):9658-65 (Oct. 15, 2007).

Marzio et al. The F-Box Domain-Dependent Activity of EMI1 Regulates PARPi Sensitivity in Triple-Negative Breast Cancers. Mol Cell. Jan. 17, 2019;73(2):224-237.e6. Epub Dec. 13, 2018. doi: 10.1016/j.molcel.2018.11.003.

Mason et al. The RAD51-stimulatory compound RS-1 can exploit the RAD51 overexpression that exists in cancer cells and tumors. Cancer Res. Jul. 1, 2014; 74(13): 3546-3555. Published online Apr. 21, 2014. doi: 10.1158/0008-5472.CAN-13-3220.

Milletti. Cell-penetrating peptides: classes, origin, and current landscape. Drug Discov Today. Aug. 2012; 17(15-16):850-60. doi: 10.1016/j.drudis.2012.03.002. Epub Mar. 23, 2012.

Nagathihalli et al. RAD51 as a potential biomarker and therapeutic target for pancreatic cancer. Biochimica et Biophysica Acta 1816(2):209-218 (2011). Available online Jul. 23, 2011. DOI: 10.1016/j.bbcan. 2011.07.004.

NCBI Reference Sequence: NP_594341.1 (2 pgs.) (Apr. 3, 2018).

NCBI Reference Sequence: XP_013017057.1 (2 pgs.) (Jul. 16, 2015).

PCT/US2017/034870 International Search Report and Written Opinion dated Dec. 11, 2017.

PCT/US2017/034870 Invitation to Pay Additional Fees dated Sep. 29, 2017.

PCT/US2018/062351 International Search Report and Written Opinion dated Feb. 21, 2019.

Qiao et al. High-level expression of Rad51 is an independent prognostic marker of survival in non-small-cell lung cancer patients. British Journal of Cancer 93:137-143 (2005). Published online Jun. 14, 2005.

Rogers et al. Chromosome and gene copy number variation allow major structural change between species and strains of *Leishmania*. Genome Res. Dec. 2011;21(12):2129-42. Epub Oct. 28, 2011.

Schild et al. Overexpression of RAD51 suppresses recombination defects: a possible mechanism to reverse genomic instability. Nucleic Acids Res. Mar. 2010; 38(4): 1061-1070. Published online Nov. 26, 2009. doi: 10.1093/nar/gkp1063.

Slupianek et al. BCR/ABL Regulates Mammalian RecA Homologs, Resulting in Drug Resistance. Molecular Cell 8:795-806 (Oct. 2001).

Tennstedt et al. RAD51 overexpression is a negative prognostic marker for colorectal adenocarcinoma. Int J Cancer 132:2118-2126 (2013). Published online Oct. 15, 2012.

U.S. Appl. No. 15/683,586 Notice of Allowance dated Sep. 11, 2018.

U.S. Appl. No. 15/683,586 Office Action dated Jan. 10, 2018.

U.S. Appl. No. 15/683,586 Office Action dated Jun. 8, 2018.

U.S. Appl. No. 16/215,432 Office Action dated Nov. 10, 2020.

U.S. Appl. No. 16/215,432 Office Action dated Sep. 9, 2019.

Varshavsky. The N-end rule: functions, mysteries, uses. PNAS USA 93:12142-12149 (1996).

Vidal et al. Prospects for drug screening using the reverse two-hybrid system. TIBTECH, vol. 17, pp. 374-381 (Sep. 1999).

Wiegmans et al. Rad51 supports triple negative breast cancer metastasis. Oncotarget 5(10):3261-3272 (Apr. 27, 2014). DOI: https://doi.org/10.18632/oncotarget.1923.

Woditschka et al. DNA Double-Strand Break Repair Genes and Oxidative Damage in Brain Metastasis of Breast Cancer. JNCI: Journal of the National Cancer Institute , vol. 106, Issue 7 (Jul. 2014). Published online Jun. 19, 2014. DOI: https://doi.org/10.1093/ jnci/dju145. 13 pages.

Wood et al. The genome sequence of Schizosaccharomyces pombe. Nature, vol. 415, pp. 871-880 (Feb. 21, 2002). With Corrigenda, Nature, vol. 421, p. 94 (Jan. 2, 2003).

Ying. Synthesis of BRC4-like peptide and its interaction with RAD51 (231-260). Henan University of Technology, 2014. Retrieved Sep. 28, 2021 at: https://t.cnki.net/kcms/detail?v=3uoqlhG8C475KOm_ zrgu4IQARvep2SAkbl4wwVeJ9RmnJRGnwiiNVvMG4_ ewJd8c3MnYzhXsRgUXcAs0a-QEt5vvYByjvUme&uniplatform= NZKPT. Abstract with English translation. 6 pages.

Zhao et al. Research progresses on the interaction sites between BRC4 motif of BRCA2 and RAD51. Chinese Bulletin of Life Sciences, Issue 2, pp. 198-202 (2015). Retrieved Sep. 27, 2021 at: http://www.tzsti.com:85/Qikan/Article/Detail?id=663838456&from= Qikan_Search_Index. English abstract only. 3 pages.

(56) References Cited

OTHER PUBLICATIONS

Zhu et al. A novel small molecule RAD51 inactivator overcomes imatinib-resistance in chronic myeloid leukaemia. EMBO Mol Med 5(3):353-365 (2013).

Alberts et al. Molecular Biology of the Cell, Chapter 8 (Manipulating Proteins, DNA, and RNA), Section 4 (Analyzing protein structure and function), Subtitle "Protein-Protein Interactions Can Be Identified by Use of the Two-Hybrid System." 4th edition, New York: Garland Science (2002). 2 pages.

Bacterial Display. [online] Rx Biosciences. Sep. 22, 2015. Retrieved Jul. 21, 2023 at URL: https://rxbiosciences.com/our-services/phage-display/bacterial-display/. 2 pages.

EP23188944.5 Extended European Search Report dated Oct. 23, 2023.

Heterologous. [online] Merriam-Webster. Accessed Jul. 21, 2023 at URL: https://www.merriamwebster.com/dictionary/heterologous#:~: text=%3A derived from a different species. 11 pages.

Stynen et al. Diversity in Genetic In Vivo Methods for Protein-Protein Interaction Studies: from the Yeast Two-Hybrid System to the Mammalian Split-Luciferase System. Microbiology and Molecular Biology Reviews, vol. 76, No. 2, pp. 331-382 (Jun. 2012).

U.S. Appl. No. 16/876,809 Notice of Allowance dated Jun. 28, 2023.

U.S. Appl. No. 16/876,809 Office Action dated Apr. 28, 2022.

U.S. Appl. No. 16/876,809 Office Action dated Mar. 13, 2023.

U.S. Appl. No. 17/171,841 Office Action dated Jul. 28, 2023.

U.S. Appl. No. 17/171,841 Office Action dated Mar. 8, 2023.

Young. Yeast Two-hybrid: So Many Interactions, (in) So Little Time . . . Biology of Reproduction, vol. 58, pp. pp. 302-311 (1998).

U.S. Appl. No. 17/171,841 Office Action dated Aug. 21, 2024.

U.S. Appl. No. 17/171,841 Notice of Allowance dated Nov. 5, 2024.

Binding of Compounds on a novel site of
Rad51 – modelling on 1N0W PDB structure

Compound binding sites D187, Q202, Y205, Q206 highlighted in dark
BRCA2 peptide highlighted in gray Compound 1 works with extremely acute kinetics hr:min:sec A549 untreated A549 + Compound 1

DAPI
NSCLC - non small cell lung cancer

Imaging Studies of Calcium Accumulation in
Response to Compound 1 → hr:min:sec

*FIG. 8*

NSCLC (A549)
2.5uM Fluo-2 AM
30uM Compound 1

Imaging Studies of Calcium Accumulation in
Response to Compound 1 – individual cells NSCLC (A549)
2.5uM Fluo-2 AM
30uM Compound 1

Compound 22 A549 xenograft data

A549 xenograft - tumor volume

A549 xenograft - body weight

COMPOUNDS FOR SELECTIVE DISRUPTION OF PROTEIN-PROTEIN INTERACTIONS

CROSS-REFERENCE

This application is a continuation of U.S. application Ser. No. 16/876,809, filed May 18, 2020, which is a continuation application of International Application No. PCT/US2018/062351, filed Nov. 21, 2018, which claims the benefit of U.S. Provisional Application No. 62/590,056, filed on Nov. 22, 2017, which applications are herein incorporated by reference in their entirety.

SEQUENCE LISTING

The instant application contains a Sequence Listing which has been submitted electronically in XML format and is hereby incorporated by reference in its entirety. Said XML file, created on Jan. 29, 2025, is named 50607-706_302_SL.xml and is 441,949 bytes in size.

BACKGROUND

Cancer, an uncontrolled proliferation of cells, is a multifactorial disease characterized by tumor formation, growth, and in some instances, metastasis. Current cancer therapies include chemotherapy and targeted therapies, which attempt to destroy cancer cells via apoptosis, necrosis, or proliferative inhibition. Deoxyribonucleic acid (DNA) repair pathways are frequently overexpressed in cancer cells, and can be essential to the proliferation of chemotherapy-resistant cancers. Thus, compounds that can attenuate aberrant DNA damage repair pathway signaling could be beneficial to cancer patients. However, such signaling pathways in DNA repair and cancer frequently involve protein-protein interactions as critical regulatory steps, making the traditional enzyme active-site inhibitor-based drug development scheme challenging. Accordingly, there is need for development of methods and compositions that target protein-protein interactions in cancer and DNA repair.

SUMMARY

The present disclosure is directed to compositions of protein-protein interaction inhibitors aimed at disrupting the function of DNA repair pathways and/or causing death of cancer cells.

In one aspect, the present disclosure provides for a non-naturally occurring peptide comprising a targeting motif of Formula I or an invert thereof:

(Formula I)
(SEQ ID NO: 61)
$$L-X_1-R-X_2-V-R-L-R-X_3-Y_1-L-R-X_4$$

wherein:

$X_1$-$X_4$ and $Y_1$ are independently selected from the 20 natural L- or D-amino acids, or L- or D-isomers of Nle, Met(O), Met(O)2, Se-Met, Abu (α-aminobutyric acid), Bal (Beta-Alanine), Hse, nme-Ser, and Ahx, and wherein L, R, and V are D- or L-amino acids.

In some embodiments, the amino acids of Formula I are all D-amino acids. In some embodiments, the amino acids of Formula I are all L-amino acids. In some embodiments, the peptide comprises the inverse of Formula I. In some embodiments, at least one of $X_1$-$X_4$ and/or $Y_1$ is other than the 21 canonical L- or D-amino acids amino acids. In some embodiments, $X_1$ is not L- or D-Met. In some embodiments, $X_2$ is not L- or D-Ser. In some embodiments, $X_3$ is not L- or D-Val. In some embodiments, $X_4$ is not L- or D-Lys. In some embodiments, $Y_1$ is not L- or D-Gly. In some embodiments, $X_1$ is L- or D-Nle. In some embodiments, $X_2$ is selected from L- or D-isomers of Abu, Bal, and Ala. In some embodiments, $X_3$ is L- or D-Nle. In some embodiments, $Y_1$ is L- or D-Bal. In some embodiments, X4 is selected from L- or D-isomers of Arg or Ahx. In some embodiments, the peptide is according to Formula IA or an invert thereof:

(Formula IA)
(SEQ ID NO: 126)
$$Dan-Sar-L-X_1-R-X_2-V-R-L-R-X_3-Y1-L-R-X_4$$

wherein:

Dan is Dansyl, Sar is Sarcosine, and L, S, V, and R are L- or D-amino acids. In some embodiments, $Y_1$ is L- or D-Bal or Gly. In some embodiments, $X_1$ is a hydrophobic amino acid selected from L- or D-Val, Ile, Leu, Met, Phe, Trp, Cys, d-Nle, Met(O), Met(O)2, and Se-Met; $X_2$ and $X_3$ are independently selected from a neutral or hydrophilic amino acid selected from L- or D-Ser, Gly, Abu, Ala, Bal, Tyr, His, Thr, and Pro; and $X_4$ is a positively charged amino acid selected from L- or D-Lys, Arg, and Ahx. In some embodiments, $X_1$ is selected from L- or D-Met, Val, and d-Nle; $X_2$ is selected from L- or D-Ser, Gly, Abu, and Bal; $X_3$ is selected from L- or D-Val and d-Nle; and $X_4$ is selected from L- or D-Lys, Arg, and Ahx. In some embodiments, the peptide comprises any of the targeting motifs of Table 4. In some embodiments, the peptide is selected from compound 1-25. In some embodiments, the peptide comprises a cell-penetrating peptide motif, or a retro-invert thereof. In some embodiments, the cell-penetrating motif is C-terminal to the motif of Formula I. In some embodiments, the peptide is according to Formula IB or IC, or an invert thereof:

(Formula IB)
(SEQ ID NO: 127)
$$L-X_1-R-X_2-V-R-L-R-X_3-G-L-R-\Omega;$$
or (Formula IC)
(SEQ ID NO: 128)
$$L-X_1-R-X_2-V-R-L-R-X_3-G-L-R-X_4-Z-\Omega$$

wherein: $\Omega$ is a cell-penetrating peptide sequence or a retro-invert thereof, and Z is at least one neutral or hydrophilic amino acid selected from L- or D-Ser, Gly, Abu, Ala, Bal, Tyr, His, Thr, Pro. In some embodiments, the cell-penetrating peptide is AIP6, DPV6, HIV-1 TAT, IRS-tag, mini-penetratin, penetratin, $R_7$(SEQ ID NO: 129), $R_8$ (SEQ ID NO: 8), $R_9$ (SEQ ID NO: 131), $R_{10}$ (SEQ ID NO: 132), $R_{11}$ (SEQ ID NO: 133), $R_{12}$ (SEQ ID NO: 134), R9F2C (SEQ ID NO: 135), cFΦR4 (SEQ ID NO: 54), CADY, EB-1, hCT, PTD4, MAP, Pep-1, pVEC, SynB1f, Transportan, VP1, MAP17, PreS2, GALA, MAP12, $(PPR)_n$, $(PRR)_n$, Bac-7, SAP, BIP, C105Y, β3-integrin, K-FGF, NF-κB, Pep7, j1-tail, rrrrrrr (SEQ ID NO: 147), cFΦR4 (SEQ ID NO: 54), rrrrGy (SEQ ID NO: 148), rrrrrGΦ (SEQ ID NO: 149), rrrrrrk(C6_5FAM) (SEQ ID NO: 150), rrrrr-sarcosine-sarcosine-OMe (SEQ ID NO: 151), or r(Ahx) r(Ahx)r(Ahx)r(Ahx)r(Ahx)r (SEQ ID NO: 152), or r(Ahx)r(Ahx)r(Ahx)r(Ahx)r(Ahx)r(Ahx)y (SEQ ID NO: 153), or a retro-invert thereof, or a combination thereof. In some embodiments, the cell penetrating peptide sequence is rrrrrrr (SEQ ID NO: 147), cFΦR4 (SEQ ID NO: 54), rrrrGy (SEQ ID NO: 148), rrrrrGΦ (SEQ ID NO: 149), rrrrrrrk(C6_5FAM) (SEQ ID NO: 150), rrrrrr-sarcosine-sarcosine-OMe (SEQ ID NO: 151), r(Ahx)r(Ahx)r(Ahx)r(Aha)r(Ahx)r, or r(Ahx)r (Ahx)r(Ahx)r(Ahx)r(Ahx)y (SEQ ID NO: 153), or a retro-invert thereof, or a combination thereof. In some embodiments, the peptide inhibits RAD51. In some embodiments, the peptide inhibits RAD51 non-competitively. In some embodiments, the peptide induces death of mammalian cells having amplification of the RAD51 gene. In some embodiments, the IC50 of the compound in a hemolysis assay is greater than 250 μM. In some embodiments, the compound is selected from compound 1, 2, 15, 17, 19, 20, 21, 22, 23, 24, and 25. In some embodiments, the peptide has a half-life of greater than 30 minutes when administered intraperi-toneally or subcutaneously. In some embodiments, the peptide has a half-life of greater than 7 minutes or 20 minutes when administered intravenously. In some embodiments, the peptide has half-life in a mouse serum stability assay of greater than 200 minutes. In some embodiments, the peptide has a half-life in a human or mouse microsome assay of greater than 30 minutes. In some embodiments, the peptide comprises fewer than 100, fewer than 80, fewer than 60, fewer than 40, fewer than 30, or fewer than 20 amino acids. In some embodiments, the peptides have an EC50 in a RAD51 overexpressing or amplified cell line of less than 500 μM, less than 450 μM, less than 400 μM, less than 350 μM, less than 300 μM, less than 250 μM, less than 200 μM, less than 150 μM, less than 100 μM, less than 90 μM, less than 80 μM, less than 70 μM, less than 60 μM, less than 50 μM, less than 40 μM, less than 30 μM, less than 20 μM, less than 10 μM, less than 9 μM, less than 8 μM, less than 7 μM, less than 6 μM, less than 5 μM, less than 4 μM, less than 3 μM, less than 2 μM, less than 1 μM, less than 0.5 μM, less than 0.25 μM, or less than 0.1 μM.

In some aspects, the present disclosure provides for a non-naturally occurring peptide comprising Formula II or an invert thereof:

(Formula II)
(SEQ ID NO: 136)
$$L-X_1-R-X_2-V-R-L-R-X_3-Y_1-L$$

wherein: $X_1$-$X_4$ and $Y_1$ are independently selected from the 20 common D- or L-amino acids, or L- or D-isomers of Nle, Met(O), Met(O)2, Se-Met, Abu (α-aminobutyric acid), Bal (Beta-Alanine), Hse, nme-Ser, and Ahx, and wherein L, R, and V are D- or L-amino acids. In some embodiments, $X_1$ is not L- or D-Phe, $X_2$ is not L- or D-Cys, and $X_3$ is not L- or D-Glu. In some embodiments, the amino acids of Formula II are all D-amino acids. In some embodiments, the amino acids of Formula II are all L-amino acids. In some embodiments, the peptide comprises the inverse of Formula II. In some embodiments, at least one of $X_1$-$X_4$ and/or $Y_1$ is other than the 20 common L- or D-amino acids amino acids. In some embodiments, $X_1$ is not L- or D-Met. In some embodiments, $X_2$ is not L- or D-Ser. In some embodiments, $X_3$ is not L- or D-Val. In some embodiments, $Y_1$ is not L- or D-Gly. In some embodiments, $X_1$ is L- or D-Nle. In some embodiments, $X_2$ is selected from L- or D-isomers of Abu, Bal, and Ala. In some embodiments, $X_3$ is L- or D-Nle. In some embodiments, $Y_1$ is L- or D-Bal. In some embodiments, the peptide is according to Formula I or a invert thereof:

(Formula I)
(SEQ ID NO: 61)
$$L-X_1-R-X_2-V-R-L-R-X_3-Y_1-L-R-X_4$$

wherein: $X_1$-$X_4$ and $Y_1$ are independently selected from the 20 common L- or D-amino acids, or L- or D-isomers of Nle, Met(O), Met(O)2, Se-Met, Abu (α-aminobutyric acid), Bal (Beta-Alanine), Hse, nme-Ser, and Ahx, and wherein L, R, and V are L- or D-amino acids. In some embodiments, the peptides have an EC50 in a RAD51 overexpressing or amplified cell line of less than 500 μM, less than 450 μM, less than 400 μM, less than 350 μM, less than 300 μM, less than 250 μM, less than 200 μM, less than 150 μM, less than 100 μM, less than 90 μM, less than 80 μM, less than 70 μM, less than 60 μM, less than 50 μM, less than 40 μM, less than 30 μM, less than 20 μM, less than 10 μM, less than 9 μM, less than 8 μM, less than 7 μM, less than 6 μM, less than 5 μM, less than 4 μM, less than 3 μM, less than 2 μM, less than 1 μM, less than 0.5 μM, less than 0.25 μM, or less than 0.1 μM.

In some aspects, the present disclosure provides for a peptide comprising fewer than 100 amino acids, wherein the peptide comprises a target sequence and a cell-penetrating peptide sequence, wherein the target sequence is according to Formula III or a invert thereof:

(Formula III)
$$A_1-X_1-B_1-X_2-C-B_2-A_2-B_3-X_3-D-A_3-B_4-X_4$$

wherein: $A_1$-$A_3$ are independently selected from or L- or D-Leu, Nle, nme-Leu, Beta-HomoLeu, 5,5,5-Trifluoro-L-leucine, Ile, nme-Ile, Met, Met(O), Met(O)2, Se-Met, Val, Nva, and nme-Val; B1-B4 are independently selected from or L- or D-Arg, Pra, Arg(Me), ADMA, SDMA, Ahx, Lys, and Lys-Ac; C is selected from or L- or D-Val, Nva, and nme-Val; D is selected from or L- or D-Gly and Beta-Ala; $X_1$ is selected from or L- or D-Met, d-Nle, Met(O), Met(O)2, and Se-Met; $X_2$ is selected from or L- or D-Ser, Abu (α-aminobutyric acid), Bal (Beta-Alanine), Gly, Thr, Hse, and nme-Ser; $X_3$ is selected from or L- or D-Val, Glu, d-Nle, Ile, Leu, and Met; and $X_4$ is selected from or L- or D-Lys, Arg, Ahx. In some embodiments, the amino acids of Formula III are all D-amino acids. In some embodiments, the amino acids of Formula III are all L-amino acids. In some embodiments, the peptide comprises the inverse of Formula III. In some embodiments, at least one of $X_1$-$X_4$ and/or $Y_1$ is other than the 20 common L- or D-amino acids amino acids. In some embodiments, the peptide comprises fewer than 100, fewer than 80, fewer than 60, fewer than 40, fewer than 30, or fewer than 20 amino acids. In some embodiments, one of $A_1$-$A_3$ is or L- or D-Leu. In some embodiments, one of $B_1$-$B_4$ is or L- or D-Arg. In some embodiments, C is or L- or D-Val. In some embodiments, D is or L- or D-Gly. In some embodiments, D is or L- or D-Bal. In some embodiments, the peptide comprises at least one non-common amino acid. In some embodiments, the peptides have an EC50 in a RAD51 overexpressing or amplified cell line of less than 500 μM, less than 450 μM, less than 400 μM, less than 350 μM, less than 300 μM, less than 250 μM, less than 200 μM, less than 150 μM, less than 100 μM, less than 90 μM, less than 80 μM, less than 70 μM, less than 60

µM, less than 50 µM, less than 40 µM, less than 30 µM, less than 20 µM, less than 10 µM, less than 9 µM, less than 8 µM, less than 7 µM, less than 6 µM, less than 5 µM, less than 4 µM, less than 3 µM, less than 2 µM, less than 1 µM, less than 0.5 µM, less than 0.25 µM, or less than 0.1 µM.

In some aspects, the present disclosure provides for a method of treating a malignancy, comprising administering a compound according to Formula II or a invert thereof:

$$\text{(Formula II)}$$
$$\text{(SEQ ID NO: 136)}$$
$$\text{L-}X_1\text{-R-}X_2\text{-V-R-L-R-}X_3\text{-}Y_1\text{-L}$$

wherein: $X_1$-$X_4$ and $Y_1$ are independently selected from the 20 common or L- or D-amino acids, or or L- or D-isomers of Nle, Met(O), Met(O)2, Se-Met, Abu (α-aminobutyric acid), Bal (Beta-Alanine), Hse, nme-Ser, and Ahx, wherein L, R, and V are or L- or D-amino acids. In some embodiments, the compound is selected from compounds 1-25. In some embodiments, the peptide comprises fewer than 100, fewer than 80, fewer than 60, fewer than 40, fewer than 30, or fewer than 20 amino acids. In some embodiments, the peptide comprises a cell-penetrating peptide motif. In some embodiments, the cell-penetrating motif is C-terminal to the motif of Formula I. In some embodiments, the peptide is according to Formula IB or IC or an invert thereof:

$$\text{(Formula IB)}$$
$$\text{(SEQ ID NO: 127)}$$
$$\text{L-}X_1\text{-R-}X_2\text{-V-R-L-R-}X_3\text{-G-L-R-}\Omega;$$
$$\text{or}$$

$$\text{(Formula IC)}$$
$$\text{(SEQ ID NO: 128)}$$
$$\text{L-}X_1\text{-R-}X_2\text{-V-R-L-R-}X_3\text{-G-L-R-}X_4\text{-Z-}\Omega$$

wherein: Ω is a cell-penetrating peptide sequence or an invert thereof; and Z is at least one neutral or hydrophilic amino acid selected from or L- or D-Ser, Gly, Abu, Ala, Bal, Tyr, His, Thr, Pro. In some embodiments, the cell-penetrating peptide is AIP6, DPV6, HIV-1 TAT, IRS-tag, mini-penetratin, penetratin, $R_7$ (SEQ ID NO: 129), $R_8$ (SEQ ID NO: 8), $R_9$ (SEQ ID NO: 131), $R_{10}$ (SEQ ID NO: 132), $R_{11}$ (SEQ ID NO: 133), $R_{12}$ (SEQ ID NO: 134), R9F2C (SEQ ID NO: 135), cFΦR4 (SEQ ID NO: 54), CADY, EB-1, hCT, PTD4, MAP, Pep-1, pVEC, SynB1, Transportan, VP1, MAP17, PreS2, GALA, MAP12, $(PPR)_n$, $(PRR)_n$, Bac-7, SAP, BIP, C105Y, β3-integrin, K-FGF, NF-κB, Pep7, β1-tail, rrrrrrr (SEQ ID NO: 147), cFΦR4 (SEQ ID NO: 54), rrrrGy (SEQ ID NO: 148), rrrrrGΦ (SEQ ID NO: 149), rrrrrrrk(C6_5FAM) (SEQ ID NO: 150), rrrrrr-sarcosine-sarcosine-OMe (SEQ ID NO: 151), r(Ahx)r(Ahx)r(Ahx)r(Ahx)r(Ahx)r (SEQ ID NO: 152), or r(Ahx)r(Ahx)r(Ahx)r(Ahx)r(Ahx)r(Ahx)y (SEQ ID NO: 153), or a retro-invert thereof. In some embodiments, the cell penetrating peptide sequence is rrrrrrr (SEQ ID NO: 147), cFΦR4 (SEQ ID NO: 54), rrrrGy (SEQ ID NO: 148), rrrrrGΦ (SEQ ID NO: 149), rrrrrrrk(C6_5FAM) (SEQ ID NO: 150), rrrrrr-sarcosine-sarcosine-OMe (SEQ ID NO: 151), r(Ahx)r(Ahx)r(Ahx)r(Ahx)r(Ahx)r (SEQ ID NO: 152), or r(Ahx)r(Ahx)r(Ahx)r(Ahx)r(Ahx)r(Ahx)y (SEQ ID NO: 153), or a retro-invert thereof. In some embodiments, the peptide inhibits RAD51. In some embodiments, the peptide inhibits RAD51 noncompetitively. In some embodiments, the peptide induces death of mammalian cells having amplification of the RAD51 gene. In some embodiments, the peptide has a half-life of greater than 30 minutes when administered intraperitoneally or subcutaneously. In some embodiments, the peptide has a half-life of greater than 7 minutes or 20 minutes when administered intravenously. In some embodiments, the peptide has half-life in a mouse serum stability assay of greater than 200 minutes. In some embodiments, the peptide has a half-life in a human or mouse microsome assay of greater than 30 minutes. In some embodiments, the compound is administered intravenously. In some embodiments, the compound is administered intraperitoneally or subcutaneously. In some embodiments, the compound have an EC50 in a RAD51 overexpressing or amplified cell line of less than 500 µM, less than 450 µM, less than 400 µM, less than 350 µM, less than 300 µM, less than 250 µM, less than 200 µM, less than 150 µM, less than 100 µM, less than 90 µM, less than 80 µM, less than 70 µM, less than 60 µM, less than 50 µM, less than 40 µM, less than 30 µM, less than 20 µM, less than 10 µM, less than 9 µM, less than 8 µM, less than 7 µM, less than 6 µM, less than 5 µM, less than 4 µM, less than 3 µM, less than 2 µM, less than 1 µM, less than 0.5 µM, less than 0.25 µM, or less than 0.1 µM.

INCORPORATION BY REFERENCE

Each patent, publication, and non-patent literature cited in the application is hereby incorporated by reference in its entirety as if each was incorporated by reference individually.

BRIEF DESCRIPTION OF THE FIGURES

The novel features of the disclosure are set forth with particularity in the appended claims. A better understanding of the features and advantages of the present disclosure will be obtained by reference to the following detailed description that sets forth illustrative aspects, in which the principles of the disclosure are utilized, and the accompanying drawings of which:

FIGS. 8 and 9 show A549 cells treated the calcium detection dye Fluo-2, and imaged using a Cytation instrument after compound 2 addition. Timepoints are shown as indicated.

DETAILED DESCRIPTION

Figure 1:
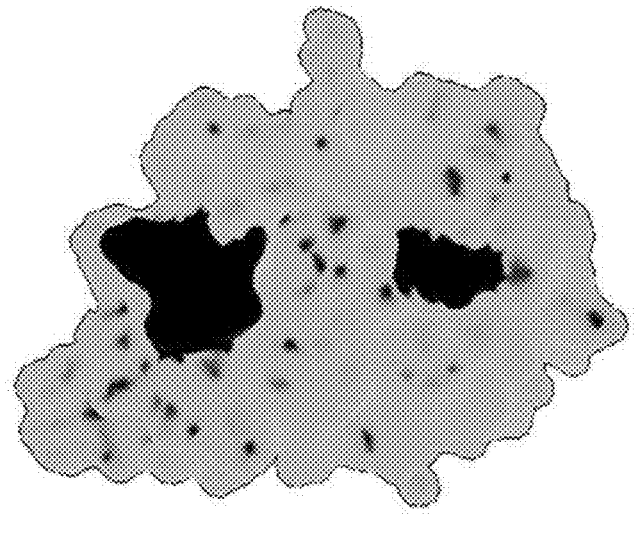
FIG. 1 shows a binding model of an exemplary RAD51 peptide according to the invention bound to RAD51 (as represented by PDB structure 1NOW). Residues identified for peptide binding are highlighted. The left panel shows a BRCA2 peptide bound on RAD51 (with the Compound interacting with the highlighted residues around the BRCA2 peptide), the right panel excludes this sequence of BRCA2 and highlights just the Compound-interacting residues on RAD51.
Figure 1:
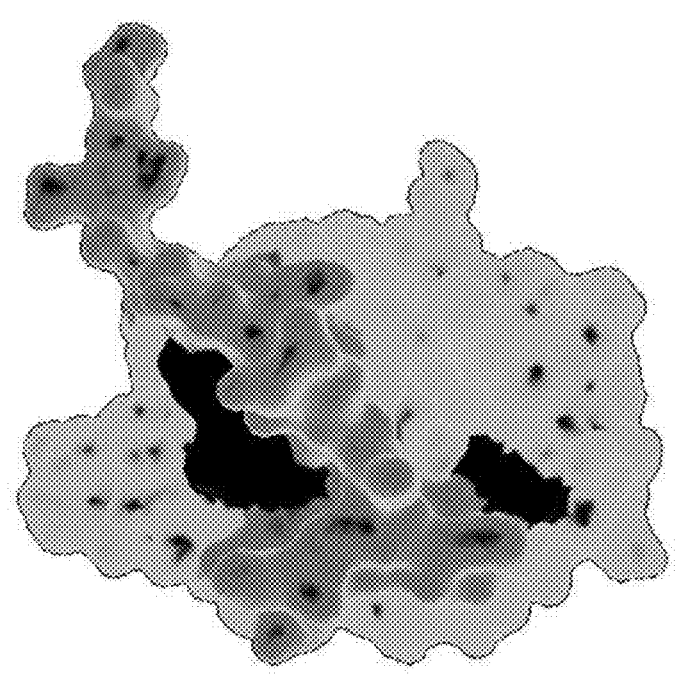

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides methods for the treatment of cancer using compounds that can bind to proteins involved in the homologous recombination DNA repair pathway. The present compounds can decrease the rate of cellular proliferation in cancer cells, and avoid affecting those cells that do not overexpress proteins specific to the DNA repair pathway. The present compounds can further sensitize cells to chemotherapy, and sensitize those cells that have developed resistance to therapeutics. The compounds disclosed herein can display specificity toward cancer cells harboring specific transcriptional signatures.

Cancer is a collection of related diseases characterized by uncontrolled proliferation of cells with the potential to metastasize throughout the body. Cancer can be classified into five broad categories including, for example, carcinomas, sarcomas, lymphomas, leukemias, and adenomas. Carcinomas can arise from cells that cover internal and external parts of the body such as the lung, breast, and colon. Sarcomas can arise from cells that are located in bone, cartilage, fat, connective tissue, muscle, and other supportive tissues. Lymphomas can arise in the lymph nodes and immune system tissues. Leukemias can arise in the bone marrow and accumulate in the bloodstream. Adenomas can arise in the thyroid, the pituitary gland, the adrenal gland, and other glandular tissues.

Although different cancers can develop in virtually any of the body's tissues, the basic processes that cause cancer can be similar in all forms of the disease. Cancer begins when a cell breaks free from the normal restraints on cell division and begins to grow and divide abnormally. Genetic mutations in the cell can preclude the ability of the cell to control cell division or initiate apoptosis, and can result in uncontrolled growth and division of cells.

Oncogenes and tumor suppressor genes can regulate the proliferation of cells. Genetic mutations can affect oncogenes and tumor suppressors, potentially activating or suppressing activity abnormally, further facilitating uncontrolled cell division. Whereas oncogenes assist in cellular growth, tumor suppressor genes slow cell division by repairing damaged DNA and activating apoptosis. Cellular oncogenes that can be mutated in cancer include, for example, Cdk1, Cdk2, Cdk3, Cdk4, Cdk6, c-MYC, EGFR, HER2, K-Ras, PDGFR, Raf kinase, and VEGF. Tumor suppressor genes that can be mutated in cancer include, for example, BRCA1, BRCA2, cyclin-dependent kinase inhibitor 1C, PTEN, p16, p2'7, p53, p'73, and Retinoblastoma protein (pRb).

DNA Damage and Cancer.

DNA damage can occur as a result of, for example, UV radiation, IR radiation, X-rays, reactive oxygen species, depurination, depyrimidination, single-strand breaks, double-strand breaks, cytosine deamination, 06-methylguanines, base alkylation, cross-linking of DNA, replication errors, or free radicals. Chemical compounds can also cause DNA damage by causing bulky adducts, interstrand crosslinks, intrastrand crosslinks, intercalation between DNA strands, or DNA alkylation. Compounds that can cause DNA damage include, for example, actinomycin-D, benzo[a]pyrenes, cisplatin, daunorubicin, ethidium bromide, nitrogen mustards, methyl methanesulphonate (MMS), N-ethyl-N-nitrosourea (ENU), N-nitroso-N-methylurea (NMU), or psoralens.

Mutations or precocious expression of the DNA damage repair pathway can be found in cancer. Genes that can be affected in the DNA damage repair pathway include, for example, ATM, ATRX, BRCA1, BRCA2, ERCC1, FANCB, FANCF, FEN1, HMGA1, HMGA1, MDC1, MGMT, MLH1, MSH2, MSH4, Mre11A, NBS1, NEIL1, PARP1, PARP2, PMS2, RAD51, RAD52, RAD54, RAD51AP1, WRN, or XPF.

BRCA1 and BRCA2 are tumor suppressors that are involved in the cellular DNA damage repair pathway. Both BRCA1 and BRCA2 can interact with RAD51, a eukaryotic recombinase involved in DNA repair. Germline mutations in BRCA1 or BRCA2 can predispose individuals to various cancers including, for example, breast, ovarian, prostate, lung, and liver cancers. Tumors with BRCA2 mutations can exhibit loss of heterozygosity of the wild-type allele.

BRCA1 can combine with other tumor suppressors, DNA damage sensors, and signal transducers to form a large multi-subunit protein complex known as the BRCA1-associated genome surveillance complex (BASC). BRCA1 can also associate with RNA polymerase II and histone deacetylase complexes. Thus, BRCA1 can play a role in transcription, DNA repair of double-stranded breaks, and recombination. BRCA1 has cell-cycle dependent localization and can be found in, for the example, the nucleus, cytoplasm, or endoplasmic reticulum.

BRCA2 can maintain genome stability, and both BRCA1 and BRCA2 can specifically regulate the homologous recombination pathway for double-strand DNA repair. The BRCA2 protein contains about seven copies of a 70 amino acid motif known as the BRC motif, which can mediate binding to the RAD51 recombinase. RAD51 can perform certain biochemical activities required for homologous recombination and DNA repair, for example, promotion of j joint molecule formation and DNA strand exchange between homologous DNA molecules. As a prerequisite for these functions, RAD51 can bind to DNA to form highly ordered nucleoprotein filaments in which the DNA is encased within a protein sheath. RAD51AP1 is a RAD51 accessory protein that can stimulate joint molecule formation through the combination of structure-specific DNA binding and physical contact with RAD51. RAD51AP1 can protect cells from the adverse effects of DNA double-strand break-inducing agents. Direct and specific interactions between the BRC3 or BRC4 repeats in BRCA2 and RAD51 can sequester RAD51 in a form that is ready to be localized to sites of DNA damage, and thus become activated for DNA repair. Lack of functional BRCA2, or overexpression of BRCA2, can perturb RAD51 function by, for example, preventing RAD51 from localizing to sites of DNA damage. These damaged sites, which can contain double-strand breaks formed at stalled or broken replication forks, or double-strand breaks induced by exogenous agents, can provide the signal for activation of the mammalian SOS repair response. Activation can involve the posttranslational modification of RAD51 or occur via interactions with other repair proteins.

The BRC motifs of BRCA2 can bind monomeric or oligomeric forms of RAD51 in a cell cycle-dependent manner and in response to DNA damage. BRCA2 protein can be directly involved in the nuclear transport of RAD51. For example, the pancreatic adenocarcinoma cell line CAPAN-1 is defective in BRCA2, which can lead to impaired nuclear transportation of RAD51 in CAPAN-1. Thus, RAD51 can require BRCA2 for nuclear translocation and proper homologous recombination processes.

Double-strand DNA breaks can be caused by, for example, natural and medical radiation and other environmental exposures. Double-strand DNA breaks can also occur when chromosomes exchange genetic material during meiosis and during repair of DNA crosslinks. By repairing DNA, BRCA1 and BRCA1 play a role in maintaining the stability of the human genome and reducing the likelihood of dangerous gene rearrangements that can lead to malignancies.

Cancer treatments using chemotherapy or radiotherapy can target and disrupt the function of the DNA of tumor cells by inducing adducts or DNA double-strand or single-strand breaks. Cancer cells can overcome these therapies by developing resistance mechanisms, which can either be induced or intrinsic to the cancer cells. A high level of homologous recombination can be present in cancer cells due to the overexpression of RAD51. This overexpression of RAD51 can be seen in, for example, breast cancer, pancreatic, glioblastoma, NSCLC, mCRPC, AML, ICC, and CML. In these cancer cells, the overexpression of RAD51 can provide cancer resistance by promoting the repair of double strand breaks induced by chemotherapy. Thus, the compounds of the present invention can interfere with the activity of RAD51, or other proteins involved in the DNA damage repair pathway, to resensitize cancer cells to chemotherapy, or to potentiate the effect of chemotherapy.

Compounds.

Disclosed herein are non-naturally occurring compounds that can bind to a protein interface of RAD51 and inhibit the function of RAD51 in vitro or in cells. The protein interface can be a subregion of the ATPase domain of RAD51. The protein interface can be RAD51AP1's binding site on RAD51. The protein interface can be amino acid residues 190-218 of human RAD51. An exemplary model of a protein interface where non-naturally occurring compounds according to the invention can bind on RAD51 is presented in FIG. 1, wherein compound interacts with residues highlighted in black. Gray shows the binding of BRCA2 to RAD51.

In vitro, compounds as disclosed herein can inhibit RAD51 multimerization, RAD51 interaction with another known interacting partner of RAD51 (e.g. BRCA2 or RAD51AP1), or RAD51 chelation/binding of Ca2+ ions. The inhibition of interaction with another known interacting partner of RAD51 may be competitive or allosteric. Inhibition of RAD51 multimerization, RAD51 interaction with another known interacting partner of RAD51 (e.g. BRCA2 or RAD51AP1), or RAD51 chelation/binding of Ca2+ ions may be accompanied by inhibition of RAD51 ATPase activity. Inhibition of RAD51 multimerization, RAD51 interaction with another known interacting partner of RAD51 (e.g. BRCA2 or RAD51AP1), or RAD51 chelation/binding of Ca2+ ions may be without inhibition of RAD51 ATPase activity.

In cells, compounds as disclosed herein can inhibit assembly of RAD51 filaments on DNA. In cells, compounds as disclosed herein can inhibit DNA damage repair. In cells, compounds as disclosed herein can inhibit cellular homologous recombination. In cells, compounds as disclosed herein can result in sensitization to genotoxic chemotherapeutics of cancer cells. In cells, compounds as disclosed herein can reduce drug resistance to chemotherapeutic agents, either through inhibition of DNA damage repair, or through inducing cellular stress through increase in intracellular free calcium concentration. In cells that depend on RAD51 overexpression, compounds as disclosed herein can result in cell death. In cells, compounds as disclosed herein may cause death in cellular conditions depending on RAD51 overexpression. In some embodiments, cells can be cancer cells or cells of patients with inheritable benign proliferative disorders (e.g. Cowden's syndrome). Further, any of the compounds disclosed herein can be used in combination with, for example, immuno-oncology agents or PARP inhibitors, or other chemotherapeutics for the purpose of inducing cell death.

The compounds disclosed herein can be used in methods of treatment of a disorder or condition where cell growth inhibition occurs by downregulation of homologous recombination, or where there is overexpression of proteins involved in the DNA damage repair pathway. The compounds disclosed herein can be used in methods of treatment of a disorder or condition associated with aberrant RAD51 activity.

The interface of RAD51 that can be targeted by a compound of the invention can be important for the control of the activity of the BRCA1/2 homologous recombination DNA repair pathway. Blocking of this interface important for the control of the activity of the BRCA1/2 homologous recombination DNA repair pathway with the compounds disclosed herein can have clinical relevance for several therapeutic indications.

Figure 3:
FIG. 3 shows cell killing of A549 cells by Compound 1 using an xCELLigence assay. The vertical line indicates the time of compound administration, and the cell index (Y-axis) represents cell viability
Figure 4:
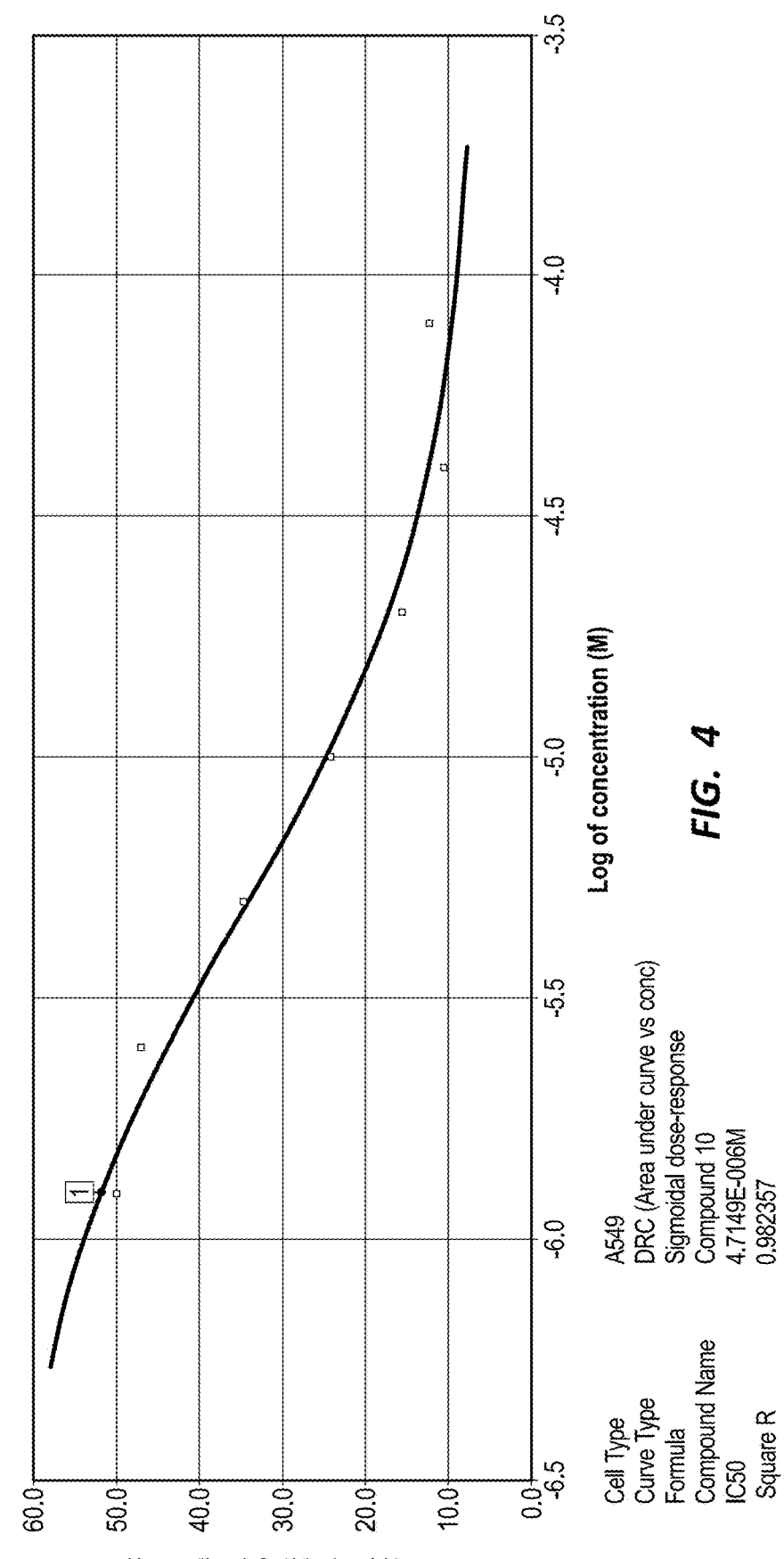
FIG. 4 shows an example of a curve fit to calculate the IC50 for Compound 1 based on the data shown in FIG. 3.

A compound disclosed herein can be used as a monotherapy for the treatment of, for example, intrahepatic cholangiocarcinoma (ICC), non-small cell lung cancer (NSCLC), metastatic castration-resistant prostate cancer (mCRPC), and other cancers that display upregulation of effectors of the RAD51/BRCA2 DNA damage repair pathway. The activity of compound 2 is demonstrated in FIG. 2, wherein NSCLC cells (A549) are shown treated and untreated with compound 2. Further demonstration of the acute kinetics of a compound 2 concentration gradient in A549 cells is shown in FIG. 3 where administration of compound causes rapid cell death (decrease in cell index). The subsequent IC50 analysis of FIG. 3 is shown in FIG. 4.

ICC cells can depend on the BRCA2 pathway for survival and render subjects untreatable. The inactivation of the homologous recombination pathway through RAD51 disrupting compounds can lead to cell death. This cell death can be selective for cells that depend on the BRCA2 pathway such as ICC cells. An example of this kind of selectivity is demonstrated in FIG. 5, wherein both primary fibroblasts and SSP25 cells (ICC-derived cells) are treated with compound 2 and little cell death is generated in the primary fibroblast cells compared to the SSP25 cells upon compound treatment In castration-resistant prostate cancers that overexpress the BRCA2 pathway, the inactivation of BRCA2 via inhibition of RAD51 disrupting compounds disclosed herein can lead to cell death. Several cancers exhibit upregulation of the homologous recombination pathway, specifically of RAD51 and BRCA2, which can render the cancer cells resistant to genotoxic chemotherapy. Cancers that spontaneously overexpress the RAD51/BRCA2 pathway components include, for example, hepatocellular carcinoma, acute myeloid leukemia (AML), aggressive mantle cell lymphoma, ovarian cancer, and imatinib-resistant BCR/ABL cancers.

The mechanism of action of the compounds disclosed herein can involve, for example, dislodging a pair of calcium ions coordinated by the RAD51 polymer in an acute manner leading to an acute intracellular free calcium concentration increase. The increase in the intracellular free calcium concentration can lead to cell death. This mechanism of cell death can occur in cells overexpressing the RAD51 protein, and the cell death can be orders of magnitude higher than cells without RAD51 overexpression. The cell death in cells contacted with compounds disclosed herein that overexpress the RAD51 protein may be at least 3, at least 10, at least 50, or at least 100 times greater than in cells contacted with compounds disclosed herein that do not overexpress RAD51. The sequestering of calcium ions by the RAD51 filaments to, for example, micromolar levels and the subsequent acute release of the pool of calcium ions into the cytosol upon compound binding can result in cell death in cancers dependent on the RAD51/BRCA2 pathway such as ICC and mCRPC. Evidence for this sequestration/release mechanism can be seen in FIGS. 6, 7 and 8, wherein the intracellular calcium chelators BAPTA-AM and Ruthenium red are able to counteract the cell-death inducing effects of compound 2, suggesting that the cell death mechanism of compound 2 involves the release of Ca2+ ions. Furthermore the intracellular calcium binding dye Fluo-2 shows accumulation in response to treatment with compound 2. This cell death can occur acutely in a few minutes and can be p53- and cell cycle-independent.

The mechanism of action of the compounds disclosed herein in cell death can involve inactivation of the recombination pathway through RAD51 alongside increases in cellular free calcium concentration. The mechanism of action of the compounds in cell death can involve increases in cellular free calcium concentration without inhibition of the recombination pathway through RAD51. The mechanism of action of the compounds in cell death can involve inhibition of RAD51 ATPase activity alongside increases in cellular free calcium concentration. The mechanism of action of the compounds in cell death can involve increases in cellular free calcium concentration without inhibition of RAD51 ATPase activity.

The compounds can also be used in the treatment of rare and orphan diseases including, for example, Bloom's syndrome, Fanconi Anemia, Werner's Syndrome, and Nijmegen Breakage Syndrome, which can display an increase in homologous recombination in their patients' cells.

The compounds can also be used in combination with other therapeutic agents including, for example, immuno-oncology agents, PARP inhibitors, and canonical chemotherapeutics. For example, metastatic melanoma patients who are responsive to anti-PD1 therapy can be highly enriched for somatic mutations in the BRCA2 gene within the patient tumors. This correlation can indicate that inactivation of the BRCA2 pathway sensitizes cells to anti-PD1 immunotherapy. The anti-PD1 agents can be, for example, nivolumab, pembrolizumab, or pidilizumab. PARP inhibitors can exhibit potent and selective activity against BRCA1 and BRCA2 mutated breast, ovarian, and other cancers. The use of a RAD51-disrupting compound can mimic the effects of a BRCA2 mutation and can potentially render a wider array of cancers treatable by PARP inhibitors. The PARP inhibitors can be, for example, olaparib, veliparib, niraparib, talazoparib, rucaparib, and CEP-9722.

A compound disclosed herein can be used in combination with other chemotherapeutic agents. The chemotherapeutic agents can include, for example, anti-PD1 agents, pembrolizumab, melphalan, doxorubicin, adrianmycin, etoposide, camptothecins, mitomycin C, cisplatin, oxaliplatin, carboplatin, or gemcitabine.

The compounds can be, for example, small molecules, biologics, antibodies, peptidomimetics, or peptides. The compound may be a peptide.

The compounds disclosed herein can harbor a cell penetration entity (CPP) or a protein transduction domain (PTD) to facilitate entry into the target cell. Protein transduction can refer to the delivery of peptides, proteins, and other molecules across cytoplasmic membranes into cells. The compounds can include at least one cell-penetration peptide (CPP) signal sequence. Examples of CPPs include HIV-TAT (GRKKRRQRRRPPQ) (SEQ ID NO: 4), R8 (RRRRRRRR) (SEQ ID NO: 8), MAP (KLALKLALKALKAALKLA) (SEQ ID NO: 137), transportan (GWTLNSAGYLLGKINL-KALAALAKKIL) (SEQ ID NO: 18), pegelin (RGGRL-SYSRRRFSTSTGR) (SEQ ID NO: 17), penetratin (RQIKIWFQNRRMKWKK) (SEQ ID NO: 7) and derivatives or combinations thereof. In some embodiments, the CPP or PTD is any of the sequences below in Table 1 or a combination thereof:

TABLE 1

Exemplary CPP Sequences

| Cell-penetrating peptide name | Amino acid sequence | SEQ ID NO: |
|---|---|---|
| AIP6 | RLRWR | 2 |
| DPV6 | GRPRESGKKRKRKRLKP | 3 |

TABLE 1-continued

Exemplary CPP Sequences

| Cell-penetrating peptide name | Amino acid sequence | SEQ ID NO: |
|---|---|---|
| HIV-1 TAT | GRKKRRQRRRPPQ | 4 |
| IRS-tag | RYIRS | 5 |
| Mini-penetratin | RRMKWKK | 6 |
| Penetratin | RQIKIWFQNRRMKWKK | 7 |
| Polyarginines | R8, R9, R10, R12 | 8, 131, 132, 134, respectively |
| R9F2C | RRRRRRRRRFFC | 9 |
| CADY | GLWRALWRLLRSLWRLLWRA | 10 |
| EB-1 | LIRLWSHLIHIWFQNRRLKWKKK | 11 |
| hCT | LGTYTQDFNKFHTFPQTAIGVGAP | 12 |
| PTD4 | YARAAARQARA | 13 |
| MAP | KLALKALKALKAALKLA | 14 |
| Pep-1 | KETWWETWWTEWSQPKKRKV | 15 |
| pVEC | LLIILRRRIRKQAHAHSK | 16 |
| SynB1 | RGGRLSYSRRRFSTSTGR | 17 |
| Transportan | GWTLNSAGYLLGKINLKALAALAKKIL | 18 |
| Vp1 | APKRKSGVSK | 19 |
| MAP17 | QLALQLALQALQAALQLA | 20 |
| PreS2 | PLSSIFSRIGDP | 21 |
| GALA | WEAALAEALAEALAEHLAEALAEALEALA A | 22 |
| MAP12 | LKTLTETLKELTKTLTEL | 23 |
| (PRR)n | (PRR)3, (PRR)4, (PRR)5, (PRR)6 | 24 and 142-144, respectively |
| (PPR)n | (PPR)3, (PPR)4, (PPR)5, (PPR)6 | 25, 145, 146, and 130, respectively |
| Bac-7 | RRIRPRPPRLPRPRPRPLPFPRPG | 26 |
| SAP | VRLPPPVRLPPPVRLPPP | 27 |
| SAP(E) | VELPPPVELPPPVELPPP | 28 |
| BIP | VPMLK(E) | 29 |
| C105Y | (CSIPPEVKFNK)PFVYLI | 30 |
| β3-integrin | VTVLALGALAGVGVG | 31 |
| K-FGF | AAVLLPVLLAAP | 32 |
| NF-κB | VQRKRQKLMP | 33 |
| Pep-7 | SDLWEMMMVSLACQY | 34 |
| β1-tail | YKSAVTTVVNPKYEGK | 35 |
| DPV1047 | VKRGLKLRHVRPRVTRMDV | 36 |
| M918 | MVTVLFRRLRIRRACGPPRVRV | 37 |

TABLE 1-continued

Exemplary CPP Sequences

| Cell-penetrating peptide name | Amino acid sequence | SEQ ID NO: |
|---|---|---|
| M1073 | MVRRFLVTLRIRRACGPPRVRV | 38 |
| BPrPr (1-28) | MVKSKIGSWILVLFVAMWSDVGLCKKRP | 39 |
| MPG | GALFLGFLGAAGSTMGAWSQPKKKRKV | 40 |
| p28 | LSTAADMQGVVTDGMASGLDKDYLKPDD | 41 |
| VT5 | DPKGDPKGVTVTVTVTVTGKGDPKPD | 42 |
| Bac 7 [(Bac(1-24)] | RRIRPRPPRLPRPRPRPLPFPRPG | 43 |
| CyLoP-1 | CRWRWKCCKK | 44 |
| gH 625 | GLASTLTRWAHYNALIRAF | 45 |
| CPP-C | PIEVCMYREP | 46 |
| SG3 | RLSGMNEVLSFRW | 47 |
| Pep-1 | KETWWETWWTEWSQPKKKRKV | 48 |
| Pept-1 | PLILLRLLRGQF | 49 |
| Pept-2 | PLIYLRLLRGQF | 50 |
| IVV-14 | KLWMRWYSPTTRRYG | 51 |
| Ig(v) | MGLGLHLLVLAAALQGAKKKRKV | 52 |
| HRSV | RRIPNRRPRR | 53 |
| cFΦR4 | cyclo(FΦRRRQ), Φ is 1-2-naphthylalanine | 54 |
| rrrrGy (SEQ ID NO: 148) | rrrrGy (SEQ ID NO: 148) | |
| rrrrrrr (SEQ ID NO: 147) | rrrrrrr (SEQ ID NO: 147) | |
| rrrrrGΦ (SEQ ID NO: 149) | rrrrrGΦ (SEQ ID NO: 149), Φ is 1-2-naphthylalanine | |
| rrrrrrrk(C6_5FAM) (SEQ ID NO: 150) | | |
| rrrrrr-sarcosine-sarcosine-OMe (SEQ ID NO: 151) | | |
| r(Ahx)r(Ahx)r(Ahx)r(Ahx)r (Ahx)r (SEQ ID NO: 152), or r(Ahx)r(Ahx)r(Ahx)r(Ahx)r (Ahx)r(Ahx)y (SEQ ID NO: 153) | | |

In the table, lower-case denotes D-amino acids and upper-case denotes L-amino acids. Amino acids are denoted by their conventional 1-letter codes, except where stated Any of the peptide compounds referred to herein can be N-terminally (e.g. alpha-amine) acetylated, C-terminally amidated, or backbone N-methylated. Any of the compounds referred to herein can be modified to include a 5FAM (Fluorescein amidite) label linked via a 6 carbon chain to the epsilon amino group of a lysine residue.

The peptides disclosed herein can also be stabilized by conversion to peptidomimetic entities. A peptidomimetic can be a polymer encompassing amino acid residues joined together through amide bonds. Such stabilization approaches can include, for example, cyclization to macrocycles, lactam esterification, N-methylation of the backbone residues, hydrocarbon stapling, usage of beta amino acids, and combinations thereof The peptides disclosed herein can be stabilized or modified by conversion to "retro-inverso" entities. Retro-inverso (or retro-inverse) peptides are peptides whose amino acid sequence is reversed and the alpha-carbon-center chirality of the amino acid subunits is inverted as well (e.g. L- to D- or D- to L-). Such a modification is known to increase stability of peptides when the original peptide is an (L)-peptide.

A compound of the invention can have, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acid residues. In some embodiments, a compound of the invention is not an antibody. In some embodiments, a compound of the invention is an antibody, or a functional binding fragment/derivative thereof (e.g. a Fab fragment or an ScFv). A compound of the invention can contain a RAD51 interacting motif with the following consensus sequence: R-L-G-L/M/V-S-R-R/L/K-R/F/V (SEQ ID NO.: 1). A compound of the invention can contain a targeting sequence (e.g. any of the Formulas in Table 1).

A compound of the invention can comprise, for example, a targeting sequence according to any one of the formulas in Table 2 below:

TABLE 2

| | Exemplary Targeting Sequences | SEQ ID NO |
|---|---|---|
| Formula I | L-$X_1$-R-$X_2$-V-R-L-R-$X_3$-$Y_1$-L-R-$X_4$<br>Or an invert thereof wherein:<br>$X_1$-$X_4$ and $Y_1$ are independently selected from the 20 natural L- or D-amino acids, or L- or D- isomers of Nle, Met(O), Met(O)2, Se-Met, Abu ($\alpha$-aminobutyric acid), Bal (Beta-Alanine), Hse, nme-Ser, and Ahx, and wherein L, R, and V are D- or L-amino acids. | 61 |
| Formula IA | Dan-Sar-L-$X_1$-R-$X_2$-V-R-L-R-$X_3$-$Y_1$-L-R-$X_4$<br>Or an invert thereof wherein:<br>$X_1$-$X_4$ and $Y_1$ are independently selected from the 20 natural L- or D-amino acids, or L- or D- isomers of Nle, Met(O), Met(O)2, Se-Met, Abu ($\alpha$-aminobutyric acid), Bal (Beta-Alanine), Hse, nme-Ser, and Ahx;<br>Dan is Dansyl, Sar is Sarcosine, and L, S, V, and R are L- or D-amino acids | 62 |
| Formula IB | L-$X_1$-R-$X_2$-V-R-L-R-$X_3$-G-L-R-$\Omega$<br>Or an invert thereof wherein:<br>$X_1$-X4 and $Y_1$ are independently selected from the 20 natural L- or D-amino acids, or L- or D- isomers of Nle, Met(O), Met(O)2, Se-Met, Abu ($\alpha$-aminobutyric acid), Bal (Beta-Alanine), Hse, nme-Ser, and Ahx<br>$\Omega$ is a cell-penetrating peptide sequence or an invert thereof; and wherein L, R and V are L- or D-amino acids. | 63 |
| Formula IC | L-$X_1$-R-$X_2$-V-R-L-R-$X_3$-G-L-R-$X_4$-Z-$\Omega$<br>Or an invert thereof wherein:<br>$X_1$-$X_4$ and $Y_1$ are independently selected from the 20 natural L- or D-amino acids, or L- or D- isomers of Nle, Met(O), Met(O)2, Se-Met, Abu ($\alpha$-aminobutyric acid), Bal (Beta-Alanine), Hse, nme-Ser, and Ahx<br>$\Omega$ is a cell-penetrating peptide sequence or a retro-invert thereof; and<br>Z is at least one neutral or hydrophilic amino acid selected from L- or D- Ser, Gly, Abu, Ala, Bal, Tyr, His, Thr, Pro and wherein L, R and V are L- or D-amino acids. | 64 |
| Formula II | L-$X_1$-R-$X_2$-V-R-L-R-$X_3$-$Y_1$-L<br>Or an invert thereof wherein :<br>$X_1$-$X_4$ and $Y_1$ are independently selected from the 20 common or L- or D- amino acids, or or L- or D-isomers of Nle, Met(O), Met(O)2, Se-Met, Abu ($\alpha$-aminobutyric acid), Bal (Beta-Alanine), Hse, nme-Ser, and Ahx, and wherein L, R, and V are L- or D-amino acids. | 65 |
| Formula III | $A_1$-$X_1$-$B_1$-$X_2$-C-$B_2$-$A_2$-$B_3$-$X_3$-D-$A_3$-$B_4$-$X_4$<br>Or an invert thereof wherein:<br>$A_1$-$A_3$ are independently selected from or L- or D- Leu, Nle, nme-Leu, Beta-HomoLeu, 5,5,5-Trifluoro-L-leucine, Ile, nme-Ile, Met, Met(O), Met(O)2, Se-Met, Val, Nva, and nme-Val;<br>B1-B4 are independently selected from or L- or D- Arg, Pra, Arg(Me), ADMA, SDMA, Ahx, Lys, and Lys-Ac;<br>C is selected from or L- or D- Val, Nva, and nme-Val;<br>D is selected from or L- or D- Gly and Beta-Ala;<br>$X_1$ is selected from or L- or D- Met, d-Nle, Met(O), Met(O)2, and Se-Met;<br>$X_2$ is selected from or L- or D- Ser, Abu ($\alpha$-aminobutyric acid), Bal (Beta-Alanine), Gly, Thr, Hse, and nme-Ser;<br>$X_3$ is selected from or L- or D- Val, Glu, d-Nle, Ile, Leu, and Met;<br>$X_4$ is selected from or L- or D-isomers Lys, Arg, Ahx. | |

Any of the polypeptides encompassed by Formula I, IA, TB, IC, II, or III (e.g. Table 1) can include one or more, 2 or more, 3 or more, 4 or more, 5 or more, 6 or more non-naturally occurring amino acids or (D)-amino acids. In some embodiments, the entire peptide is composed of D-amino acids or non-naturally occurring amino acids. The sequences may also be reversed in order. Thus, in some embodiments, the present disclosure includes a compound comprising Formula I, IA, IB, IC, II, or III (e.g. Table 1), wherein any one or more of the amino acids are optionally non-natural amino acids or (D)-amino acids.

In some aspects, the present disclosure provides for a non-naturally occurring peptide comprising a targeting motif of Formula I or an invert thereof:

(Formula I)

(SEQ ID NO: 61)

$$L-X_1-R-X_2-V-R-L-R-X_3-Y_1-L-R-X_4$$

wherein:

$X_1$-$X_4$ and $Y_1$ are independently selected from the 20 common or L- or D-amino acids, or L- or D-isomers of Nle, Met(O), Met(O)2, Se-Met, Abu (α-aminobutyric acid), Bal (Beta-Alanine), Hse, nme-Ser, and Ahx, wherein L, R, and V are or L- or D-amino acids.

In some embodiments for a compound of Formula I, at least one of $X_1$-$X_4$ and/or $Y_1$ is other than the 21 canonical amino acids. Such amino acids can include Nle, Met(O), Met(O)2, Se-Met, Abu (α-aminobutyric acid), Bal (Beta-Alanine), Hse, nme-Ser, and Ahx. In some embodiments, at least one of X1-X4 and/or Y1 is a non-natural amino acid. In some embodiments, X1 is a non-natural amino acid. In some embodiments, X2 is a non-natural amino acid. In some embodiments, X3 is a non-natural amino acid. In some embodiments, X4 is a non-natural amino acid. In some embodiments, Y1 is a non-natural amino acid. In some embodiments, X1 and X2 are non-natural amino acids. In some embodiments, X1 and X3 are non-natural amino acids. In some embodiments, X1 and X4 are non-natural amino acids. In some embodiments, X1 and Y1 are non-natural amino acids. In some embodiments, X2 and X3 are non-natural amino acids. In some embodiments, X2 and X4 are non-natural amino acids. In some embodiments, X2 and Y1 are non-natural amino acids. In some embodiments, X3 and X4 are non-natural amino acids. In some embodiments, X3 and Y1 are non-natural amino acids. In some embodiments, X4 and Y1 are non-natural amino acids. In some embodiments X1, X2, X3, X4, and Y1 are non-natural amino acids. In some embodiments X1, X3, X4, and Y1 are non-natural amino acids. In some embodiments X1, X2, X4, and Y1 are non-natural amino acids. In some embodiments X1, X2, X3, and Y1 are non-natural amino acids. In some embodiments X1, X2, X3, and X4 are non-natural amino acids. In some embodiments X2, X3, X4, and Y1 are non-natural amino acids. In some embodiments X1, X2, and X3 are non-natural amino acids. In some embodiments X2, X3, and X4 are non-natural amino acids. In some embodiments X3, X4, and Y1 are non-natural amino acids. In some embodiments X1, X3, and X4 are non-natural amino acids. In some embodiments X1, X3, and Y1 are non-natural amino acids. In some embodiments X1, X2, and X4 are non-natural amino acids. In some embodiments X1, X2, and Y1 are non-natural amino acids. In some embodiments X1, X4, and Y1 are non-natural amino acids.

In some embodiments for a compound of Formula I one of one of X1-X4 and/or Y1 is limited such that it does not comprise a particular amino acid. In some embodiments, X1 is not or L- or D-Met. In some embodiments, X2 is not or L- or D-Ser. In some embodiments, X3 is not L- or D-Val. In some embodiments, X4 is not L- or D-Lys. In some embodiments, Y1 is not L- or D-Gly. In some embodiments, X1 is not L- or D-Met, X2 is not L- or D-Ser, X3 is not L- or D-Val, X4 is not L- or D-Lys, and Y1 is not Gly. In some embodiments, X1 is not L- or D-Met and X2 is not L- or D-Ser. In some embodiments X1 is not L- or D-Met and X3 is not L- or D-Val. In some embodiments, X1 is not L- or D-Met and X4 is not L- or D-Lys. In some embodiments X1 is not L- or D-Met and Y1 is not Gly. In some embodiments X2 is not L- or D-Ser and X3 is not L- or D-Val. In some embodiments X2 is not L- or D-Ser and X4 is not L- or D-Lys. In some embodiments X2 is not L- or D-Ser and Y1 is not L- or D-Gly. In some embodiments X3 is not L- or D-Val and X4 is not L- or D-Lys. In some embodiments X3 is not L- or D-Val and Y1 is not Gly. In some embodiments, X1 is not L- or D-Met, X2 is not L- or D-Ser, and X3 is not L- or D-Val. In some embodiments X2 is not L- or D-Ser, X3 is not L- or D-Val, and X4 is not L- or D-Lys. In some embodiments X3 is not L- or D-Val, X4 is not L- or D-Lys, and Y1 is not Gly. In some embodiments X1 is not L- or D-Met, X3 is not L- or D-Val, and Y1 is not Gly. In some embodiments, X1 is not L- or D-Met, X2 is not L- or D-Ser, X3 is not L- or D-Val, and X4 is not L- or D-Lys. In some embodiments, X2 is not L- or D-Ser, X3 is not L- or D-Val, X4 is not L- or D-Lys, and Y1 is not Gly. In some embodiments, X1 is not L- or D-Met, X3 is not L- or D-Val, X4 is not L- or D-Lys, and Y1 is not Gly. In some embodiments, X1 is not L- or D-Met, X2 is not L- or D-Ser, X4 is not L- or D-Lys, and Y1 is not Gly. In some embodiments, X1 is not L- or D-Met, X2 is not L- or D-Ser, X3 is not L- or D-Val, and Y1 is not Gly. In some embodiments, X1 is not L- or D-Phe, X2 is not L- or D-Cys, and X3 is not L- or D-Glu.

In some embodiments, the peptide according to Formula I is according to Formula IA:

(Formula IA)

(SEQ ID NO: 62)

$$Dan-Sar-L-X_1-R-X_2-V-R-L-R-X_3-Y_1-L-R-X_4$$

Wherein $X_1$-$X_4$ and $Y_1$ are independently selected from the 20 common or L- or D-amino acids, or L- or D-isomers of Nle, Met(O), Met(O)2, Se-Met, Abu (α-aminobutyric acid), Bal (Beta-Alanine), Hse, nme-Ser, and Ahx; wherein Dan is Dansyl and Sar is Sarcosine, and wherein L, R and V are L- or D-amino acids.

In some embodiments, the peptide according to Formula I is according to Formula IA2:

$$L-X_1-R-X_2-V-R-L-R-X_3-Y_1-L-R-X_4-d-Ala-G$$

Wherein:

$X_1$-$X_4$ and $Y_1$ are independently selected from the 20 common L- or D-amino acids, or L- or D-isomers of Nle, Met(O), Met(O)2, Se-Met, Abu (α-aminobutyric acid), Bal (Beta-Alanine), Hse, nme-Ser, and Ahx.

In some embodiments, for a compound of Formula I, Y1 is restricted. In some embodiments, Y1 is L- or D-Bal or Gly. In some embodiments, Y1 is L- or D-Bal. In some embodiments, Y1 is Gly.

In some embodiments, for a compound of Formula I, X1, X2, X3, X4, or Y1 is restricted to a smaller subset of amino acids. In some embodiments, $X_1$ is a hydrophobic amino acid selected from L- or D-isomers of Val, Ile, Leu, Met, Phe, Trp, Cys, d-Nle, Met(O), Met(O)2, and Se-Met. In some embodiments, $X_1$ is L- or D-Val. In some embodiments, $X_1$ is L- or D-Ile. In some embodiments, $X_1$ is L- or D-Leu. In some embodiments, $X_1$ is L- or D-Met. In some embodiments, $X_1$ is L- or D-Phe. In some embodiments, $X_1$ is L- or D-Trp. In some embodiments, $X_1$ is L- or D-Cys. In some embodiments, $X_1$ is L- or D-Nle. In some embodiments, $X_1$ is L- or D-Met(O). In some embodiments, $X_1$ is L- or D-Met(O)2. In some embodiments, $X_1$ is L- or D-Se-Met. In some embodiments, $X_2$ is selected from a neutral or hydrophilic amino acid selected from L- or D-isomers of Ser, Gly, Abu, Ala, Bal, Tyr, His, Thr, and Pro. In some embodiments, $X_2$ is L- or D-Ser. In some embodiments, $X_2$ is Gly. In some embodiments, $X_2$ is L- or D-Abu. In some embodiments, $X_2$ is L- or D-Ala. In some embodiments, $X_2$ is L- or D-Bal. In some embodiments, $X_2$ is L- or D-Tyr. In some embodiments, $X_2$ is L- or D-His. In some embodiments, $X_2$ is L- or D-Thr. In some embodiments, $X_2$ is L- or D-Pro. In some embodiments, $X_3$ is selected from a neutral or hydrophilic amino acid selected from L- or D-isomers of Ser, Gly, Abu, Ala, Bal, Tyr, His, Thr, and Pro. In some embodiments, $X_3$ is L- or D-Ser. In some embodiments, $X_3$ is L- or D-Gly. In some embodiments, $X_3$ is L- or D-Abu. In some embodiments, $X_3$ is L- or D-Ala. In some embodiments, $X_3$ is L- or D-Bal. In some embodiments, $X_3$ is L- or D-Tyr. In some embodiments, $X_3$ is L- or D-His. In some embodiments, $X_3$ is L- or D-Thr. In some embodiments, $X_3$ is L- or D-Pro. In some embodiments, $X_4$ is a positively charged amino acid selected from L- or D-isomers of Lys, Arg, and Ahx. In some embodiments, $X_4$ is L- or D-Lys. In some embodiments, $X_4$ is L- or D-Arg. In some embodiments, $X_4$ is L- or D-Ahx. In some embodiments, $X_1$ is a hydrophobic amino acid selected from L- or D-isomers of Val, Ile, Leu, Met, Phe, Trp, Cys, d-Nle, Met(O), Met(O)2, and Se-Met and $X_2$ is selected from a neutral or hydrophilic amino acid selected from L- or D-isomers of Ser, Gly, Abu, Ala, Bal, Tyr, His, Thr, and Pro. In some embodiments, $X_4$ is L- or D-Ahx. In some embodiments, $X_1$ is a hydrophobic amino acid selected from L- or D-isomers of Val, Ile, Leu, Met, Phe, Trp, Cys, d-Nle, Met(O), Met(O)2, and Se-Met, $X_2$ is selected from a neutral or hydrophilic amino acid selected from L- or D-isomers of Ser, Gly, Abu, Ala, Bal, Tyr, His, Thr, and Pro, and $X_3$ is selected from a neutral or hydrophilic amino acid selected from L- or D-isomers of Ser, Gly, Abu, Ala, Bal, Tyr, His, Thr, and Pro. In some embodiments, $X_1$ is a hydrophobic amino acid selected from L- or D-isomers of Val, Ile, Leu, Met, Phe, Trp, Cys, d-Nle, Met(O), Met(O)2, and Se-Met, $X_2$ is selected from a neutral or hydrophilic amino acid selected from L- or D-isomers of Ser, Gly, Abu, Ala, Bal, Tyr, His, Thr, and Pro, $X_3$ is selected from a neutral or hydrophilic amino acid selected from L- or D-isomers of Ser, Gly, Abu, Ala, Bal, Tyr, His, Thr, and Pro, and $X_4$ is a positively charged amino acid selected from L- or D-isomers of Lys, Arg, and Ahx. In some embodiments, $X_1$ is a hydrophobic amino acid selected from L- or D-isomers of Val, Ile, Leu, Met, Phe, Trp, Cys, d-Nle, Met(O), Met(O)2, and Se-Met, $X_2$ is selected from a neutral or hydrophilic amino acid selected from L- or D-isomers of Ser, Gly, Abu, Ala, Bal, Tyr, His, Thr, and Pro, $X_3$ is selected from a neutral or hydrophilic amino acid selected from L- or D-isomers of Ser, Gly, Abu, Ala, Bal, Tyr, His, Thr, and Pro, and $X_4$ is a positively charged amino acid selected from L- or D-isomers of Lys, Arg, and Ahx. In some embodiments, $X_1$ is a hydrophobic amino acid selected from L- or D-isomers of Val, Ile, Leu, Met, Phe, Trp, Cys, d-Nle, Met(O), Met(O)2, and Se-Met, $X_3$ is selected from a neutral or hydrophilic amino acid selected from L- or D-isomers of Ser, Gly, Abu, Ala, Bal, Tyr, His, Thr, and Pro, and $X_4$ is a positively charged amino acid selected from L- or D-isomers of Lys, Arg, and Ahx. In some embodiments, $X_1$ is a hydrophobic amino acid selected from L- or D-isomers of Val, Ile, Leu, Met, Phe, Trp, Cys, d-Nle, Met(O), Met(O)2, and Se-Met, $X_2$ is selected from a neutral or hydrophilic amino acid selected from L- or D-isomers of Ser, Gly, Abu, Ala, Bal, Tyr, His, Thr, and Pro, and $X_4$ is a positively charged amino acid selected from L- or D-isomers of Lys, Arg, and Ahx. In some embodiments, $X_2$ is selected from a neutral or hydrophilic amino acid selected from L- or D-isomers of Ser, Gly, Abu, Ala, Bal, Tyr, His, Thr, and Pro, $X_3$ is selected from a neutral or hydrophilic amino acid selected from L- or D-isomers of Ser, Gly, Abu, Ala, Bal, Tyr, His, Thr, and Pro, and $X_4$ is a positively charged amino acid selected from L- or D-isomers of Lys, Arg, and Ahx. In some embodiments, $X_2$ is selected from a neutral or hydrophilic amino acid selected from L- or D-isomers of Ser, Gly, Abu, Ala, Bal, Tyr, His, Thr, and Pro, and $X_3$ is selected from a neutral or hydrophilic amino acid selected from L- or D-isomers of Ser, Gly, Abu, Ala, Bal, Tyr, His, Thr, and Pro. In some embodiments, $X_3$ is selected from a neutral or hydrophilic amino acid selected from L- or D-isomers of Ser, Gly, Abu, Ala, Bal, Tyr, His, Thr, and Pro, and $X_4$ is a positively charged amino acid selected from L- or D-isomers of Lys, Arg, and Ahx.

In some embodiments, for a compound of Formula I, X1, X2, X3, X4, or Y1 is restricted to a smaller subset of amino acids. In some embodiments, $X_1$ is selected from L- or D-isomers of Met, Val, and Nle. In some embodiments, $X_2$ is selected from L- or D-isomers of Ser, Gly, Abu, and Bal. In some embodiments, $X_3$ is selected from L- or D-isomers of Val and Nle. In some embodiments, $X_4$ is selected from L- or D-isomers of Lys, Arg, and Ahx. In some embodiments, $X_1$ is selected from L- or D-isomers of Met, Val, and Nle, $X_2$ is selected from L- or D-isomers of Ser, Gly, Abu, and Bal, $X_3$ is selected from L- or D-isomers of Val and d-Nle, and $X_4$ is selected from L- or D-isomers of Lys, Arg, and Ahx. In some embodiments, $X_1$ is selected from L- or D-isomers of Met, Val, and Nle, $X_3$ is selected from L- or D-isomers of Val and d-Nle, and $X_4$ is selected from L- or D-isomers of Lys, Arg, and Ahx. In some embodiments, $X_1$ is selected from L- or D-isomers of Met, Val, and Nle, $X_2$ is selected from L- or D-isomers of Ser, Gly, Abu, and Bal, and $X_4$ is selected from L- or D-isomers of Lys, Arg, and Ahx. In some embodiments, $X_1$ is selected from L- or D-isomers of Met, Val, and d-Nle, $X_2$ is selected from L- or D-isomers of Ser, Gly, Abu, and Bal, and $X_3$ is selected from L- or D-isomers of Val and Nle. In some embodiments, $X_1$ is selected from L- or D-isomers of Met, Val, and d-Nle and $X_2$ is selected from L- or D-isomers of Ser, Gly, Abu, and Bal. In some embodiments, $X_2$ is selected from L- or D-isomers of Ser, Gly, Abu, and Bal, and $X_3$ is selected from L- or D-isomers of Val and d-Nle. In some embodiments $X_3$ is selected from L- or D-isomers of Val and Nle, and $X_4$ is selected from L- or D-isomers of Lys, Arg, and Ahx. In some embodiments, $X_1$ is selected from L- or D-isomers of Met, Val, and Nle, and $X_3$ is selected from L- or D-isomers of Val and Nle. In some embodiments, $X_1$ is selected from Met, Val, and Nle, and $X_4$ is selected from L- or D-isomers of Lys, Arg, and Ahx. In some embodiments, $X_2$ is selected from L- or D-isomers of Ser, Gly, Abu, and Bal, $X_3$ is selected from L- or D-isomers of Val and Nle, and $X_4$ is selected from L- or D-isomers of Lys, Arg, and Ahx.

In some embodiments, for a peptide comprising a targeting sequence according to Formula I, the peptide comprises a cell-penetrating peptide motif. The cell-penetrating peptide motif can comprise any of the sequences outlined in Table 1 or a combination thereof (e.g. SEQ ID NO: 2-60), or a retro-invert thereof. In some embodiments, the cell-penetrating motif is C-terminal to the motif of Formula I. In some embodiments, the cell-penetrating motif is N-terminal to the motif of Formula I. In some embodiments, when the cell-penetrating motif is N-terminal to the motif of Formula I, the cell-penetrating motif overlaps with the first 1, 2 or 3 residues of Formula I. In some embodiments, the cell-penetrating peptide is AIP6, DPV6, HIV-1 TAT, IRS-tag, mini-penetratin, penetratin, $R_7$ (SEQ ID NO: 129), $R_8$ (SEQ ID NO: 8), $R_9$ (SEQ ID NO: 131), $R_{10}$ (SEQ ID NO: 132), $R_{11}$ (SEQ ID NO: 133), $R_{12}$ (SEQ ID NO: 134), R9F2C (SEQ ID NO: 135), cFΦR4 (SEQ ID NO: 54), CADY, EB-1, hCT, PTD4, MAP, Pep-1, pVEC, SynB1, Transportan, VP1, MAP17, PreS2, GALA, MAP12, $(PPR)_n$, $(PRR)_n$, Bac-7, SAP, BIP, C105Y, β3-integrin, K-FGF, NF-κB, Pep7, β1-tail, rrrrrr (SEQ ID NO: 147), rrrrr, rrrrrr (SEQ ID NO: 147), cFΦR4 (SEQ ID NO: 54), rrrrGy (SEQ ID NO: 148), rrrrrGΦ (SEQ ID NO: 149), rrrrrrrk(C6_5FAM) (SEQ ID NO: 150), rrrrrr-sarcosine-sarcosine-OMe (SEQ ID NO: 151), or r(Ahx)r(Ahx)r(Ahx)r(Ahx)r(Ahx)r (SEQ ID NO: 152), or r(Ahx)r(Ahx)r(Ahx)r(Ahx)r(Ahx)r(Ahx)y (SEQ ID NO: 153), or a retro-invert, or a combination thereof. In some embodiments, the cell-penetrating peptide is rrrrrr (SEQ ID NO: 147), rrrrr, rrrrrr (SEQ ID NO: 147), cFΦR4 (SEQ ID NO: 54), rrrrGy (SEQ ID NO: 148), rrrrrGΦ (SEQ ID NO: 149), rrrrrrrk(C6_5FAM) (SEQ ID NO: 150), rrrrrr-sarcosine-sarcosine-OMe (SEQ ID NO: 151), or r(Ahx)r(Ahx)r(Ahx)r(Ahx)r(Ahx)r (SEQ ID NO: 152), or r(Ahx)r(Ahx)r(Ahx)r(Ahx)r(Ahx)y (SEQ ID NO: 153), or a retro-invert, or a combination thereof.

In some embodiments, when the cell penetrating motif is N-terminal to the motif of Formula I, the cell-penetrating motif and the residues of Formula I are separated by at least 1, 2, 3, 4, 5, 6, 7, 8, 9, or 10 residues selected from Ala and Gly. In some embodiments, for a peptide according to Formula I, the peptide is according to Formula IB or IC or an invert thereof:

$$\text{(SEQ ID NO: 138)}$$
$$\text{L-}X_1\text{-R-}X_2\text{-V-R-L-R-}X_3\text{-G-L-R-}\Omega;$$
or $$\text{(Formula IC)}$$
$$\text{(SEQ ID NO: 139)}$$
$$\text{L-}X_1\text{-R-}X_2\text{-V-R-L-R-}X_3\text{-G-L-R-}X_4\text{-Z-}\Omega$$

wherein:

Ω is a cell-penetrating peptide sequence or a retro-invert thereof; and

Z is at least one neutral or hydrophilic amino acid selected from L- or D-Ser, Gly, Abu, Ala, Bal, Tyr, His, Thr, Pro, and wherein L, R, and V are L- or D-amino acids.

In some embodiments, for a peptide according to any of Formulas I, IA, IA2, IB, IC, II, or III or any of the compound structures herein (e.g. compounds 1-29), the peptide has particular functional characteristics. In some embodiments, the peptide inhibits RAD51 in vitro or in cells. In some embodiments, the peptide inhibits RAD51 noncompetitively with ATP. In some embodiments, the peptide inhibits RAD51 competitively with ATP. In some embodiments, the peptide induces death of mammalian cells having amplification of the RAD51 gene. In some embodiments, the peptide induces cell death in cells having amplification or overexpression of RAD51. In some embodiments, the cell death does not involve necroptosis or apoptosis. In some embodiments, the cell death comprises calcium-mediated cell death. Cells including amplification of RAD51 include a variety of cancerous cells and cell lines, including cell lines such as A549 and SSP25. In some embodiments, the IC50 for death induced by the compound when applied to a cell or cell line in vitro or in vivo harboring a RAD51 amplification is less than 250 μM, less than 100 μM, less than 50 μM, less than 25 μM, less than 10 μM, or less than 5 μM. In some embodiments, the IC50 of the compound in a hemolysis assay is greater than 250 μM. In some embodiments, the peptide has a half-life of greater than about 30 minutes when administered intraperitoneally or subcutaneously. In some embodiments, the peptide has a half-life of greater than about 7 minutes, greater than about 8 minutes, greater than about 9 minutes, greater than about 10 minutes, greater than about 11 minutes, greater than about 12 minutes, greater than about 13 minutes, greater than about 14 minutes, greater than about 15 minutes, greater than about 16 minutes, greater than about 17 minutes, greater than about 18 minutes, greater than about 19 minutes, greater than about 20 minutes, greater than about 21 minutes, greater than about 22 minutes, greater than about 23 minutes, greater than about 24 minutes, greater than about 25 minutes, greater than about 26 minutes, greater than about 27 minutes, greater than about 28 minutes, greater than about 29 minutes, or greater than about 30 minutes, when administered intravenously. In some embodiments, the peptide has half-life in a mouse serum stability assay of greater than 200 minutes. In some embodiments, the peptide has a half-life in a human or mouse microsome assay of greater than 30 minutes.

In some aspects, the present disclosure provides for a non-naturally occurring peptide comprising a targeting sequence according to Formula II or an invert thereof:

$$\text{(Formula II)}$$
$$\text{(SEQ ID NO: 136)}$$
$$\text{L-}X_1\text{-R-}X_2\text{-V-R-L-R-}X_3\text{-}Y_1\text{-L}$$

wherein:

$X_1$-$X_4$ and $Y_1$ are independently selected from the 20 common L- or D-amino acids, or L- or D-isomers of Nle, Met(O), Met(O)2, Se-Met, Abu (α-aminobutyric acid), Bal (Beta-Alanine), Hse, nme-Ser, and Ahx, and wherein L, R, and V are L- or D-amino acids.

In some embodiments, for a compound according to Formula II, $X_1$ is not L- or D-Phe, $X_2$ is not L- or D-Cys, and $X_3$ is not Glu.

In some embodiments, for a compound according to Formula II, at least one of $X_1$-$X_3$ and/or $Y_1$ is other than the 21 canonical L- or D-amino acids. Such amino acids can include L- or D-isomers of Nle, Met(O), Met(O)2, Se-Met, Abu (α-aminobutyric acid), Bal (Beta-Alanine), Hse, nme-Ser, and Ahx. In some embodiments, at least one of $X_1$-$X_3$ and/or $Y_1$ is a non-natural amino acid. In some embodiments, $X_1$ is a non-natural amino acid. In some embodiments, X2 is a non-natural amino acid. In some embodiments, X3 is a non-natural amino acid. In some embodiments, Y1 is a non-natural amino acid. In some embodiments, X1 and X2 are non-natural amino acids. In some embodiments, X1 and X3 are non-natural amino acids. In some embodiments, X1 and Y1 are non-natural amino acids. In some embodiments, X2 and X3 are non-natural amino acids. In some embodiments, X2 and Y1 are non-natural amino acids. In some embodiments, X3 and Y1 are non-natural amino acids. In some embodiments X1, X2, X3, and Y1 are non-natural amino acids. In some embodiments X1, X2, X3, and Y1 are non-natural amino acids. In some embodiments X1, X2, and X3 are non-natural amino acids. In some embodiments X1, X3, and Y1 are non-natural amino acids. In some embodiments X1, X2, and Y1 are non-natural amino acids.

In some embodiments for a compound of Formula II one of one of $X_1$-$X_3$ and/or $Y_1$ is limited such that it does not comprise a particular amino acid. In some embodiments, X1 is not L- or D-Met. In some embodiments, X2 is not L- or D-Ser. In some embodiments, X3 is not L- or D-Val. In some embodiments, X1 is not L- or D-Met and X2 is not L- or D-Ser. In some embodiments X1 is not L- or D-Met and X3 is not L- or D-Val. In some embodiments X1 is not L- or D-Met and Y1 is not Gly. In some embodiments X2 is not L- or D-Ser and X3 is not L- or D-Val. In some embodiments X2 is not L- or D-Ser and Y1 is not Gly. In some embodiments X3 is not L- or D-Val and Y1 is not L- or D-Gly. In some embodiments, X1 is not L- or D-Met, X2 is not L- or D-Ser, and X3 is not L- or D-Val. In some embodiments X1 is not L- or D-Met, X3 is not L- or D-Val, and Y1 is not Gly. In some embodiments, X1 is not L- or D-Met, X2 is not L- or D-Ser, X3 is not L- or D-Val, and Y1 is not Gly.

In some embodiments, the peptide according to Formula II is according to Formula IIA or an invert thereof:

```
(Formula IIA)
                                    (SEQ ID NO: 140)
Dan-Sar-L-X₁-R-X₂-V-R-L-R-X₃-Y₁-L
```

Wherein

X₁-X₃ and Y₁ are independently selected from the 20 common L- or D-amino acids, or L- or D-isomers of Nle, Met(O), Met(O)2, Se-Met, Abu (α-aminobutyric acid), Bal (Beta-Alanine), Hse, nme-Ser, and Ahx; wherein Dan is Dansyl and Sar is Sarcosine, and wherein L, V, S, and R are L- or D-amino acids.

In some embodiments, the peptide according to Formula II is according to Formula I:

```
(Formula I)
                                    (SEQ ID NO: 141)
L-X1-R-X2-V-R-L-R-X3-Y1-L-R-X4
``` wherein:

X1-X4 and Y1 are independently selected from the 20 common L- or D-amino acids, or L- or D-isomers of Nle, Met(O), Met(O)2, Se-Met, Abu (α-aminobutyric acid), Bal (Beta-Alanine), Hse, nme-Ser, and Ahx.

In some aspects, the present disclosure provides for a non-naturally occurring peptide comprising fewer than 100 amino acids, wherein the peptide comprises a targeting sequence according to Formula III or an invert thereof.

```
(Formula III)
A₁-X₁-B₁-X₂-C-B₂-A₂-B₃-X₃-D-A₃-B₄-X₄
``` wherein:

A₁-A3 are independently selected from L- or D-isomers of Leu, Nle, nme-Leu, Beta-HomoLeu, 5,5,5-Trifluoro-L-leucine, Ile, nme-Ile, Met, Met(O), Met(O)2, Se-Met, Val, Nva, and nme-Val;

B1-B4 are independently selected from L- or D-isomers of Arg, Pra, Arg(Me), ADMA, SDMA, Ahx, Lys, and Lys-Ac;

C is selected from L- or D-isomers of Val, Nva, and nme-Val;

D is selected from L- or D-isomers of Gly and Beta-Ala;

X₁ is selected from L- or D-isomers of Met, d-Nle, Met(O), Met(O)2, and Se-Met;

X₂ is selected from L- or D-isomers of Ser, Abu (α-aminobutyric acid), Bal (Beta-Alanine), Gly, Thr, Hse, and nme-Ser;

X₃ is selected from L- or D-isomers of Val, Glu, d-Nle, Ile, Leu, and Met;

X₄ is selected from L- or D-isomers of Lys, Arg, Ahx.

In some embodiments, for a compound of Formula III, at least one of $X_1$-$X_4$ and/or $Y_1$ is other than the 21 canonical L- or D-amino acids. Such amino acids can include L- or D-isomers of Nle, Met(O), Met(O)2, Se-Met, Abu (α-aminobutyric acid), Bal (Beta-Alanine), Hse, nme-Ser, and Ahx. In some embodiments, at least one of $X_1$-$X_4$ and/or $Y_1$ is a non-natural amino acid. In some embodiments, X1 is a non-natural amino acid. In some embodiments, X2 is a non-natural amino acid. In some embodiments, X3 is a non-natural amino acid. In some embodiments, X4 is a non-natural amino acid. In some embodiments, Y1 is a non-natural amino acid. In some embodiments, X1 and X2 are non-natural amino acids. In some embodiments, X1 and X3 are non-natural amino acids. In some embodiments, X1 and X4 are non-natural amino acids. In some embodiments, X1 and Y1 are non-natural amino acids. In some embodiments, X2 and X3 are non-natural amino acids. In some embodiments, X2 and X4 are non-natural amino acids. In some embodiments, X2 and Y1 are non-natural amino acids. In some embodiments, X3 and X4 are non-natural amino acids. In some embodiments, X3 and Y1 are non-natural amino acids. In some embodiments, X4 and Y1 are non-natural amino acids. In some embodiments X1, X2, X3, X4, and Y1 are non-natural amino acids. In some embodiments X1, X3, X4, and Y1 are non-natural amino acids. In some embodiments X1, X2, X4, and Y1 are non-natural amino acids. In some embodiments X1, X2, X3, and Y1 are non-natural amino acids. In some embodiments X1, X2, X3, and X4 are non-natural amino acids. In some embodiments X2, X3, X4, and Y1 are non-natural amino acids. In some embodiments X1, X2, and X3 are non-natural amino acids. In some embodiments X2, X3, and X4 are non-natural amino acids. In some embodiments X3, X4, and Y1 are non-natural amino acids. In some embodiments X1, X3, and X4 are non-natural amino acids. In some embodiments X1, X3, and Y1 are non-natural amino acids. In some embodiments X1, X2, and X4 are non-natural amino acids. In some embodiments X1, X2, and Y1 are non-natural amino acids. In some embodiments X1, X4, and Y1 are non-natural amino acids.

In some embodiments for a compound of Formula III one of one of X1-X4 and/or Y1 is limited such that it does not comprise a particular amino acid. In some embodiments, X1 is not L- or D-Phe, X2 is not L- or D-Cys, and X3 is not L- or D-Glu. In some embodiments, X1 is not L- or D-Met. In some embodiments, X2 is not L- or D-Ser. In some embodiments, X3 is not L- or D-Val. In some embodiments, X4 is not L- or D-Lys. In some embodiments, Y1 is not Gly. In some embodiments, X1 is not L- or D-Met, X2 is not L- or D-Ser, X3 is not L- or D-Val, X4 is not L- or D-Lys, and Y1 is not Gly. In some embodiments, X1 is not L- or D-Met and X2 is not L- or D-Ser. In some embodiments X1 is not L- or D-Met and X3 is not L- or D-Val. In some embodiments, X1 is not L- or D-Met and X4 is not L- or D-Lys. In some embodiments X1 is not L- or D-Met and Y1 is not L- or D-Gly. In some embodiments X2 is not L- or D-Ser and X3 is not L- or D-Val. In some embodiments X2 is not L- or D-Ser and X4 is not L- or D-Lys. In some embodiments X2 is not L- or D-Ser and Y1 is not Gly. In some embodiments X3 is not L- or D-Val and X4 is not L- or D-Lys. In some embodiments X3 is not L- or D-Val and Y1 is not Gly. In some embodiments, X1 is not L- or D-Met, X2 is not L- or D-Ser, and X3 is not L- or D-Val. In some embodiments X2 is not L- or D-Ser, X3 is not L- or D-Val, and X4 is not L- or D-Lys. In some embodiments X3 is not L- or D-Val, X4 is not L- or D-Lys, and Y1 is not Gly. In some embodiments X1 is not L- or D-Met, X3 is not L- or D-Val, and Y1 is not L- or D-Gly. In some embodiments, X1 is not L- or D-Met, X2 is not L- or D-Ser, X3 is not L- or D-Val, and X4 is not L- or D-Lys. In some embodiments, X2 is not L- or D-Ser, X3 is not L- or D-Val, X4 is not L- or D-Lys, and Y1 is not Gly. In some embodiments, X1 is not L- or D-Met, X3 is not L- or D-Val, X4 is not L- or D-Lys, and Y1 is not Gly. In some embodiments, X1 is not L- or D-Met, X2 is not L- or D-Ser, X4 is not L- or D-Lys, and Y1 is not Gly. In some embodiments, X1 is not L- or D-Met, X2 is not L- or D-Ser, X3 is not L- or D-Val, and Y1 is not Gly.

In some embodiments, for a compound according to Formula III, the peptide comprises fewer than 100, fewer than 90, fewer than 80, fewer than 70, fewer than 60, fewer than 50, fewer than 40, fewer than 30, or fewer than 20 amino acids.

In some embodiments, for a compound according to Formula III, one of A1-A3 is restricted to a single amino acid. In some embodiments, one of $A_1$-$A_3$ is L- or D-Leu. In some embodiments, A1 is L- or D-Leu. In some embodiments A2 is L- or D-Leu. In some embodiments, A3 is L- or D-Leu. In some embodiments, A1, A2, and A3 are L- or D-Leu. In some embodiments, A1 and A3 are L- or D-Leu. In some embodiments, A1, and A2 are L- or D-Leu.

In some embodiments, for a compound according to Formula III, one of B1-B4 is restricted to a single amino acid. In some embodiments, one of $B_1$-$B_4$ is L- or D-Arg. In some embodiments B1 is L- or D-Arg. In some embodiments B2 is L- or D-Arg. In some embodiments, B3 is L- or D-Arg. In some embodiments, B4 is L- or D-Arg. In some embodiments B1 is L- or D-Arg, B2 is L- or D-Arg, B3 is L- or D-Arg, and B4 is L- or D-Arg. In some embodiments B1 is L- or D-Arg, B2 is L- or D-Arg, and B4 is L- or D-Arg. In some embodiments B1 is L- or D-Arg, B3 is L- or D-Arg, and B4 is L- or D-Arg. In some embodiments B1 is L- or D-Arg, B2 is L- or D-Arg, and B3 is L- or D-Arg. In some embodiments B2 is L- or D-Arg, B3 is L- or D-Arg, and B4 is L- or D-Arg. In some embodiments B1 is L- or D-Arg and B3 is L- or D-Arg. In some embodiments B2 is L- or D-Arg and B4 is L- or D-Arg. In some embodiments B3 is L- or D-Arg and B4 is L- or D-Arg. In some embodiments B1 is L- or D-Arg and B4 is L- or D-Arg.

In some embodiments, for a compound according to Formula III, C is L- or D-Val. In some embodiments D is L- or D-Gly. In some embodiments, D is L- or D-Bal.

In some aspects, the present disclosure provides for a non-naturally occurring peptide provided below in Table 3:

| Compound # | CPP | core sequence | compound seq |
|---|---|---|---|
| 1 | rrrrrrr (SEQ ID NO: 147) | lmrsvrlrvGlrk (SEQ ID NO: 154) | Ac-lmrsvrlrvGlrkrrrrrrr-NH2 (SEQ ID NO: 155) |
| 2 | rrrrrrr (SEQ ID NO: 147) | lmrsqrlrqGlrk | Ac-lmrsqrlrqGlrkrrrrrrr-NH2 |
| 3 | cFΦR4 (SEQ ID NO: 54) | lmrsvrlrvGlrkaG (SEQ ID NO: 156) | Ac-lmrsvrlrvGlrkaG: : : (cFΦR4) |
| 4 | None | lmrsvrlrvGlrr (SEQ ID NO: 157) | Ac-lmrsvrlrvGlrr-NH2 (SEQ ID NO: 158) |
| 5 | rrrrrrrr | lvrsvGlrr | Ac-lvrsvGlrrrrrrrrr-NH2 |
| 6 | rrrrr | aGphlrkvralrslGlrlaq | Ac-rrrrraGphlrkvralrslGlrlaq-NH2 |
| 7 | rrrrrrrr | lGvsrvl | Ac-rrrrrrrrlGvsrvl-NH2 |
| 8 | rrrrrrr (SEQ ID NO: 147) | krlGvrlrvsrml (SEQ ID NO: 159) | Ac-rrrrrrrlGvrlrvsrml-NH2 (SEQ ID NO: 160) |
| 9 | rrrrrrr (SEQ ID NO: 147) | l{d-norLeucine} rsvrlrvGlrk (SEQ ID NO: 161) | Ac-l{d-norLeucine} rsvrlrvGlrkrrrrrrr-NH2 (SEQ ID NO: 162) |
| 10 | rrrrrrr (SEQ ID NO: 147) | l{d-norLeucine} rGvrlrvGlrk (SEQ ID NO: 163) | Ac-l{d-norLeucine} rGvrlrvGlrkrrrrrrr-NH2 (SEQ ID NO: 164) |
| 11 | rrrrGy (SEQ ID NO: 148) | l{d-norLeucine} rGvrlrvGlrk (SEQ ID NO: 163) | Ac-l{d-norLeucine} rGvrlrvGlrkrrrrGy-NH2 (SEQ ID NO: 165) |
| 12 | rrrrrGΦ (SEQ ID NO: 149) | l{d-norLeucine} rGvrlrvGlrk (SEQ ID NO: 163) | Ac-l{d-norLeucine} rGvrlrvGlrkrrrrrGΦ-NH2 (SEQ ID NO: 166) |
| 13 | rrrrrrrk(C6_5FAM) (SEQ ID NO: 150) | lmrsvrlrvGlrk (SEQ ID NO: 154) | Ac-lmrsvrlrvGlrkrrrrrrrk(C6_5FAM)-NH2 (SEQ ID NO: 167) |
| 14 | rrrrrGΦ (SEQ ID NO: 149) | l{d-norLeucine} rsrrlrvGlrk | Ac-l{d-norLeucine} rsrrlvrGlrkrrrrrGΦ-NH2 (SEQ ID NO: 168) |
| 15 | rrrrrGΦ (SEQ ID NO: 149) | l{d-norLeucine} r(abu)vrlrvGlrk (SEQ ID NO: 169) | Ac-l{d-norLeucine} r(abu)vrlrvGlrkrrrrrGΦ-NH2 (SEQ ID NO: 170) |

-continued

| Compound # | CPP | core sequence | compound seq |
|---|---|---|---|
| 16 | rrrrrGΦ (SEQ ID NO: 149) | l{d-norLeucine} rsvrl[d-norLeucine]Glrk (SEQ ID NO: 171) | Ac-l{d-norLeucine}rsvrlr [d-norLeucine]GlrkrrrrrGΦ-NH2 (SEQ ID NO: 172) |
| 17 | rrrrrGΦ (SEQ ID NO: 149) | l{d-norLeucine} rsvrlrv[beta-ALA]lrk (SEQ ID NO: 173) | Ac-l{d-norLeucine}rsvdrv [beta-ALA]lrkrrrrrGΦ-NH2 (SEQ ID NO: 174) |
| 18 | rrrrrGΦ (SEQ ID NO: 149) | l{d-norLeucine} r(abu)rrlr[d-norLeucine] [beta-ALA]lrk | Ac-l{d-norLeucine} r(abu)rrlr[d-norLeucine] [beta-ALA]lrkrrrrrGΦ-NH2 |
| 19 | rrrrr | DANSYL-Sarcosine- l{d-norLeucine}rsvrlrvGlrk (SEQ ID NO: 175) | DANSYL-Sarcosine- l{d-norLeucine}rsvrlrvGlrkrrrrr-NH2 |
| 20 | rrrrrr-sarcosine- sarcosine-OMe (SEQ ID NO: 151) | DANSYL-Sarcosine- l{d-norLeucine} rsvrlrvGlrr (SEQ ID NO: 176) | DANSYL-Sarcosine- l{d-norLeucine}rsvrlrvGlrrrrrr- sarcosine-sarcosine-OMe (SEQ ID NO: 177) |
| 21 | rrrrrr-sarcosine- sarcosine-OMe (SEQ ID NO: 151) | l{d-norLeucine} rsvrlrvGlrr (SEQ ID NO: 178) | Ac-l{d-norLeucine} rsvrlrvGlrrrrrr-sarcosine- sarcosine-OMe (SEQ ID NO: 179) |
| 22 | rrrrrGΦ (SEQ ID NO: 149) | l{d-norLeucine} r[beta-ALA]vrlrv[BETA-ALA]lrk (SEQ ID NO: 180) | Ac-l{d-norLeucine} r[beta-ALA]vrlrv[beta-ALA] lrkrrrrrGΦ-NH2 (SEQ ID NO: 181) |
| 23 | r(Ahx)r(Ahx)r(Ahx) r(Ahx)r(Ahx)r (SEQ ID NO: 152) | l{d-norLeucine} ravrlrv[beta-ALA]lr(Ahx) (SEQ ID NO: 182) | Ac-l{d-norLeucine}ravrlrv[beta-ALA] lr(Ahx)r(Ahx)r(Ahx)r(Ahx)r-NH2 (SEQ ID NO: 183) |
| 24 | r(Ahx)r(Ahx)r(Ahx) r(Ahx)r(Ahx)r(Ahx)y (SEQ ID NO: 153) | l{d-norLeucine} ravrlrv[beta-ALA]lr(Ahx) (SEQ ID NO: 182) | Ac-l{d-norLeucine}ravrlrv[beta-ALA] lr(Ahx)r(Ahx)r(Ahx)r(Ahx)r(Ahx)y- NH2 (SEQ ID NO: 184) |
| 25 | r(Ahx)r(Ahx)r(Ahx) r(Ahx)r(Ahx)r (SEQ ID NO: 152) | l{d-norLeucine} rsvrlvGlr(Ahx) (SEQ ID NO: 185) | Ac-l{d-norLeucine} rsvrlvGlr(Ahx)r(Ahx)r(Ahx)r(Ahx) r(Ahx)r-NH2 (SEQ ID NO: 186) |
| 26 | K(C6_5FAM)-rrrrrrr | krlGvrlrvsrml (SEQ ID NO: 159) | Ac-K(C6_5FAM)-rrrrrrrkrlGvrlrvsrml-NH2 |
| 27 | rrrrrGΦ (SEQ ID NO: 149) | EYE{Lys(Palm)}EYE{Ahx} V{Cit}{4-Abz}G{beta- ALA}l{d-norLeucine} rsvrlrv[beta-ALA]lrk (SEQ ID NO: 187) | Ac-EYE{Lys(Palm)}EYE{Ahx}V{Cit}{4-Abz} G{beta-ALA}l{d-norLeucine} rsvrlrv[beta-ALA]lrkrrrrrGΦ-NH2 (SEQ ID NO: 188) |
| 28 | rrrrrGΦ (SEQ ID NO: 149) | eeeeeeee(Ahx)-PLGLAG- l{d-norLeucine} r[beta-ALA] vrlrv[beta-ALA]lrk (SEQ ID NO: 189) | Suc-eeeeeeee(Ahx)-PLGLAG- l{d-norLeucine}r[beta-ALA]vrlrv [beta-ALA]lrkrrrrrGΦ-NH2 |
| 29 | rrRrrR-COOH | l{d-norLeucine} r[beta-ALA] vrlrv[beta-ALA]lr (SEQ ID NO: 190) | Ac-l{d-norLeucine}r[beta-ALA]vrlrv [beta-ALA]lrrrRrrR-COOH |

In some aspects, the present disclosure provides for a peptide comprising a targeting sequence selected from Table 4 below, or a retro-invert thereof. In some embodiments, the sequences are all D-amino acids. In some embodiments, the sequences are all L-amino acids. In some embodiments, the sequences are retro-inverts of the sequences in Table 4 below. In some embodiments, the peptide comprises multiple targeting sequences selected from Table 4 below. In some embodiments, the peptide comprises multiple repeats of the same sequence selected from Table 4 below. In some embodiments, the peptide comprises at least 1, 2, 3, 4, 5, 6, 7, 8, 9, or 10 sequences, repeats of the same sequence, or a combination thereof selected from Table 4 below. In some embodiments, the peptide further comprises a cell-penetrating peptide motif. The cell-penetrating peptide motif can comprise any of the sequences outlined in Table 1, a retro-invert thereof, or a combination thereof (e.g. SEQ ID NO: 2-60). In some embodiments, the sequences outlined in Table 1 comprise all L-amino acids. In some embodiments, the sequences outlined in Table 1 comprise all D-amino acids. In some embodiments, the cell-penetrating motif is C-terminal to the motif of Formula I. In some embodiments, the cell-penetrating motif is N-terminal to the motif of Formula I. In some embodiments, when the cell-penetrating motif is N-terminal to the motif of Formula I, the cell-penetrating motif overlaps with the first 1, 2 or 3 residues of Formula I. In some embodiments, the cell-penetrating peptide is AIP6, DPV6, HIV-1 TAT, IRS-tag, mini-penetratin, penetratin, $R_7$ (SEQ ID NO: 129), $R_8$ (SEQ ID NO: 8), $R_9$ (SEQ ID NO: 131), $R_{10}$ (SEQ ID NO: 132), $R_{11}$ (SEQ ID NO: 133), $R_{12}$ (SEQ ID NO: 134), R9F2C (SEQ ID NO: 135), cFΦR4 (SEQ ID NO: 54), CADY, EB-1, hCT, PTD4, MAP, Pep-1, pVEC, SynB1, Transportan, VP1, MAP17, PreS2, GALA, MAP12, $(PPR)_n$, $(PRR)_n$, Bac-7, SAP, BIP, C105Y, β3-integrin, K-FGF, NF-κB, Pep7, β1-tail, rrrrrrr (SEQ ID NO: 147), rrrrrr, rrrrrrr (SEQ ID NO: 147), cFΦR4 (SEQ ID NO: 54), rrrrGy (SEQ ID NO: 148), rrrrrGΦ (SEQ ID NO: 149), rrrrrrrk(C6_5FAM) (SEQ ID NO: 150), rrrrrr-sarcosine-sarcosine-OMe (SEQ ID NO: 151), or r(Ahx)r(Ahx)r(Ahx)r(Ahx)r(Ahx)r (SEQ ID NO: 152), or r(Ahx)r(Ahx)r(Ahx)r(Ahx)r(Ahx)y (SEQ ID NO: 153), a retro-invert thereof, or a combination thereof. In some embodiments, the cell-penetrating peptide is rrrrrrr (SEQ ID NO: 147), rrrrrr, rrrrrrr (SEQ ID NO: 147), cFΦR4 (SEQ ID NO: 54), rrrrGy (SEQ ID NO: 148), rrrrrGΦ (SEQ ID NO: 149), rrrrrrrk(C6_5FAM) (SEQ ID NO: 150), rrrrrr-sarcosine-sarcosine-OMe (SEQ ID NO: 151), or r(Ahx)r(Ahx)r(Ahx)r(Ahx)r(Ahx)r (SEQ ID NO: 152), or r(Ahx)r(Ahx)r(Ahx)r(Ahx)r(Ahx)y (SEQ ID NO: 153), a retro-invert thereof, or a combination thereof. In some embodiments, the peptide comprises fewer than 100, fewer than 80, fewer than 60, fewer than 40, fewer than 30, or fewer than 20 amino acids. In some embodiments, the stereochemistry of the amino acids of the targeting sequence and the amino acids of the cell-penetrating peptide motif are opposite stereochemistry (e.g D-vs L-isomers, or L- vs D-isomers). In some embodiments, the stereochemistry of the amino acids of the targeting sequence and the amino acids of the cell-penetrating peptide motif are the same stereochemistry (e.g. D- or L-isomers).

| Compound # | Targeting sequence |
|---|---|
| 1 | lmrsvrlrvGlrk (SEQ ID NO: 154) |
| 2 | lmrsqrlrqGlrk |
| 3 | lmrsvrlrvGlrkaG (SEQ ID NO: 156) |
| 4 | lmrsvrlrvGlrr (SEQ ID NO: 157) |
| 5 | lvrsvGlrr |
| 6 | aGphlrkvralrslGlrlaq |
| 7 | lGvsrvl |
| 8 | krlGvrlrvsrml (SEQ ID NO: 159) |
| 9 | l{d-norLeucine}rsvrlrvGlrk (SEQ ID NO: 161) |
| 10 | l{d-norLeucine}rGvrlrvGlrk (SEQ ID NO: 163) |
| 11 | l{d-norLeucine}rGvrlrvGlrk (SEQ ID NO: 163) |
| 12 | l{d-norLeucine}rGvrlrvGlrk (SEQ ID NO: 163) |
| 13 | lmrsvrlrvGlrk (SEQ ID NO: 154) |

32

-continued

| Compound # | Targeting sequence |
|---|---|
| 14 | l{d-norLeucine}rsrrlrvGlrk |
| 15 | l{d-norLeucine}r(abu)vrlrvGlrk (SEQ ID NO: 169) |
| 16 | l{d-norLeucine}rsvrlr[d-norLeucine]Glrk (SEQ ID NO: 171) |
| 17 | l{d-norLeucine}rsvrlrv[beta-ALA]lrk (SEQ ID NO: 173) |
| 18 | l{d-norLeucine}r(abu)rrlr[d-norLeucine][beta-ALA]lrk |
| 19 | DANSYL-Sarcosine-l{d-norLeucine}rsvrlrvGlrk (SEQ ID NO: 175) |
| 20 | DANSYL-Sarcosine-l{d-norLeucine}rsvrlrvGlrr (SEQ ID NO: 176) |
| 21 | l{d-norLeucine}rsvrlrvGlrr (SEQ ID NO: 178) |
| 22 | l{d-norLeucine}r[beta-ALA]vrlrv[beta-ALA]lrk (SEQ ID NO: 180) |
| 23 | l{d-norLeucine}ravrlrv[beta-ALA]lr(Ahx) (SEQ ID NO: 182) |
| 24 | l{d-norLeucine}ravrlrv[beta-ALA]lr(Ahx) (SEQ ID NO: 182) |
| 25 | l{d-norLeucine}rsvrlrvGlr(Ahx) (SEQ ID NO: 185) |
| 26 | krlGvrlrvsrml (SEQ ID NO: 159) |
| 27 | EYE{Lys(Palm)}EYE{Ahx}V{Cit}{4-Abz}G{beta-ALA}l{d-norLeucine}rsvrlrv[beta-ALA]lrk (SEQ ID NO: 187) |
| 28 | eeeeeeee(Ahx)-PLGLAG-l{d-norLeucine}r[beta-ALA]vrlrv[beta-ALA]lrk (SEQ ID NO: 189) |
| 29 | l{d-norLeucine}r[beta-ALA]vrlrv[beta-ALA]lr (SEQ ID NO: 190) |

The compounds disclosed herein can also include, for example, non-binding, negative control peptides that harbor point mutations. The negative control peptides would not disrupt the interaction between RAD51 and BRCA2, and can be used as experimental controls.

A compound disclosed herein can inhibit a protein-protein interaction by, for example, competitive or allosteric inhibition. A compound herein can bind a cellular target that is associated with, for example, the DNA damage repair pathway. The binding can cause a decrease in the deleterious effects of the mutated gene in the DNA damage repair pathway.

A compound disclosed herein can target the interaction between RAD51 and BRCA2 or RAD51AP1. The compound can inhibit the interaction between RAD51 and RAD51AP1.

The compound can be tested on cell lines that harbor resistant mutations, are programmed to become resistant to drugs or apoptosis, or have mutations specific to the DNA damage repair pathway. Cell lines that can be tested in a method disclosed herein include, for example, HEK-293T, H1299, HCT-116, MCF-7, U2OS, U251, U87, T98G, human GBM, A549 NSCLC, H1993, H2073, MES-SA, MES-SA/Dx5, HT1080, HeLa, Saos-2, IMR90, SSP25, PC3, LnCAP, Calu3, NciH1975, MDA MB 231, A375, and mouse embryonic fibroblasts (MEFs).

A compound disclosed herein can bind to a subregion of human RAD51. Human RAD51 can comprise the sequence:

```
                                      (SEQ ID NO.: 125)
MAMQMQLEANADTSVEEESFGPQPISRLEQCGINANDVKKLE

EAGFHTVEAVAYAPKKELINIKGISEAKADKILAEAAKLVPM

GFTTATEFHQRRSEIIQITTGSKELDKLLQGGIETGSITEMF

GEFRTGKTQICHTLAVTCQLPIDRGGGEGKAMYIDTEGTFRP

ERLLAVAERY GLSGSDVLDNVAYARAFNTDHQTQLLYQASA

MMVESRYALLIVDSATALYRTDYSGRGELSARQMHLARFLRM

LLRLADEFGVAVVITNQVVAQVDGAAMFAADPKKPIGGNIIA

HA STTRLYLRKGRGETRICKIYDSPCLPEAEAMFAINADGV

GDAKD.
```

A compound as disclosed herein can also interact with a subregion of a sequence at least 80 or at least 90 percent identical to human RAD51 (e.g. SEQ ID NO.: 125). A compound as disclosed herein can bind to RAD51AP1's binding site on RAD51. A compound as disclosed herein can bind within a subregion of human RAD51 (e.g. SEQ ID NO.: 125), wherein the subregion is amino acids 190-339 of human RAD51 (e.g. SEQ ID NO.: 125). A compound as disclosed herein can interact with a subregion of human RAD51 (e.g. SEQ ID NO.: 125), wherein the subregion is amino acids 190-218 of human RAD51 (e.g. SEQ ID NO.: 125). A compound as disclosed herein can interact with at least one of residues 202, 205, and 206 of human RAD51 (e.g. SEQ ID NO.: 125). A compound as disclosed herein can interact with at least two of residues 202, 205, and 206 of human RAD51 (e.g. SEQ ID NO.: 125). A compound as disclosed herein can interact with all three of residues 202, 205, and 206 of human RAD51 (e.g. SEQ ID NO.: 125). A compound as disclosed herein can interact with residue 187 of human RAD51 (e.g. SEQ ID NO.: 125). A compound as disclosed herein can interact with at least one of residues 187, 202, 205, and 206 of human RAD51 (e.g. SEQ ID NO.: 125). A compound as disclosed herein can interact with at least two of residues 187, 202, 205, and 206 of human RAD51 (e.g. SEQ ID NO.: 125). A compound as disclosed herein can interact with at least three of residues 187, 202, 205, and 206 of human RAD51 (e.g. SEQ ID NO.: 125). A compound as disclosed herein can interact with all four of residues 187, 202, 205, and 206 of human RAD51 (e.g. SEQ ID NO.:125).

Methods of Treatment

In some aspects, the present disclosure provides for a method of treating a malignancy or causing death of a cancer cell, comprising administering a compound according to any of Formulas I, IA, IA2, IB, IC, II, or III or any of the compounds recited herein (e.g. compounds 1-29). In some embodiments, the death of the cancer cell does not comprise necroptosis or apoptosis. In some embodiments, the death of the cancer cell comprises calcium-mediated cell death. In some embodiments, the compound comprises fewer than 100, fewer than 80, fewer than 60, fewer than 40, fewer than 30, or fewer than 20 amino acids. In some embodiments, the peptide is any of compounds 1-25.

In some embodiments, the method of treating a malignancy or causing death of a cancer cell comprises administering a peptide comprising a targeting sequence recited in Table 4. In some embodiments, the peptide further comprises a cell-penetrating peptide motif. The cell-penetrating peptide motif can comprise any of the sequences outlined in Table 1 or a combination thereof (e.g. SEQ ID NO: 2-60). In some embodiments, the cell-penetrating motif is C-terminal to the motif of Formula I. In some embodiments, the cell-penetrating motif is N-terminal to the motif of Formula I. In some embodiments, when the cell-penetrating motif is N-terminal to the motif of Formula I, the cell-penetrating motif overlaps with the first 1, 2 or 3 residues of Formula I. In some embodiments, the cell-penetrating peptide is AIP6, DPV6, HIV-1 TAT, IRS-tag, mini-penetratin, penetratin, $R_7$ (SEQ ID NO: 129), $R_8$ (SEQ ID NO: 8), $R_9$ (SEQ ID NO: 131), $R_{10}$ (SEQ ID NO: 132), $R_{11}$ (SEQ ID NO: 133), $R_{12}$ (SEQ ID NO: 134), R9F2C (SEQ ID NO: 135), cFΦR4 (SEQ ID NO: 54), CADY, EB-1, hCT, PTD4, MAP, Pep-1, pVEC, SynB1, Transportan, VP1, MAP17, PreS2, GALA, MAP12, $(PPR)_n$, $(PRR)_n$, Bac-7, SAP, BIP, C105Y, β3-integrin, K-FGF, NF-κB, Pep7, β1-tail, rrrrrr (SEQ ID NO: 147), rrrrrr, rrrrrrr (SEQ ID NO: 147), cFΦR4 (SEQ ID NO: 54), rrrrGy (SEQ ID NO: 148), rrrrrGΦ (SEQ ID NO: 149), rrrrrrk(C6_5FAM) (SEQ ID NO: 150), rrrrrr-sarcosine-sarcosine-OMe (SEQ ID NO: 151), or r(Ahx)r(Ahx)r(Ahx)r(Ahx)r(Ahx)r (SEQ ID NO: 152), or r(Ahx)r(Ahx)r(Ahx)r(Ahx)r(Ahx)r(Ahx)y (SEQ ID NO: 153), or a retro-invert thereof, or a combination thereof. In some embodiments, the cell-penetrating peptide is rrrrrrr (SEQ ID NO: 147), rrrrrr, rrrrrrr (SEQ ID NO: 147), cFΦR4 (SEQ ID NO: 54), rrrrGy (SEQ ID NO: 148), rrrrrGΦ (SEQ ID NO: 149), rrrrrrk (C6_5FAM) (SEQ ID NO: 150), rrrrrr-sarcosine-sarcosine-OMe (SEQ ID NO: 151), or r(Ahx)r(Ahx)r(Ahx)r(Ahx)r(Ahx)r (SEQ ID NO: 152), or r(Ahx)r(Ahx)r(Ahx)r(Ahx)r(Ahx)y (SEQ ID NO: 153), or a retro-invert thereof, or a combination thereof. In some embodiments, the peptide comprises fewer than 100, fewer than 80, fewer than 60, fewer than 40, fewer than 30, or fewer than 20 amino acids.

In some embodiments, the method of treating a malignancy or causing death of a cancer cell comprises administering any of the peptides described herein, wherein the peptide that has particular functional characteristics. In some embodiments, the peptide inhibits RAD51 in vitro or in cells. In some embodiments, the peptide inhibits RAD51 noncompetitively with ATP. In some embodiments, the peptide induces death of mammalian cells having amplification of the RAD51 gene. Cells including amplification of RAD51 include a variety of cancerous cells and cell lines, including cell lines such as A549 and SSP25. In some embodiments, the IC50 for death induced by the compound when applied to a cell or cell line in vitro or in vivo harboring a RAD51 amplification is less than 250 μM, less than 100 μM, less than 50 μM, less than 25 μM, less than 10 μM, or less than 5 μM. In some embodiments, the IC50 of the compound in a hemolysis assay is greater than 250 μM. In some embodiments, the peptide has a half-life of greater than about 30 minutes when administered intraperitoneally or subcutaneously. In some embodiments, the peptide has a half-life of greater than about 7 minutes, greater than about 8 minutes, greater than about 9 minutes, greater than about 10 minutes, greater than about 11 minutes, greater than about 12 minutes, greater than about 13 minutes, greater than about 14 minutes, greater than about 15 minutes, greater than about 16 minutes, greater than about 17 minutes, greater than about 18 minutes, greater than about 19 minutes, greater than about 20 minutes, greater than about 21 minutes, greater than about 22 minutes, greater than about 23 minutes, greater than about 24 minutes, greater than about 25 minutes, greater than about 26 minutes, greater than about 27 minutes, greater than about 28 minutes, greater than about 29 minutes, or greater than about 30 minutes, when administered intravenously. In some embodiments, the peptide has half-life in a mouse serum stability assay of greater than 200 minutes. In some embodiments, the peptide has a half-life in a human or mouse microsome assay of greater than 30 minutes.

In some embodiments, the method of treating a malignancy or causing death of a cancer cell comprises administering any of the peptides described herein, wherein the method exhibits reduced hemolysis.

In some embodiments, the method of treating a malignancy or causing death of a cancer cell comprises administering any of the peptides described herein, wherein the peptide is administered via a particular therapeutic route. In some embodiments, the peptide is administered intravenously. In some embodiments, the peptide is administered subcutaneously or intraperitoneally. In some embodiments, the peptide is administered orally.

In some embodiments, the method of treating a malignancy or causing death of a cancer cell comprises administering any of the peptides described herein, wherein the peptide is administered on a particular treatment schedule. In some embodiments, the compound is administered once daily. In some embodiments, the compound is administered once weekly.

Amino Acids.

Any of the compounds described herein can be include hydrophilic amino acids, hydrophobic amino acids, charged amino acids, uncharged amino acids, acidic amino acids, basic amino acids, neutral amino acids, aromatic amino acids, aliphatic amino acids, natural amino acids, non-natural amino acids, synthetic amino acids, artificial amino acids, capped amino acids, genetically-encoded amino acids, non-genetically encoded amino acids, and amino acid analogues, homologues, and congeners. A non-natural amino acid used in compounds described herein can be, for example, an amino acid that is prepared chemically or expressed by tRNA synthetase technology. A non-limiting example of an achiral amino acid that can be used in compounds described herein is glycine (G, Gly). Non-limiting examples of L-enantiomeric and D-enantiomeric amino acids that can be used in compounds described herein are: alanine (A, Ala); arginine (R, Arg); asparagine (N, Asn); aspartic acid (D, Asp); cysteine (C, Cys); glutamic acid (E, Glu); glutamine (Q, Gln); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); and valine (V, Val). In some embodiments, conservative or non-conservative substitutions of amino acids are possible of any compounds described herein.

Any of the compounds described herein can be modified by conservative amino acid substitution. Conservative amino acid substitutions involve the substitution of an amino acid with a chemically similar amino acid. Conservative substitution tables providing functionally similar amino acids are available from a variety of references (see, for e.g., Creighton, Proteins: Structures and Molecular Properties (W H Freeman & Co.; 2$^{nd}$ edition (December 1993)). The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

Non-natural amino acids can be substituted for natural/canonical amino acids in any of the compounds described herein, particularly when the non-natural amino acids have similar chemical properties (e.g. hydrophobicity, hydrophilicity). Non-natural amino acids are amino acids that are not D- or L-isomers of one of the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) or pyrolysine or selenocysteine; other terms that may be used synonymously with the term "non-natural amino acid" are "non-naturally encoded amino acid, "unnatural amino acid," "non-naturally-occurring amino acid," and variously hyphenated and non-hyphenated versions thereof. The term "non-natural amino acid" includes, but is not limited to, amino acids that occur naturally by modification of a naturally encoded amino acid (including but not limited to, the 20 common amino acids or pyrolysine and selenocysteine) but are not themselves incorporated into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine.

Non-natural amino acids include amino acid analogs. Amino acid analogs are compounds that have the same basic chemical structure as a naturally occurring amino acid, i.e., a central carbon that is bound to a hydrogen, a carboxyl group, an amino group, and an R group, such as, homoserine, homoarginine, norleucine, methionine sulfoxide, methionine methyl sulfonium. Such analogs have modified R groups (such as, norleucine) or modified peptide backbones, but retain the same basic chemical structure as a naturally occurring amino acid.

Non-natural amino acids include peptoid and beta amino-acid derivatives. Peptoids refer to poly-N-substituted glycines, a class of peptidomimetics whose side chains are appended to the nitrogen atom of the peptide backbone, rather than to the a-carbons (as in the 20 standard amino acids). Such analogs often have similar R groups, but a modified backbone (for examples, Sec-butylamine—NIle, Isobutylamine—NLeu, and Benzylamine—NPhe). Beta amino acids have their amino group bonded to the 3 carbon rather than the α carbon (as in the 20 standard amino acids). Examples of beta amino acids include beta-alanine, beta-valine and others.

Peptide Synthesis

Compounds as described herein can be synthetic peptides. Synthetic peptides were synthesized following standard solid-phase peptide synthesis protocols. The identity and purity of the peptides were confirmed and determined by RP-HPLC, MS/MS, and peptide content analysis. The trifluoroacetic acid (TFA) was exchanged for a non-toxic salt form (e.g. acetate or HCl) and the purity of the peptides was at least 95% before use in experiments.

Pharmaceutically-Acceptable Salts.

The invention provides the use of pharmaceutically-acceptable salts of any therapeutic compound disclosed herein.

Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Purity of Compounds.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56° A pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72° A pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88° A pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

In some embodiments, compounds of the invention can be applied topically to the skin, or a body cavity, for example, oral, vaginal, bladder, cranial, spinal, thoracic, or pelvic cavity of a subject. In some embodiments, the compounds of the invention can be applied to an accessible body cavity.

Compounds disclosed herein can increase cell death or inhibit cell growth in a cell by, for example, about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, about 15-fold, about 16-fold, about 17-fold, about 18-fold, about 19-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 85-fold, about 90-fold, about 95-fold, about 100-fold, about 110-fold, about 120-fold, about 130-fold, about 140-fold, about 150-fold, about 160-fold, about 170-fold, about 180-fold, about 190-fold, about 200-fold, about 250-fold, about 300-fold, about 350-fold, about 400-fold, about 450-fold, about 500-fold, about 550-fold, about 600-fold, about 650-fold, about 700-fold, about 750-fold, about 800-fold, about 850-fold, about 900-fold, about 950-fold, about 1000-fold, about 1500-fold, or about 2000-fold greater than when the cell is not exposed to the compound.

Compounds disclosed herein can increase free calcium concentration in a cell by, for example, about 2-fold, about 3-fold, about 4-fold, about 5-fold, about 6-fold, about 7-fold, about 8-fold, about 9-fold, about 10-fold, about 11-fold, about 12-fold, about 13-fold, about 14-fold, about 15-fold, about 16-fold, about 17-fold, about 18-fold, about 19-fold, or about 20-fold. Compounds disclosed herein can increase free calcium concentration in a cell by, for example, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold.

Compounds disclosed herein can display $GI_{50}$ values that are, for example, about 0.1 nM, about 0.2 nM, about 0.3 nM, about 0.4 nM, about 0.5 nM, about 0.6 nM, about 0.7 nM, about 0.8 nM, about 0.9 nM, about 1 nM, about 1.5 nM, about 2 nM, about 2.5 nM, about 3 nM, about 3.5 nM, about 4 nM, about 4.5 nM, about 5 nM, about 5.5 nM, about 6 nM, about 6.5 nM, about 7 nM, about 7.5 nM, about 8 nM, about 8.5 nM, about 9 nM, about 9.5 nM, about 10 nM, about 15 nM, about 20 nM, about 25 nM, about 30 nM, about 35 nM, about 40 nM, about 45 nM, about 50 nM, about 60 nM, about 70 nM, about 80 nM, about 90 nM, about 100 nM, about 110 nM, about 120 nM, about 130 nM, about 140 nM, about 150 nM, about 200 nM, about 250 nM, about 300 nM, about 350 nM, about 400 nM, about 450 nM, about 500 nm, about 600 nM, about 700 nM, about 800 nM, about 900 nM, about 1 μM, about 1.5 μM, about 2 μM, about 2.5 μM, about 3 μM, about 3.5 μM, about 4 μM, about 4.5 μM, about 5 μM, about 6 μM, about 7 μM, about 8 μM, about 9 μM, about 10 μM, about 15 μM, about 20 μM, about 25 μM, about 30 μM, about 35 μM, about 40 μM, about 45 μM, about 50 μM, about 60 μM, about 70 μM, about 80 μM, about 90 μM, about 100 μM, about 150 μM, about 200 μM, about 300 μM, about 400 μM, about 500 μM, about 600 μM, about 700 μM, about 800 μM, about 900 μM, or about 1 mM.

Compounds disclosed herein can be used to treat cancer in a subject. A compound disclosed herein can, for example, slow the proliferation of cancer cells, or kill cancer cells. Non-limiting examples of cancer that can be treated by a compound of the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom macroglobulinemia, and Wilms tumor.

Figure 10:
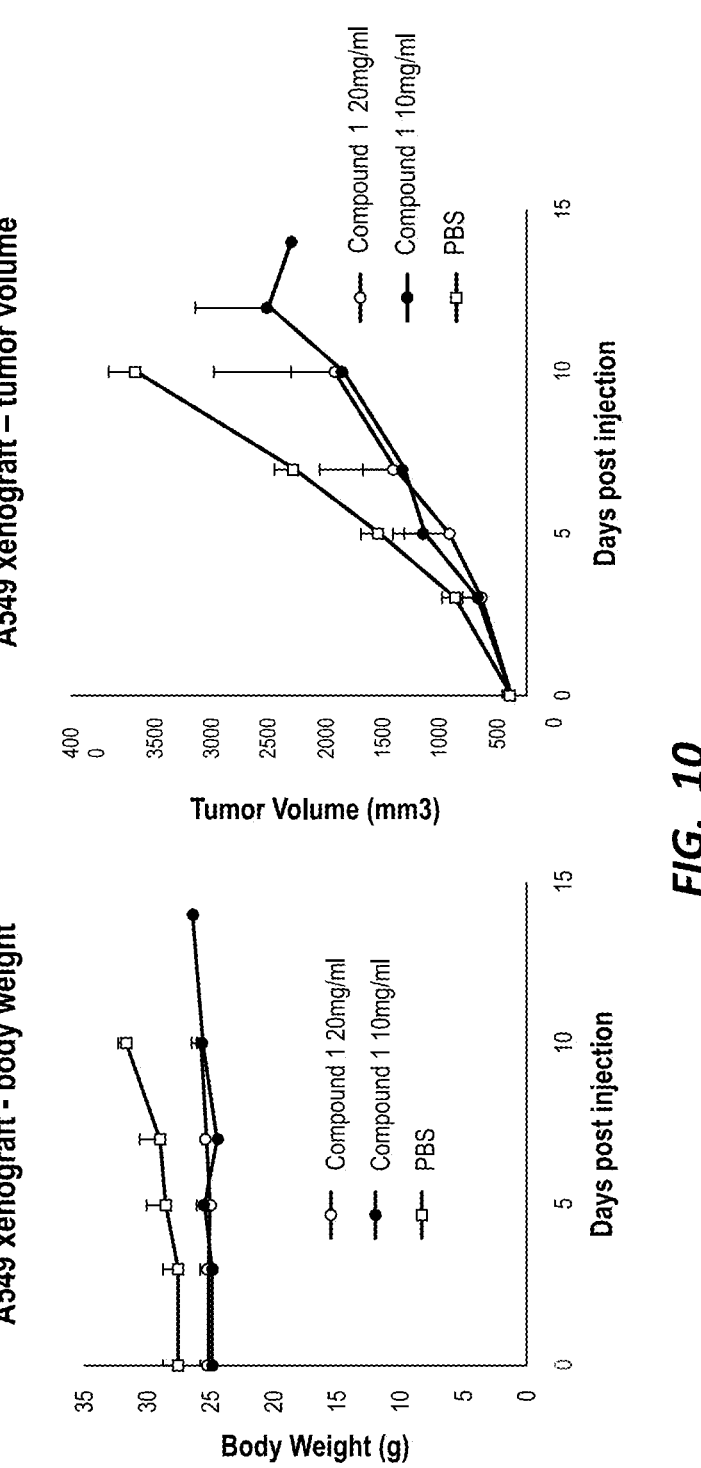
FIG. 10 shows the effect of Compound 1 administered intratumorally in an in vivo athymic mouse A549 xenograft model.
Figure 11:
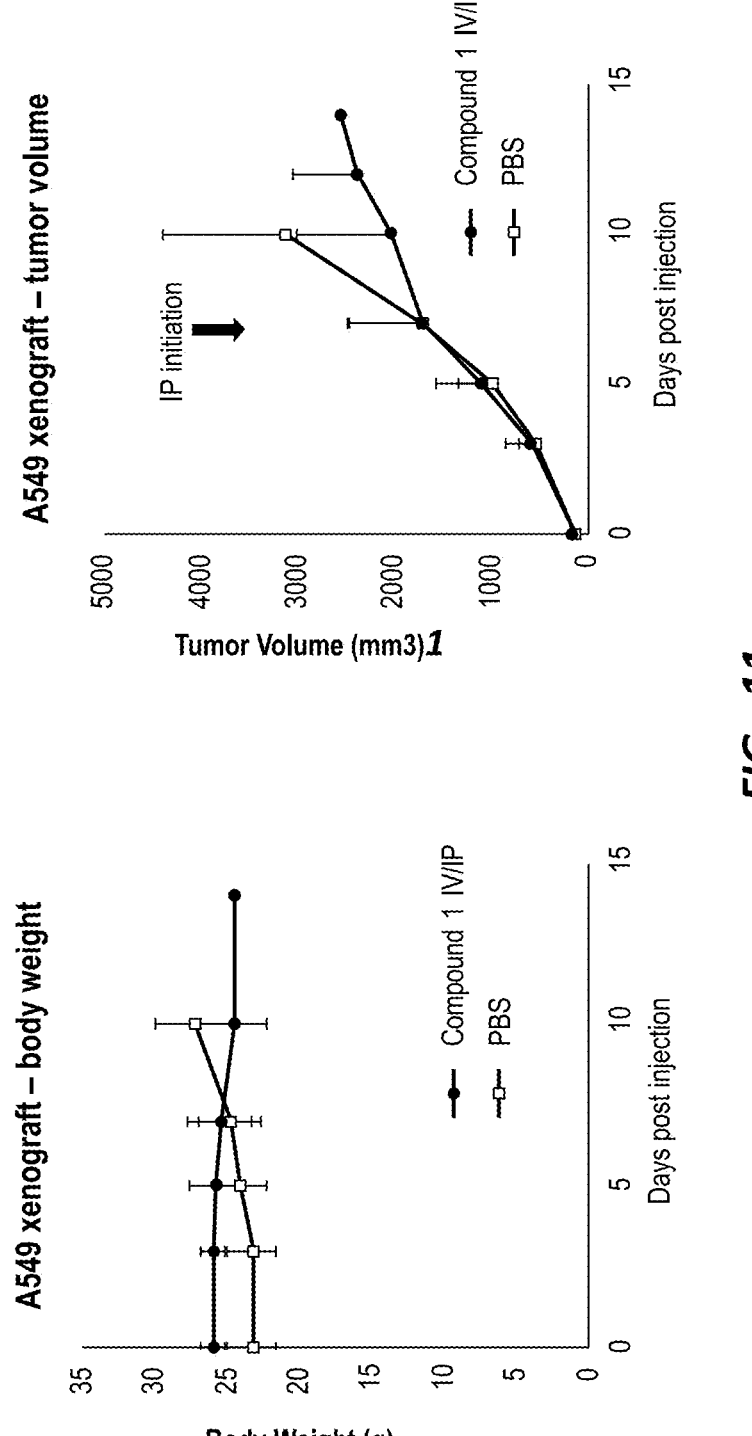
FIG. 11 shows the effect of Compound 1 administered intraperitoneally in an in vivo athymic mouse A549 xenograft model.
Figure 12:
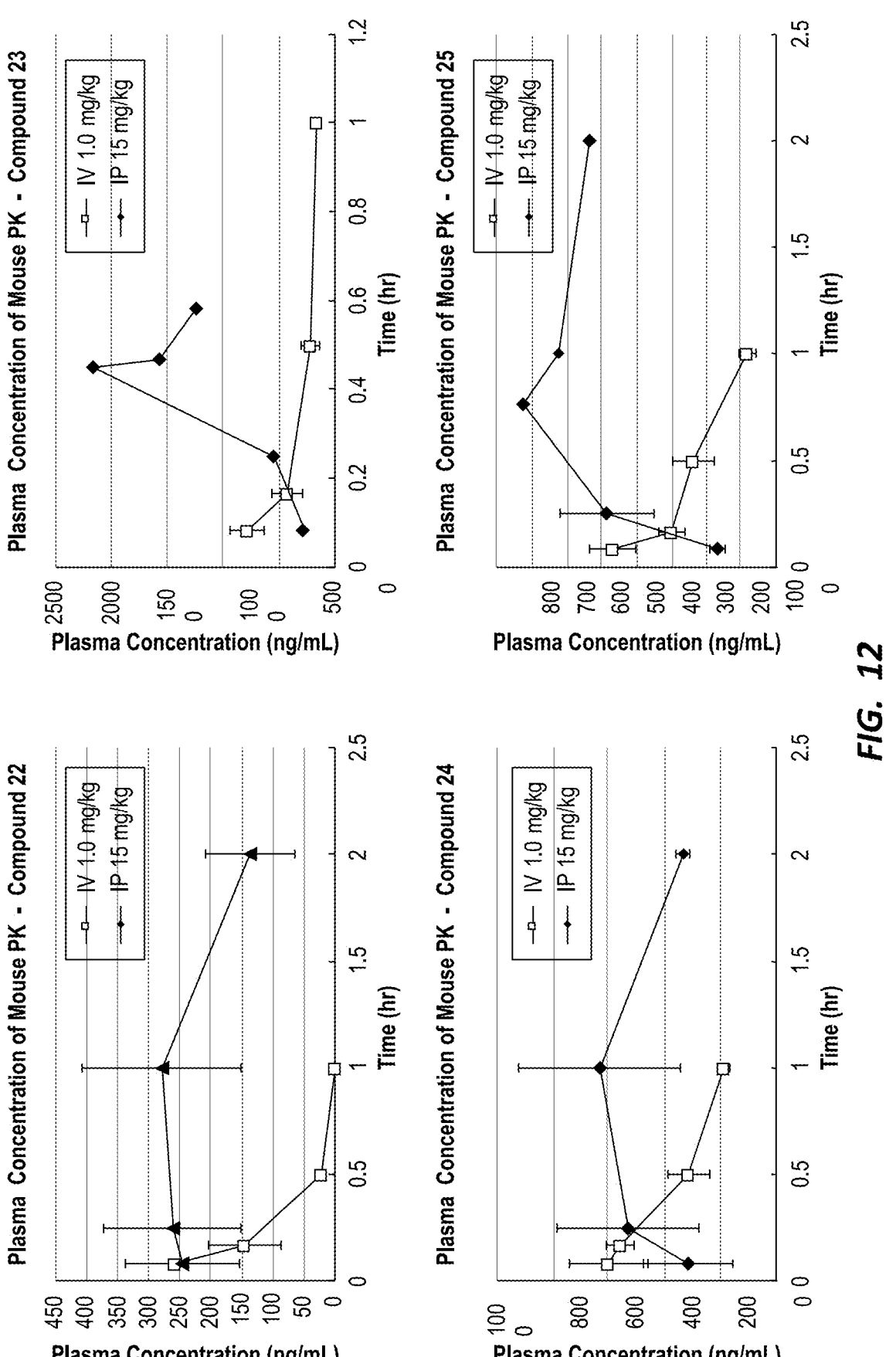
FIG. 12 depicts graphs for derivation of PK/PD parameters for the compounds in Tables 7 and 8 as in Example 7, showing compounds 22, 23, 24, and 25.

FIGS. 10 and 11 provide data showing suggestive cancer-related indications and administration methods for compounds according to the invention. FIG. 10 displays the activity of compound 1 in a xenograft model using A549 (a non-small cell lung cancer derived cell line), wherein compound 1 exhibits significant effects on tumor volume after only a few days of treatment when delivered intratumorally. FIG. 11 displays the activity of compound 1 delivered as an intraperitoneal injection after 1 week of tumor growth, in a single dose.

Cholangiocarcinoma, with an incidence of about 1-2 cases per 100,000, is a rare cancer characterized by mutated epithelial cells, which originate in the bile ducts. Cholangiocarcinoma can be characterized as intrahepatic, perihilar, or distal bile duct cancer. Intrahepatic cholangiocarcinoma is a form of a cholangiocarcinoma that occurs within the bile ducts of the liver. The cancer in the bile duct can lead to the blockage of bile ducts and the accumulation of bilirubin. The major symptoms of cholangiocarcinoma include, for example, abnormal liver function tests, abdominal discomfort, jaundice, weight loss, pruritus, fever, loss of appetite, and changes in color of stool or urine.

Risk factors for cholangiocarcinoma include, for example, chronic inflammation or dysfunction of the bile ducts. Dysfunction of the bile ducts can manifest as, for example, primary sclerosing cholangitis, bile duct stones, choledochal cysts, liver fluke infections, polycystic liver disease, Caroli syndrome, cirrhosis, hepatitis B infection, or hepatitis C infection. Mutations in BRCA1/BRCA2 can also cause cholangiocarcinoma. Liver flukes are parasites that are commonly found in Asian countries in raw or poorly cooked fish. Other risk factors for cholangiocarcinoma include, for example, inflammatory bowel disease, age, obesity, exposure to thorium dioxide, diabetes, smoking, pancreatitis, HIV infection, asbestos exposure, or radon exposure.

Treatment for cholangiocarcinoma can include, for example, curative surgery, palliative surgery, laparoscopic procedures, external beam radiation therapy, three-dimensional conformal radiation therapy, intensity-modulated radiation therapy, stereotactic body radiotherapy, brachytherapy, 5-fluorouracil (5-FU), gemcitabine, cisplatin, capecitabine, or oxaliplatin.

In metastatic castration-resistant prostate cancer (CRPC), despite castrate levels of androgens, the androgen receptor (AR) remains active and drives cancer progression. The major symptoms of early stage prostate cancer include, for example, difficulty urinating, painful urination, frequent urination, hematuria, or pelvic pain. Prostate cancer often metastasizes to the bone and lymph nodes.

Hormone-dependent prostate cancer can become resistant to treatment after one to three years of therapy. Treatment for CRPC, includes, for example, anti-mitotic chemotherapeutics, docetaxel, cabazitaxel, bevacizumab, thalidomide, prednisone, sipuleucel-T, abiraterone, enzalutamide, or any combination thereof.

Pancreatic cancer arises when cells in the pancreas begin to multiply out of control and form a mass, which can metastasize to other parts of the body. The major symptoms of pancreatic cancer include, for example, upper abdominal pain, back pain, jaundice, loss of appetite, weight loss, and blood clots. Exocrine cancer can be, for example, pancreatic adenocarcinoma, acinar cell carcinoma, cystadenocarcinoma, pancreatoblastoma, adenosquamous carcinoma, signet ring cell carcinoma, hepatoid carcinoma, colloid carcinoma and pancreatic mucinous cystic neoplasm. Pancreatic neuroendocrine tumors (PanNETs) can arise elsewhere in the pancreas. Treatment of pancreatic cancer can include, for example, surgical removal of the pancreas or the affected region of the pancreas, chemotherapy, 5-fluorouracil, gemcitabine, erlotinib, nab-paclitaxel, folic acid, irinotecan, oxaliplatin, FOLFIRINOX regimen, octreotide, lanreotide, everolimus, sunitinib, radiation therapy, or any combination thereof Small-cell carcinoma arises in the lungs, and can be highly malignant. Small-cell carcinoma is a neuroendocrine carcinoma that can exhibit aggressive behavior, rapid growth, early spread to distant sites, sensitivity to chemotherapy and radiation, and frequent association with distinct paraneoplastic syndromes, including, for example, hypercalcemia, Eaton-lambert syndrome, or syndrome of inappropriate diuretic hormone. Symptoms of small-cell carcinoma can include, for example, cough, dyspnea, weight loss, and frailty. Treatment for small-cell carcinoma can include, for example, cyclophosphamide, cisplatin, doxorubicin, etoposide, vincristine, paclitaxel, radiation therapy, or any combination thereof Compounds disclosed herein can be used to treat Bloom's syndrome in a subject. Bloom's syndrome is a rare autosomal recessive genetic disorder caused by a mutation in the BLM gene, which encodes for a DNA helicase enzyme. Cells for subjects afflicted with Bloom's syndrome exhibit marked chromosomal instability leading to increased sensitivity to UV radiation and higher risk for cancer. The features of Bloom's syndrome include, for example, unusually small stature, sparse fat tissue, high-pitched voice, long and narrow face, prominent nose, prominent ears, sun sensitivity, skin rash upon exposure to the sun, hypopigmentation, hyperpigmentation, reduced fertility in women, infertility in men, increased risk for diabetes, and chronic obstructive pulmonary disease, mild immune system abnormalities, and a shortened life expectancy.

Subjects can be, for example, elderly adults, adults, adolescents, pre-adolescents, children, toddlers, infants, and non-human animals. In some embodiments, a subject is a patient.

Pharmaceutical Compositions.

A pharmaceutical composition disclosed herein can be used, for example, before, during, or after treatment of a subject with another pharmaceutical agent.

A pharmaceutical composition disclosed herein can be a combination of any pharmaceutical compounds disclosed herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N, N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds disclosed herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compound disclosed herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds disclosed herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof A composition can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound disclosed herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Multiple therapeutic agents can be administered in any order or simultaneously. In some embodiments, a compound of the invention is administered in combination with, before, or after an antibiotic. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents disclosed herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A therapeutic agent can be administered as soon as is practicable after the onset of a disease or condition is detected or suspected, and for a length of time necessary for the treatment of the disease, such as, for example, from about 1 month to about 3 months. The length of treatment can vary for each subject.

Pharmaceutical compositions disclosed herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

EXAMPLES

Example 1: Treatment of A549 Cells (NSCLC) with Compounds Disclosed Herein

Figure 2:
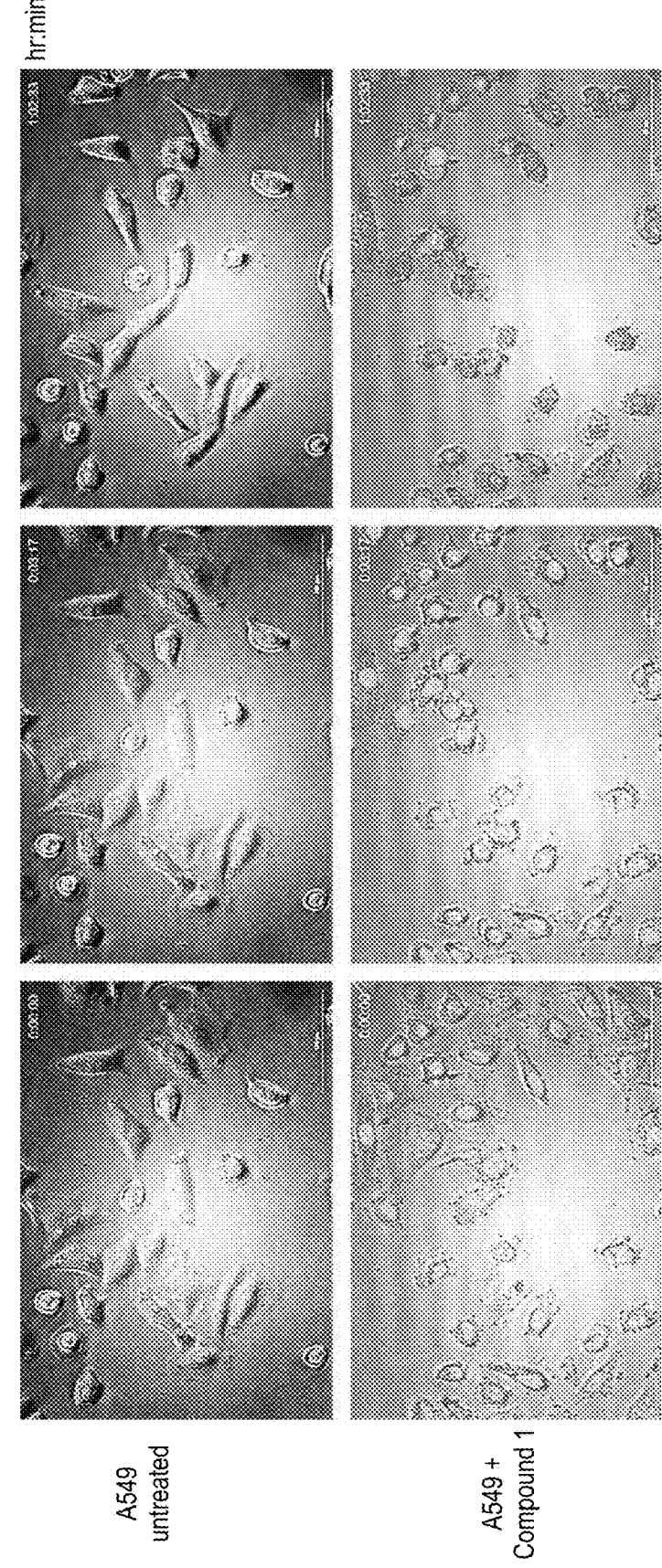
FIG. 2 shows untreated A549 cells and cells treated with Compound 1 imaged in parallel using a Cytation instrument. DAPI was used to mark the nuclei and timepoints are shown as indicated.

To assess the growth inhibitory properties of compounds disclosed herein, 10 µM of Compound 1 was tested against a PBS mock treatment for growth of A549 cells using microscopy at the indicated timepoints shown in the top right corner of each panel of FIG. 2. FIG. 3 shows that Compound 1 had a dose-dependent effect on the growth of A549 cells displaying acute cell death kinetics as measured by an xCELLigence™ instrument. First, 5,000 A549 cells were plated, and adherence and growth was measured for 20 hours using live measurements of current impedance through the plate using the xCELLigence™ instrument. At the 25 hour mark, a concentration gradient of Compound 1 or a PBS control was added to the A549 cells, which were cultured in 100 µL DMEM media with 10% FBS. Acute death kinetics were observed in real time and the cells were allowed to keep growing. The concentration gradient was used for IC50 value calculation as shown in FIG. 4.

Example 2: Selective Killing of Cells

Figure 5:
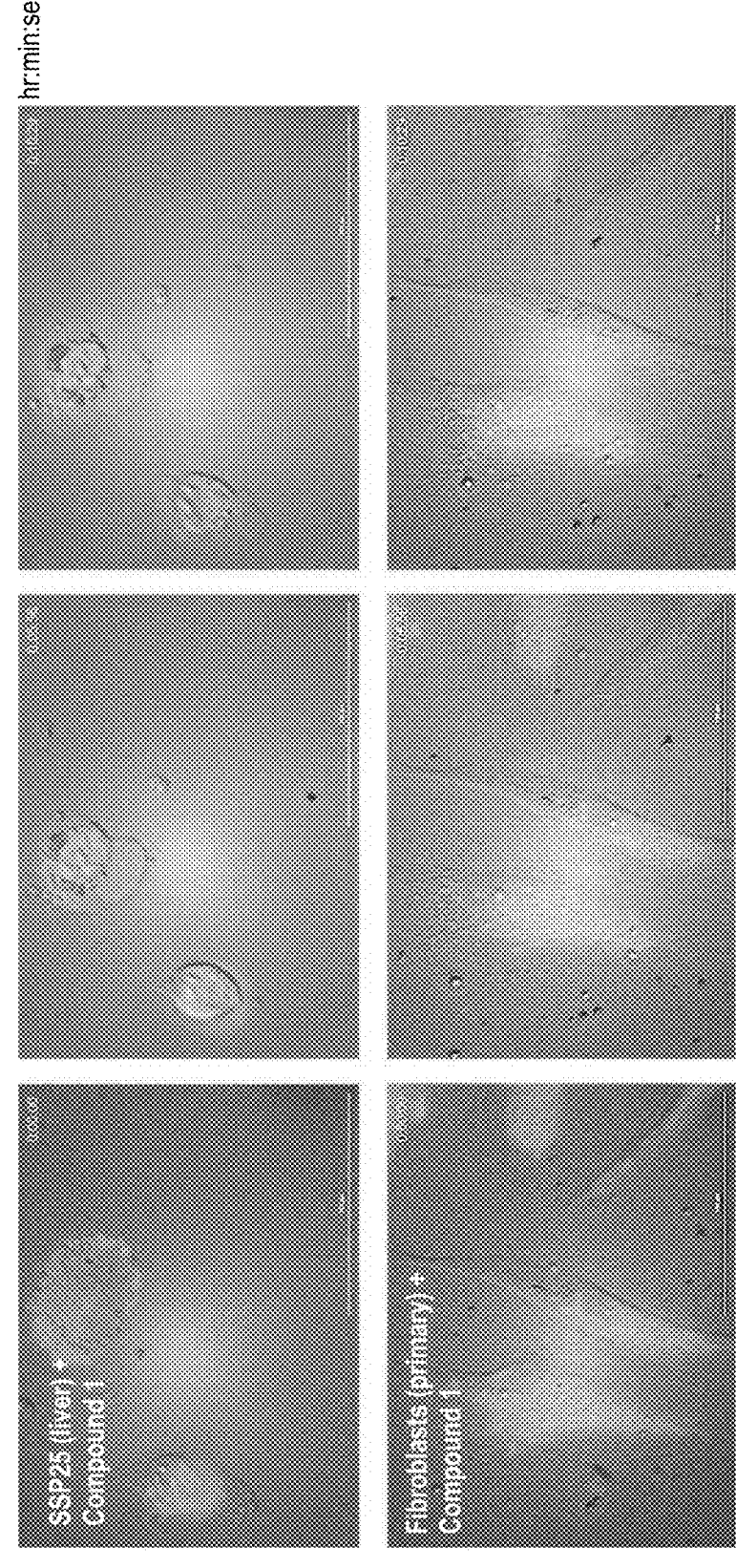
FIG. 5 shows primary fibroblasts and SSP25 cells both treated with Compound 1 imaged in parallel using a Cytation instrument. DAPI was used to mark the nuclei, mitotracker red was used to track mitochondria, and timepoints are shown as indicated.

To assess the specificity of compounds disclosed herein in targeting cancers with overexpression of RAD51, Compound 1 was tested against primary fibroblasts and SSP25 cells (cholangiocarcinoma cell line) (FIG. 5). First, 5,000 cells were incubated in 96-well culture plates overnight. Cells were grown in DMEM or RPMI, respectively, with 10% FBS, and compound 2 was added to a concentration of 10 µM and imaging commenced using a Cytation™ instrument using approximately 5 minute time points. DAPI was used to visualize the nuclei and mitotracker-red was used to observe mitochondria. Cell morphology was seen to be drastically affected in SSP25 cells and not in the primary fibroblasts. Furthermore, cell morphology was affected within 5 minutes of imaging, and the macrobubble phenotype was stable for further periods of time.

Example 3: Intracellular Ca2+ Chelation
Suppresses the Cytotoxicity of Compound 2 in
SSP25 Cells To investigate the hypothesis that peptide treatment of cells causes cell death via increases in intracellular free calcium levels, Compound 1 alone and in combination with two different intracellular calcium chelators (1,2-Bis(2-aminophenoxy)ethane-N,N,N',N'-tetraacetic acid tetrakis(acetoxymethyl ester) aka "BAPTA-AM", and ammoniated ruthenium oxychloride aka "ruthenium red") was tested in an xCELLigence™ cell death assay as in Example 1. The intracellular calcium chelators alone were also evaluated on the cells. In both cases, administration of calcium chelators rescues cell death, suggesting that compounds herein kill cells as a result of a rise in intracellular free Ca2+ ions, and that counteracting the rise in intracellular free Ca2+ ions prevents cell death due to the compounds.

Figure 6:
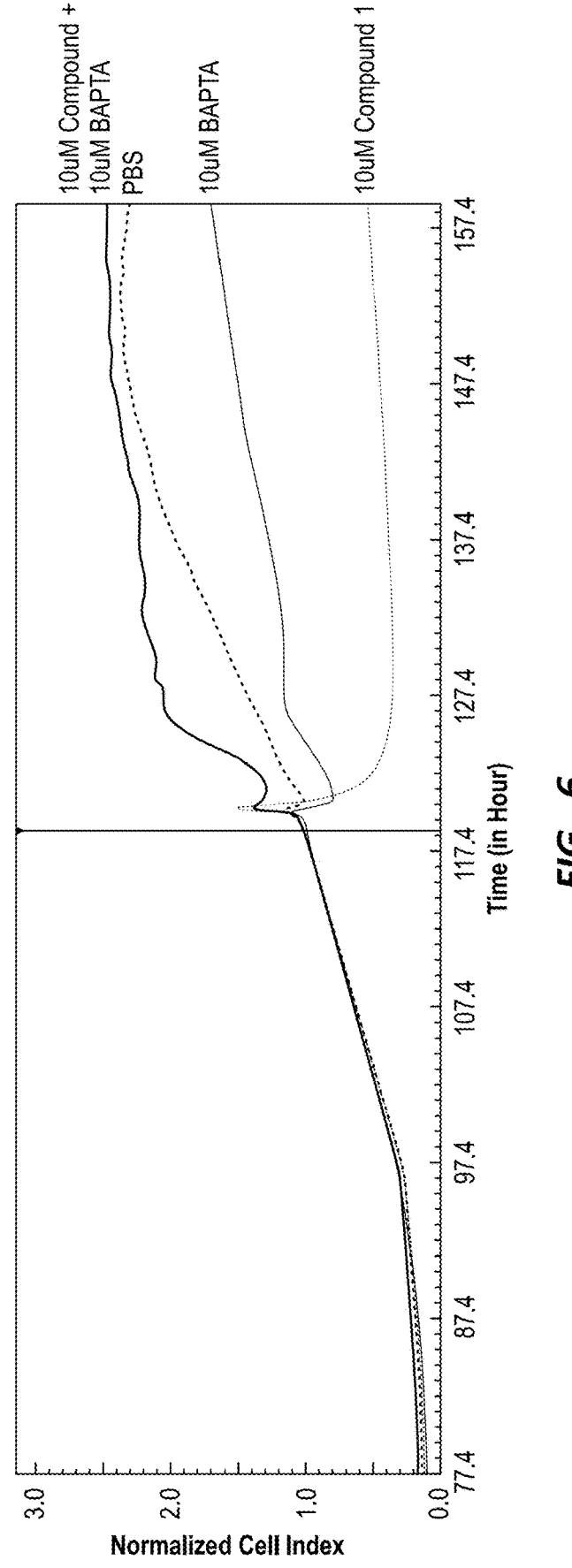
FIG. 6 shows an xCELLigence cell death assay on SSP25 cells, wherein Compound 1 is added alone or combined with the calcium chelator BAPTA-AM, demonstrating that addition of BAPTA-AM rescues cell death due to Compound 1.

FIG. 6 demonstrates that addition of 10 µM BAPTA-AM to cells treated with 10 µM Compound 1 rescues cell death relative to compound alone (see curves in FIG. 6, where the curve representing the BAPTA-AM+compound combination is roughly equivalent to PBS alone, while the curves representing compound 2 alone displays significant cell death).

Figure 7:
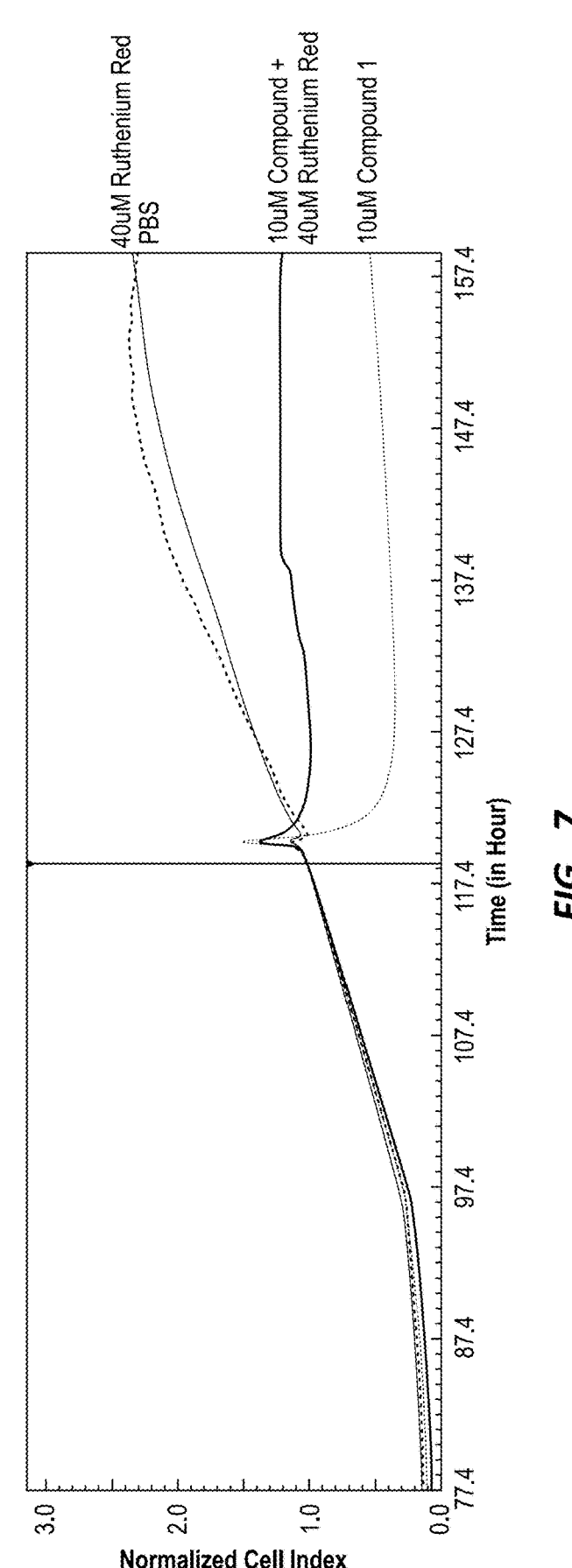
FIG. 7 shows an xCELLigence cell death assay on SSP25 cells, wherein Compound 1 is added alone or combined with the calcium chelator ruthenium red, demonstrating that addition of ruthenium red rescues cell death due to Compound 1.

FIG. 7 demonstrates that addition of 40 µM Ruthenium red to cells treated with 10 µM Compound 1 rescues cell death relative to compound alone (see curves in FIG. 7, where the curve representing the ruthenium red+compound combination is roughly equivalent to PBS alone, while the curve representing compound alone displays significant cell death).

Figure 8:
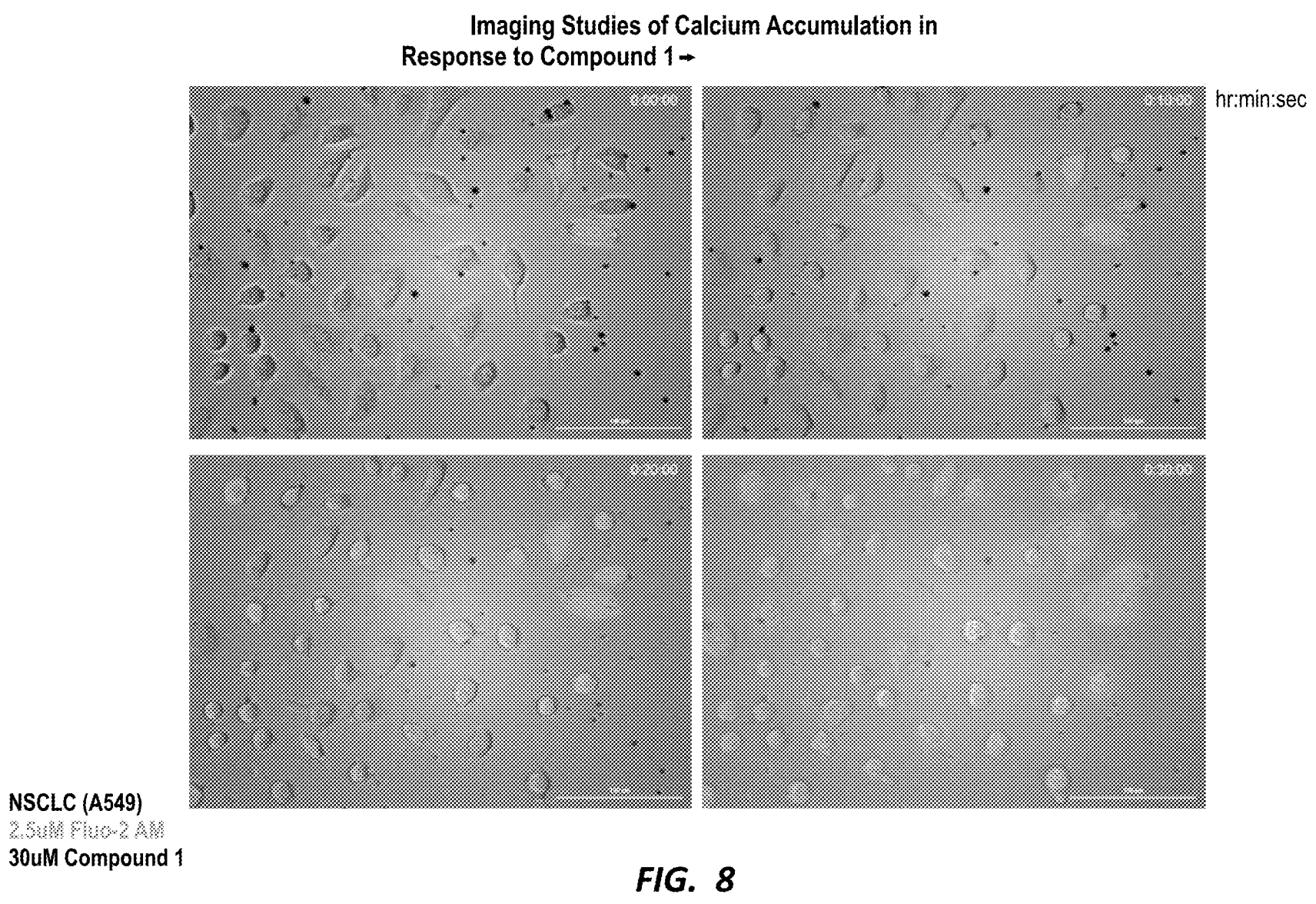
Figure 9:
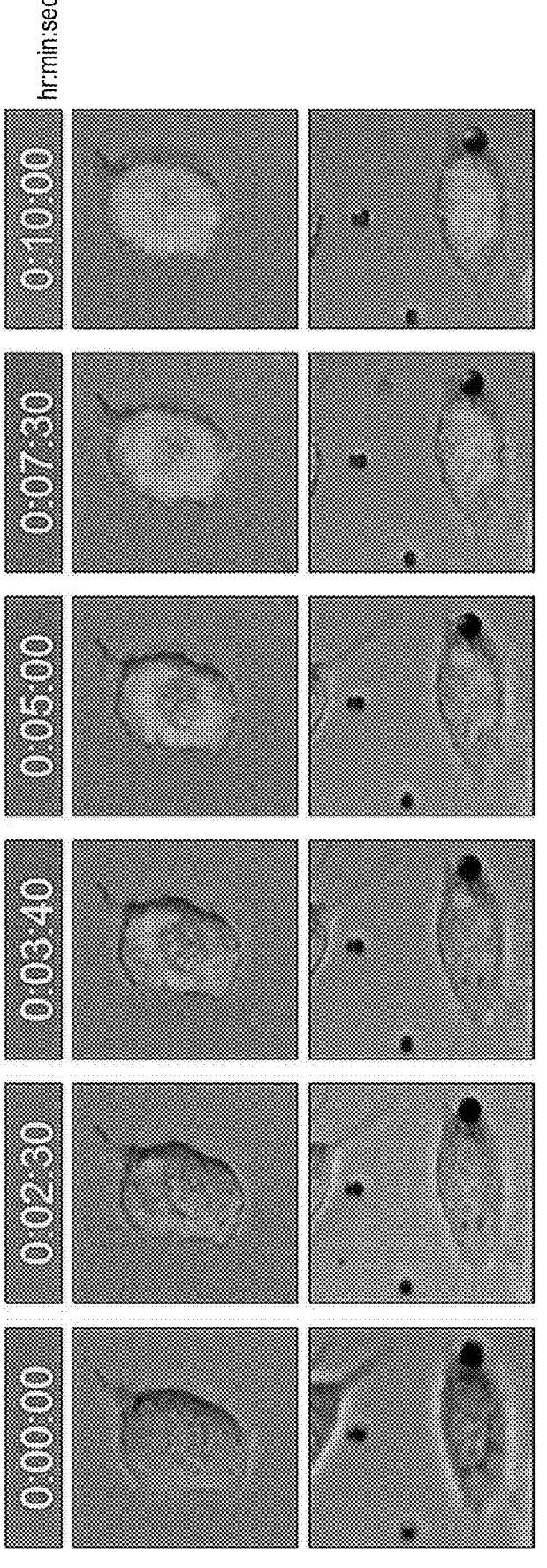

FIGS. 8 and 9 demonstrate the accumulation of intracellular calcium in response to treatment with 30 µM Compound 1, as observed by pre-incubation of A549 cells with the intracellular calcium dye, 2.5 µM Fluo-2-AM. Interestingly, a higher than typical dose of compound 2 needed to be used, as the dye is also a calcium chelator. Timestamps for the duration of the experiment are indicated in each panel.

Example 4: Compound Efficacy in an Athymic
Xenograft Mouse Model of Cancer

Female athymic nu/nu mice (6-8 weeks old) were purchased from Simonsen labs (n=12) and were housed at the Murigenics vivarium in Vallejo. The mice were acclimated to the setting of the vivarium for 5 days and maintained on a standard chow diet; 12:12 dark/light cycle; and group housed (3 mice per cage) in HEPA-filtered cages. After acclimation, each mouse was injected subcutaneously (lower left abdominal flank) with 5×10^6 A549 (ATCC: CCL-185) cells mixed with 1:1 (v/v) with Matrigel solution. When the tumors reached a volume of—100 mm3, the mice were divided into separate treatment groups for the desired treatments. Experiments using both intra-tumoral (IT) and intraperitoneal (IP) administration were performed and the data are reported in FIGS. 10 and 11.

Experiment 1: Intra-Tumoral (IT) Dosing

Mice prepared as described above were divided into 4 groups:

Group 1: received an intra-tumoral injection of 50 microliters of Phosphate Buffered Saline (mock) (n=3)

Group 2: received an intra-tumoral injection of 50 microliters of 10 mg/ml Compound 1 in Phosphate Buffered Saline (n=3)

Group 3: received an intra-tumoral injection of 50 microliters of 20 mg/ml Compound 1 in Phosphate Buffered Saline (n=3)

The 50 microliter injections were carried out with a (30 g needle). The injections were administered on day zero and then again on day 3, and every other day. The length (L) and the width (W) of the tumor mass was measured with a Vernier caliper and the tumor volume (V) was calculated as $V=(L \times WA2)/2$. The relative tumor volume of each tumor mass on each measurement day was normalized against the initial volume of the same mass on day zero right before initiation of injections. Measurements were performed on days 0, 3, 5, 7, and 10 and the data for individual mice is shown in FIG. 9, which shows measurable decreases in tumor size as early as day 3.

Experiment 2: Intra-Peritoneal (IP) Dosing

Mice prepared as described above were divided into 2 groups:

Group 1: received an intra-peritoneal injection of 125 microliters of Phosphate Buffered Saline (mock) (n=3)

Group 2: received an intra-peritoneal injection of 125 microliters of 3 mg/ml Compound 1 in Phosphate Buffered Saline (n=3)

The injections were carried out with a 30 g needle. The injections were administered on day seven. The length (L) and the width (W) of the tumor mass was measured with a Vernier caliper and the tumor volume (V) was calculated as $V=(L \times WA2)/2$. The relative tumor volume of each tumor mass on each measurement day was normalized against the initial volume of the same mass on day zero right before initiation of injections. Measurements were performed through days 0-10, with IP dosing on day 7, and the data is summarized in FIG. 10, which shows measurable decreases in tumor size as early as 3 days after injection (day 10).

Example 5: Cellular Assay for RAD51 Inhibition in
SSP-25 Cells

The efficacy of the peptides described herein was assessed by their ability to cause death in SSP-25 cells, which have amplification of RAD51 and are dependent on its activity.

First, 5,000 SSP25 cells were plated, and adherence and growth was measured for 20 hours using live measurements of current impedance through the plate using the xCELLigence™ instrument. At the 20 hour mark, a concentration gradient of each compound or a PBS control was added to the SSP-25 cells, which were cultured in 100 µM RMPI media with 10% FBS. Acute death kinetics were observed in real time and the cells were allowed to keep growing. The concentration gradient was used for IC50 value calculation as summarized in Table 5 below. Only values with confidence and $R^{\hat{}}>0.85$ are shown.

| Compound # | CPP N or C? | CPP | add N-terminal | AA1 | AA2 | AA3 | AA4 | AA5 | AA6 | AA7 | AA8 | AA9 | AA10 | AA11 | AA12 | AA13 | Add C-term | IC50 |
|---|---|---|---|---|---|---|---|---|---|---|---|---|---|---|---|---|---|---|
| 1 | C | rrrrrrr (SEQ ID NO: 147) | | l | m | r | s | v | r | l | r | v | G | l | r | k | | 2.4 |
| 2 | C | rrrrrrr (SEQ ID NO: 147) | | l | m | r | s | q | r | l | r | q | G | l | r | k | | 4224 |
| 3 | C | cFΦR4 (SEQ ID NO: 54) | | l | m | r | s | v | r | l | r | v | G | l | r | k | aG | 7.3 |
| 4 | None | None | | l | m | r | s | v | r | l | r | v | G | l | r | r | | 67 |
| 5 | C | rrrrrrrr | | l | V | r | s | v | — | — | — | — | G | l | r | r | | 35 |
| 6 | N | rrrrrr | aGphl | R | K | v | r | a | l | r | s | l | G | l | r | l | aq | 417 |
| 7 | N | rrrrrrrr | | rev-l | rev-v | rev-r | rev-s | rev-v | — | — | — | — | G | l | — | — | | |
| 8 | N | rrrrrrr (SEQ ID NO: 147) | | | | | | | | | | | | | | | | |
| 9 | C | rrrrrrr (SEQ ID NO: 147) | | L | d-nLeu | r | s | v | r | l | r | v | G | l | r | k | | 20 |
| 10 | C | rrrrrrr (SEQ ID NO: 147) | | L | d-nLeu | r | G | v | r | l | r | v | G | l | r | k | | 13 |
| 11 | C | rrrrGy (SEQ ID NO: 148) | | L | d-nLeu | r | G | v | r | l | r | v | G | l | r | k | | 9 |
| 12 | C | rrrrrGΦ (SEQ ID NO: 149) | | L | d-nLeu | r | G | v | r | l | r | v | G | l | r | k | | 17 |
| 13 | C | rrrrrrrk (C6_5FAM) (SEQ ID NO: 150) | | L | m | r | s | v | r | l | r | v | G | l | r | k | | 10 |
| 14 | C | rrrrrGΦ (SEQ ID NO: 149) | | L | d-nLeu | r | s | r | r | l | r | v | G | l | r | k | | 3499 |
| 15 | C | rrrrrGΦ (SEQ ID NO: 149) | | L | d-nLeu | r | abu | v | r | l | r | v | G | l | r | k | | 7.2 |
| 16 | C | rrrrrGΦ (SEQ ID NO: 149) | | L | d-nLeu | r | s | v | r | l | r | d-nLeu | G | l | r | k | | 43 |
| 17 | C | rrrrrGΦ (SEQ ID NO: 149) | | L | d-nLeu | r | s | v | r | l | r | v | b-ala | l | r | k | | 20 |
| 18 | C | rrrrrGΦ (SEQ ID NO: 149) | | L | d-nLeu | r | abu | r | r | l | r | d-nLeu | b-ala | l | r | k | | 17.8 |
| 19 | C | rrrrr | Dan-Sar | L | d-nLeu | r | s | v | r | l | r | v | G | l | r | k | | 6.2 |
| 20 | C | rrrrrr-sarcosine-sarcosine-OMe (SEQ ID NO: 151) | Dan-Sar | L | d-nLeu | r | s | v | r | l | r | v | G | l | r | r | | 8.6 |
| 21 | C | rrrrrr-sarcosine- | | L | d-nLeu | r | s | v | r | l | r | v | G | l | r | r | | 25 |

-continued

| Com- pound # | CPP N or C? | CPP | add N-terminal | AA1 | AA2 | AA3 | AA4 | AA5 | AA6 | AA7 | AA8 | AA9 | AA10 | AA11 | AA12 | AA13 | Add C-term | IC50 |
|---|---|---|---|---|---|---|---|---|---|---|---|---|---|---|---|---|---|---|
| | | sarcosine- OMe (SEQ ID NO: 151) | | | | | | | | | | | | | | | | |
| 22 | C | rrrrrGΦ (SEQ ID NO: 149) | | L | d- nLeu | r | b- ala | v | r | l | r | v | b- ala | l | r | k | | 18 |
| 23 | C | r(Ahx) r(Ahx) r(Ahx) r(Ahx) r(Ahx)r (SEQ ID NO: 152) | | L | d- nLeu | r | a | v | r | l | r | v | b- ala | l | r | | (Ahx) | 20.6 |
| 24 | C | r(Ahx) r(Ahx) r(Ahx) r(Ahx) r(Ahx) r(Ahx)y (SEQ ID NO: 153) | | L | d- nLeu | r | a | v | r | l | r | v | b- ala | l | r | | (Ahx) | 6.2 |
| 25 | C | r(Ahx) r(Ahx) r(Ahx) r(Ahx) r(Ahx) r(Ahx)r (SEQ ID NO: 152) | | L | d- nLeu | r | s | v | r | l | r | v | G | l | r | | (Ahx) | 14 |

Example 6: Hemolysis Activity Assay

To assess the nonspecific lytic properties of each compounds disclosed herein, each mentioned compound was tested for hemolytic properties against fresh human RBCs.

Briefly, donor blood was drawn into a K2EDTA anticoagulant tube from multiple O+ donors. The blood was washed 3 times in PBS. RBCs were diluted to 2% in PBS and compounds were added at various concentrations. Samples were incubated at 37 C for 1 hr, then centrifuged at 2200 rpm for 5 min. Supernatants were measured for absorbance at 450 nm or 405 nm.

The percentage hemolysis was calculated as lysis relative to 1% Triton X-100 incubation. Results are shown in Table below.

| Compound | % Hemolysis (250 uM) |
|---|---|
| 1 | 3% |
| 2 | 1% |
| 15 | 49% |
| 17 | 32% |
| 18 | 17% |
| 19 | 86% |
| 20 | 84% |
| 21 | 31% |
| 22 | 5% |
| 23 | 3% |
| 24 | 3% |
| 25 | 4% |

Example 7: Pharmacokinetic, Serum, and Microsome Studies on Optimized Compounds The pharmocokinetic parameters in mice by both intravenous (IV) and intraperitoneal (IP) dosing, as well as the serum and microsome stability for each of compound 22, 23, 24, and 25 was determined. Bioanalytical methods were developed for each compound using an LC-MS/MS method with LLOQ>100 ng/ml.

For in-vivo PK work, at least 3 mice were used per timepoint. For each compound, the animals were injected either IV or IP with the compound. IV injections used 1 mg/kg, and IP injections were at 15 mg/kg. Blood was collected at the indicated timepoints and analyzed according to the bioanalytical method developed.

Serum stability data was obtained using the appropriate animal serum, each incubated with the compound for up to two hours at 37 C.

For HLM and MLM stability studies, each compound was incubated with the liver microsome mixture for up to an hour at 37 C in the presence of NADPH.

Positive compound controls were included with each experiment to confirm the activity of the microsome samples. After the incubations, the reactions were stopped and the compounds were analyzed according to the method developed for each.

The results for IV and TP pharmacokinetic assays for compounds according to the disclosure are described in Table 7 below.

TABLE 7

| | | | | | | AUC | | | | MRTI |
|---|---|---|---|---|---|---|---|---|---|---|
| Compound # | Dosing route | t½ (hr) | C0 (ng/mL) | AUClast (hr*ng/mL) | AUCInf (hr*ng/mL) | Extr (%) | Vz (L/kg) | Vss (L/kg) | CL (mL/min/kg) | nf (hr) |
| 22 | 1 mg/kg IV | 0.119 | 514 | 63.9 | 79.3 | 19.8 | 2.04 | 1.87 | 222 | 0.158 |
| | 15 mg/kg IP | 0.605 | 0.444 | 388 | 463 | 539 | 15.5 | 1.19 | 35.9 | 48.3 |
| 23 | 1 mg/kg IV | 0.565 | 1479 | 347 | 490 | 28.5 | 1.71 | 1.56 | 36.1 | 0.738 |
| | 15 mg/kg IP | NA | 10.5 | 1657 | 341 | NA | NA | NA | NA | 6.56 |
| 24 | 1 mg/kg IV | 0.549 | 683 | 375 | 528 | 28.8 | 1.51 | 1.48 | 31.7 | 0.779 |
| | 15 mg/kg IP | 1.89 | 0.75 | 647 | 1007 | 1933 | 46 | 2.95 | 129 | 17.9 |
| 25 | 1 mg/kg IV | 0.423 | 750 | 254 | 308 | 16.8 | 1.99 | 1.8 | 55.7 | 0.551 |
| | 15 mg/kg IP | 2.14 | 1.26 | 675 | 831 | 3187 | 58.3 | 3.41 | 212 | 21.8 |

PK and stability data for compounds described herein is presented in Table 8 below.

TABLE 8

| | Half-life Mouse IV (min) | Half-life Mouse IP (min) | Human Serum Stability (min) | Mouse Serum Stability (min) | HLM Stability (min) | MLM Stability (min) |
|---|---|---|---|---|---|---|
| Compound # | | | | | | |
| 22 | 7.16 | 36.28 | >500 | >500 | 364.81 | >500 |
| 23 | 33.84 | n/a | | >500 | 108.3042 | 41.75585 |
| 24 | 32.96 | 112.8 | | 277.2589 | 56.81534 | 115.5245 |
| 25 | 25.35 | 128.22 | | >500 | 81.54673 | 46.20981 |

Figure 13:
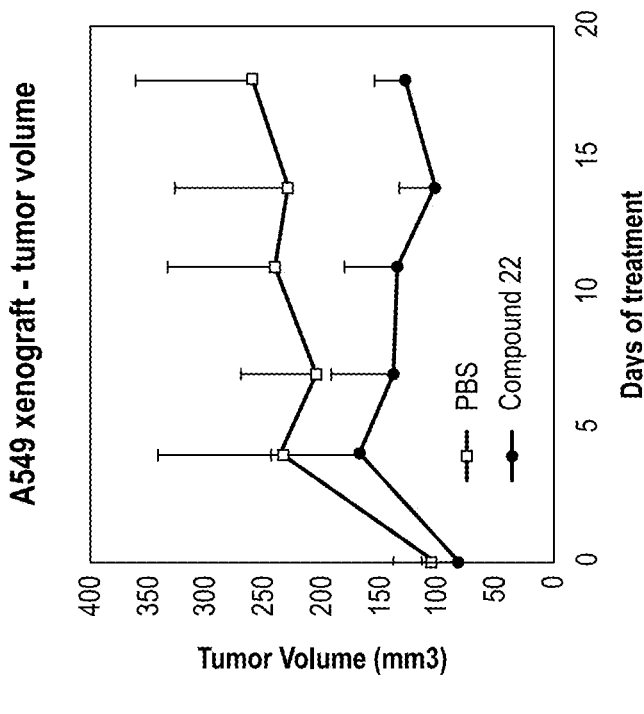
FIG. 13 depicts time-course data for the athymic mouse xenograft experiment of Example 8.
Figure 13:
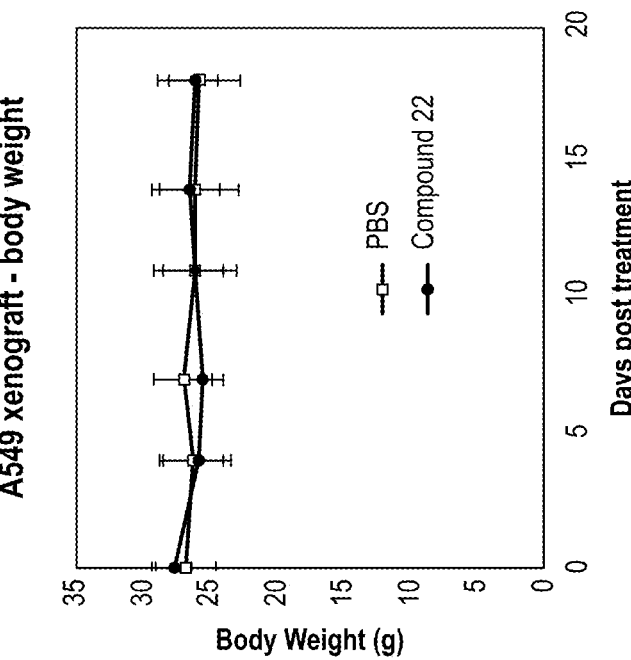
Figure 14:
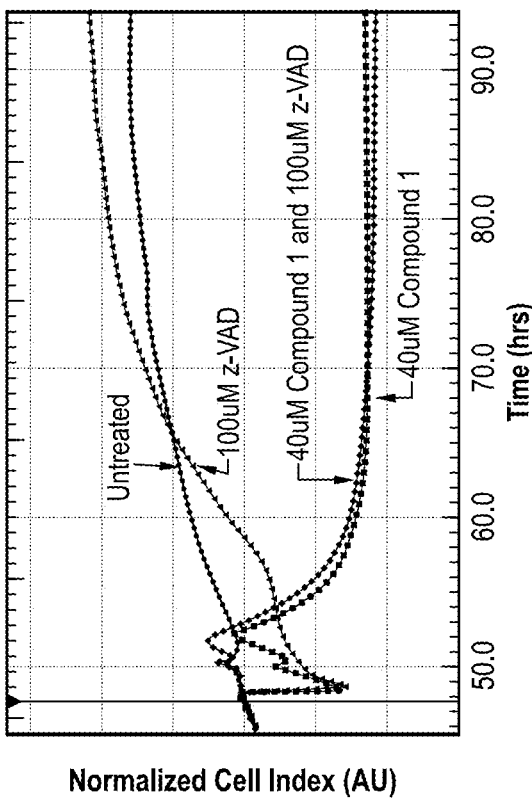
FIG. 14 depicts an xCELLigence cell death assay on SSP25 cells, wherein the necroptosis inhibitor Necrostatin is added alone or combined with compound 1 (left) or the apoptosis inhibitor z-VAD is administered alone or in combination with compound 1 (right), demonstrating that compound 1 does not cause cell death through necroptosis or apoptosis.
Figure 14:
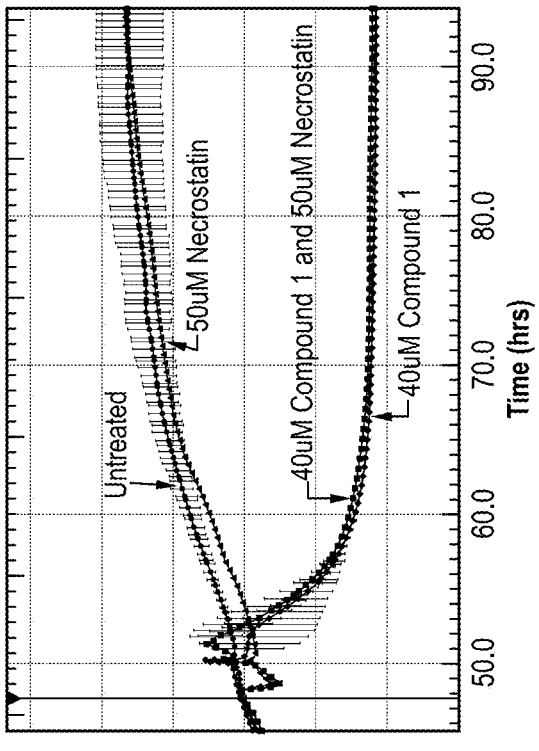

Graphs for derivation of PK/PD parameters for the compounds in Tables 7 and 8 are presented in FIG. 13 (compound 22, 23, 24 and 25).

Example 8: Activity in A549 Xeno2Raft Cancer Model

The anti-cancer activity of compound 22 was assessed in an A549 xenograft model in a method similar to Example 4. Briefly, A549 cells were implanted into athymic nude female mice. Tumors were allowed to grow to 100 mm^3 before initiation of dosing. Mice were randomly distributed into dosing groups with at least 3 animals per group. Mice were dosed using 15 mpk TP injections every other day.

Tumor volumes and mouse weights were recorded at the indicated timepoints. Terminal tumors were excised and weighed (N=3 for each group). Results for this experiment are summarized in FIG. 15. Tumor growth rate and ending tumor side suggests that administration of compound 22 is effective to reduce tumor growth in the A549 xenograft model.

Example 9: Cell Death Mechanism for Compound 1

Further experiments were performed to elucidate the method of cell death induced by Compound 1. In one experiment, xCELLIGENCE cell death assays as in Examples 1 and 5 were performed, treating with either a necroptosis inhibitor (Necrostatin, 50 μM) alone or in combination with Compound 1 (40 μM). In another experiment, xCELLIGENCE cell death assays as in Examples 1 and 5 were performed, treating with either a apoptosis inhibitor (z-VAD, 100 μM) alone or in combination with Compound 1 (40 μM). In both cases, addition of the inhibitor has no effect on the activity of Compound 1, as exhibited by the fact that the Compound 1 and Compound 1+necrostatin/z-VAD lines overlap. This suggests the mechanism of cell death for Compound 1 does not involve necroptosis or apoptosis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A non-naturally occurring peptide comprising a targeting motif of Formula I or an invert thereof:

(Formula I)

(SEQ ID NO: 61)

L-X1-R-X2-V-R-L-R-X3-Y1-L-R-X4 wherein:

$X_1$-$X_4$ and $Y_1$ are independently selected from the 20 natural L- or D-amino acids, or Met(O), Met(O)2, Se-Met, Abu (α-aminobutyric acid), Bal (Beta-Alanine), Hse, nme-Ser, and Ahx; and wherein L, R, and V are D- or L-amino acids, wherein the peptide further comprises a cell-penetrating peptide motif, or a retro-invert thereof.

2. The non-naturally occurring peptide of claim 1, wherein the cell-penetrating peptide motif is C-terminal to the motif of Formula I.

3. The non-naturally occurring peptide of claim 1, wherein the cell-penetrating peptide motif is AIP6 (SEQ ID NO: 2), DPV6 (SEQ ID NO: 3), HIV-1 TAT (SEQ ID NO: 4), IRS-tag (SEQ ID NO: 5), mini-penetratin (SEQ ID NO: 6), penetratin (SEQ ID NO: 7), $R_7$ (SEQ ID NO: 129), $R_8$ (SEQ ID NO: 8), $R_9$ (SEQ ID NO: 131), $R_{10}$ (SEQ ID NO: 132), $R_{11}$ (SEQ ID NO: 133), $R_{12}$ (SEQ ID NO: 134), R9F2C (SEQ ID NO: 135), CADY (SEQ ID NO: 10), EB-1 (SEQ ID NO: 11), hCT (SEQ ID NO: 12), PTD4 (SEQ ID NO: 13), MAP (SEQ ID NO: 14), Pep-1 (SEQ ID NO: 15), Pvec (SEQ ID NO: 16), SynB1 (SEQ ID NO: 17), Transportan (SEQ ID NO: 18), VP1 (SEQ ID NO: 19), MAP17 (SEQ ID NO: 20), PreS2 (SEQ ID NO: 21), GALA (SEQ ID NO: 22), MAP12 (SEQ ID NO: 23), (PRR)3 (SEQ ID NO: 24), (PRR)4 (SEQ ID NO: 142), (PRR)5 (SEQ ID NO: 143), (PRR)6 (SEQ ID NO: 144), (PPR)3 (SEQ ID NO: 25), (PPR)4 (SEQ ID NO: 145), (PPR)5 (SEQ ID NO: 146), (PPR)6 (SEQ ID NO: 130), Bac-7 (SEQ ID NO: 26), SAP (SEQ ID NO: 27), BIP (SEQ ID NO: 29), C105Y (SEQ ID NO: 30), β3-integrin (SEQ ID NO: 31), K-FGF (SEQ ID NO: 32), NF-κB (SEQ ID NO: 33), Pep7 (SEQ ID NO: 34), β1-tail (SEQ ID NO: 35), rrrrrrr (SEQ ID NO: 147), cFΦR4 (SEQ ID NO: 54), rrrrGy (SEQ ID NO: 148), rrrrrGΦ (SEQ ID NO: 149), rrrrrrrk(C6_5FAM) (SEQ ID NO: 150), rrrrrr-sarcosine-sarcosine-OMe (SEQ ID NO: 151), or r(Ahx)r (Ahx)r(Ahx)r(Ahx)r(Ahx)r (SEQ ID NO: 152), or r(Ahx)r (Ahx)r(Ahx)r(Ahx)r(Ahx)y (SEQ ID NO: 153), or a retro-invert thereof, or a combination thereof.

4. The non-naturally occurring peptide of claim 1, wherein the targeting motif is selected from the group consisting of:

(SEQ ID NO: 156)

ImrsvrlrvGlrkaG;

(SEQ ID NO: 157)

lmrsvrlrvGlrr;

(SEQ ID NO: 154)

lmrsvrlrvGlrk; or (SEQ ID NO: 159)

krlGvrlrvsrml.

* * * * *

SEQUENCE LISTING

Sequence total quantity: 190
SEQ ID NO: 1              moltype = AA  length = 8
FEATURE                   Location/Qualifiers
REGION                    1..8
                          note = Description of Artificial Sequence: Synthetic peptide
VARIANT                   4
                          note = MOD_RES - Leu, Met, or Val
VARIANT                   7
                          note = MOD_RES - Arg, Leu, or Lys
VARIANT                   8
                          note = MOD_RES - Arg, Phe, or Val
source                    1..8
                          mol_type = protein
                          organism = synthetic construct
SEQUENCE: 1
RLGXSRXX                                                               8

SEQ ID NO: 2              moltype = AA  length = 5
FEATURE                   Location/Qualifiers
REGION                    1..5
                          note = Description of Unknown: AIP6 sequencee
source                    1..5
                          mol_type = protein
                          organism = unidentified
SEQUENCE: 2
RLRWR                                                                  5

SEQ ID NO: 3              moltype = AA  length = 17
FEATURE                   Location/Qualifiers
REGION                    1..17
                          note = Description of Artificial Sequence: Synthetic peptide
source                    1..17
                          mol_type = protein
                          organism = synthetic construct
SEQUENCE: 3
GRPRESGKKR KRKRLKP                                                     17

SEQ ID NO: 4              moltype = AA  length = 13
FEATURE                   Location/Qualifiers
source                    1..13
                          mol_type = protein
                          organism = Human immunodeficiency virus 1
SEQUENCE: 4
GRKKRRQRRR PPQ                                                         13

SEQ ID NO: 5              moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 5
RYIRS                                                                  5

SEQ ID NO: 6              moltype = AA  length = 7
FEATURE                   Location/Qualifiers
source                    1..7
                          mol_type = protein
                          organism = Drosophila sp.
SEQUENCE: 6
RRMKWKK                                                                7

SEQ ID NO: 7              moltype = AA  length = 16
FEATURE                   Location/Qualifiers
source                    1..16
                          mol_type = protein
                          organism = Drosophila sp.
SEQUENCE: 7
RQIKIWFQNR RMKWKK                                                      16

SEQ ID NO: 8              moltype = AA  length = 8
FEATURE                   Location/Qualifiers
REGION                    1..8
                          note = Description of Artificial Sequence: Synthetic peptide
source                    1..8
                          mol_type = protein
                          organism = synthetic construct

```
SEQUENCE: 8
RRRRRRRR                                                                    8

SEQ ID NO: 9        moltype = AA  length = 12
FEATURE             Location/Qualifiers
REGION              1..12
                    note = Description of Artificial Sequence: Synthetic peptide
source              1..12
                    mol_type = protein
                    organism = synthetic construct
SEQUENCE: 9
RRRRRRRRRF FC                                                               12

SEQ ID NO: 10       moltype = AA  length = 20
FEATURE             Location/Qualifiers
REGION              1..20
                    note = Description of Artificial Sequence: Synthetic peptide
source              1..20
                    mol_type = protein
                    organism = synthetic construct
SEQUENCE: 10
GLWRALWRLL RSLWRLLWRA                                                       20

SEQ ID NO: 11       moltype = AA  length = 23
FEATURE             Location/Qualifiers
REGION              1..23
                    note = Description of Artificial Sequence: Synthetic peptide
source              1..23
                    mol_type = protein
                    organism = synthetic construct
SEQUENCE: 11
LIRLWSHLIH IWFQNRRLKW KKK                                                   23

SEQ ID NO: 12       moltype = AA  length = 24
FEATURE             Location/Qualifiers
REGION              1..24
                    note = Description of Artificial Sequence: Synthetic peptide
source              1..24
                    mol_type = protein
                    organism = synthetic construct
SEQUENCE: 12
LGTYTQDFNK FHTFPQTAIG VGAP                                                  24

SEQ ID NO: 13       moltype = AA  length = 11
FEATURE             Location/Qualifiers
REGION              1..11
                    note = Description of Artificial Sequence: Synthetic peptide
source              1..11
                    mol_type = protein
                    organism = synthetic construct
SEQUENCE: 13
YARAAARQAR A                                                                11

SEQ ID NO: 14       moltype = AA  length = 17
FEATURE             Location/Qualifiers
REGION              1..17
                    note = Description of Artificial Sequence: Synthetic peptide
source              1..17
                    mol_type = protein
                    organism = synthetic construct
SEQUENCE: 14
KLALKALKAL KAALKLA                                                          17

SEQ ID NO: 15       moltype = AA  length = 20
FEATURE             Location/Qualifiers
REGION              1..20
                    note = Description of Artificial Sequence: Synthetic peptide
source              1..20
                    mol_type = protein
                    organism = synthetic construct
SEQUENCE: 15
KETWWETWWT EWSQPKKRKV                                                       20

SEQ ID NO: 16       moltype = AA  length = 18
FEATURE             Location/Qualifiers
source              1..18
                    mol_type = protein
                    organism = Mus sp.
SEQUENCE: 16
```

```
LLIILRRRIR KQAHAHSK                                                  18

SEQ ID NO: 17          moltype = AA  length = 18
FEATURE                Location/Qualifiers
REGION                 1..18
                       note = Description of Unknown: Pegelin/SynB1 sequence
source                 1..18
                       mol_type = protein
                       organism = unidentified
SEQUENCE: 17
RGGRLSYSRR RFSTSTGR                                                  18

SEQ ID NO: 18          moltype = AA  length = 27
FEATURE                Location/Qualifiers
REGION                 1..27
                       note = Description of Artificial Sequence: Synthetic peptide
source                 1..27
                       mol_type = protein
                       organism = synthetic construct
SEQUENCE: 18
GWTLNSAGYL LGKINLKALA ALAKKIL                                        27

SEQ ID NO: 19          moltype = AA  length = 10
FEATURE                Location/Qualifiers
source                 1..10
                       mol_type = protein
                       organism = Alphapolyomavirus sp.
                       note = Polyomavirus sp.
SEQUENCE: 19
APKRKSGVSK                                                           10

SEQ ID NO: 20          moltype = AA  length = 18
FEATURE                Location/Qualifiers
REGION                 1..18
                       note = Description of Artificial Sequence: Synthetic peptide
source                 1..18
                       mol_type = protein
                       organism = synthetic construct
SEQUENCE: 20
QLALQLALQA LQAALQLA                                                  18

SEQ ID NO: 21          moltype = AA  length = 12
FEATURE                Location/Qualifiers
REGION                 1..12
                       note = Description of Artificial Sequence: Synthetic peptide
source                 1..12
                       mol_type = protein
                       organism = synthetic construct
SEQUENCE: 21
PLSSIFSRIG DP                                                        12

SEQ ID NO: 22          moltype = AA  length = 30
FEATURE                Location/Qualifiers
REGION                 1..30
                       note = Description of Artificial Sequence: Synthetic
                        polypeptide
source                 1..30
                       mol_type = protein
                       organism = synthetic construct
SEQUENCE: 22
WEAALAEALA EALAEHLAEA LAEALEALAA                                     30

SEQ ID NO: 23          moltype = AA  length = 18
FEATURE                Location/Qualifiers
REGION                 1..18
                       note = Description of Artificial Sequence: Synthetic peptide
source                 1..18
                       mol_type = protein
                       organism = synthetic construct
SEQUENCE: 23
LKTLTETLKE LTKTLTEL                                                  18

SEQ ID NO: 24          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
```

```
SEQUENCE: 24
PRRPRRPRR                                                                      9

SEQ ID NO: 25           moltype = AA   length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 25
PPRPPRPPR                                                                      9

SEQ ID NO: 26           moltype = AA   length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 26
RRIRPRPPRL PRPRPRPLPF PRPG                                                     24

SEQ ID NO: 27           moltype = AA   length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 27
VRLPPPVRLP PPVRLPPP                                                            18

SEQ ID NO: 28           moltype = AA   length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 28
VELPPPVELP PPVELPPP                                                            18

SEQ ID NO: 29           moltype = AA   length = 6
FEATURE                 Location/Qualifiers
REGION                  1..6
                        note = Description of Artificial Sequence: Synthetic peptide
VARIANT                 6
                        note = MISC_FEATURE - May or may not be present
source                  1..6
                        mol_type = protein
                        organism = synthetic construct
SEQUENCE: 29
VPMLKE                                                                         6

SEQ ID NO: 30           moltype = AA   length = 17
FEATURE                 Location/Qualifiers
REGION                  1..17
                        note = Description of Artificial Sequence: Synthetic peptide
VARIANT                 1..11
                        note = MISC_FEATURE - This region may or may not be present
                         in its entirety
source                  1..17
                        mol_type = protein
                        organism = synthetic construct
SEQUENCE: 30
CSIPPEVKFN KPFVYLI                                                             17

SEQ ID NO: 31           moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 31
VTVLALGALA GVGVG                                                               15

SEQ ID NO: 32           moltype = AA   length = 12
```

-continued

```
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 32
AAVLLPVLLA AP                                                          12

SEQ ID NO: 33            moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 33
VQRKRQKLMP                                                             10

SEQ ID NO: 34            moltype = AA   length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 34
SDLWEMMMVS LACQY                                                       15

SEQ ID NO: 35            moltype = AA   length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 35
YKSAVTTVVN PKYEGK                                                      16

SEQ ID NO: 36            moltype = AA   length = 19
FEATURE                  Location/Qualifiers
REGION                   1..19
                         note = Description of Artificial Sequence: Synthetic peptide
source                   1..19
                         mol_type = protein
                         organism = synthetic construct
SEQUENCE: 36
VKRGLKLRHV RPRVTRMDV                                                   19

SEQ ID NO: 37            moltype = AA   length = 22
FEATURE                  Location/Qualifiers
REGION                   1..22
                         note = Description of Artificial Sequence: Synthetic peptide
source                   1..22
                         mol_type = protein
                         organism = synthetic construct
SEQUENCE: 37
MVTVLFRRLR IRRACGPPRV RV                                               22

SEQ ID NO: 38            moltype = AA   length = 22
FEATURE                  Location/Qualifiers
REGION                   1..22
                         note = Description of Artificial Sequence: Synthetic peptide
source                   1..22
                         mol_type = protein
                         organism = synthetic construct
SEQUENCE: 38
MVRRFLVTLR IRRACGPPRV RV                                               22

SEQ ID NO: 39            moltype = AA   length = 28
FEATURE                  Location/Qualifiers
source                   1..28
                         mol_type = protein
                         organism = Bos sp.
SEQUENCE: 39
MVKSKIGSWI LVLFVAMWSD VGLCKKRP                                         28

SEQ ID NO: 40            moltype = AA   length = 27
FEATURE                  Location/Qualifiers
```

-continued

```
REGION                1..27
                      note = Description of Artificial Sequence: Synthetic peptide
source                1..27
                      mol_type = protein
                      organism = synthetic construct
SEQUENCE: 40
GALFLGFLGA AGSTMGAWSQ PKKKRKV                                           27

SEQ ID NO: 41         moltype = AA  length = 28
FEATURE               Location/Qualifiers
REGION                1..28
                      note = Description of Artificial Sequence: Synthetic peptide
source                1..28
                      mol_type = protein
                      organism = synthetic construct
SEQUENCE: 41
LSTAADMQGV VTDGMASGLD KDYLKPDD                                          28

SEQ ID NO: 42         moltype = AA  length = 26
FEATURE               Location/Qualifiers
REGION                1..26
                      note = Description of Artificial Sequence: Synthetic peptide
source                1..26
                      mol_type = protein
                      organism = synthetic construct
SEQUENCE: 42
DPKGDPKGVT VTVTVTVTGK GDPKPD                                            26

SEQ ID NO: 43         moltype = AA  length = 24
FEATURE               Location/Qualifiers
REGION                1..24
                      note = Description of Artificial Sequence: Synthetic peptide
source                1..24
                      mol_type = protein
                      organism = synthetic construct
SEQUENCE: 43
RRIRPRPPRL PRPRPRPLPF PRPG                                              24

SEQ ID NO: 44         moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 44
CRWRWKCCKK                                                              10

SEQ ID NO: 45         moltype = AA  length = 19
FEATURE               Location/Qualifiers
REGION                1..19
                      note = Description of Artificial Sequence: Synthetic peptide
source                1..19
                      mol_type = protein
                      organism = synthetic construct
SEQUENCE: 45
GLASTLTRWA HYNALIRAF                                                    19

SEQ ID NO: 46         moltype = AA  length = 10
FEATURE               Location/Qualifiers
REGION                1..10
                      note = Description of Artificial Sequence: Synthetic peptide
source                1..10
                      mol_type = protein
                      organism = synthetic construct
SEQUENCE: 46
PIEVCMYREP                                                              10

SEQ ID NO: 47         moltype = AA  length = 13
FEATURE               Location/Qualifiers
REGION                1..13
                      note = Description of Artificial Sequence: Synthetic peptide
source                1..13
                      mol_type = protein
                      organism = synthetic construct
SEQUENCE: 47
RLSGMNEVLS FRW                                                          13

SEQ ID NO: 48         moltype = AA  length = 21
```

```
FEATURE              Location/Qualifiers
REGION               1..21
                     note = Description of Artificial Sequence: Synthetic peptide
source               1..21
                     mol_type = protein
                     organism = synthetic construct
SEQUENCE: 48
KETWWETWWT EWSQPKKKRK V                                               21

SEQ ID NO: 49        moltype = AA  length = 12
FEATURE              Location/Qualifiers
REGION               1..12
                     note = Description of Artificial Sequence: Synthetic peptide
source               1..12
                     mol_type = protein
                     organism = synthetic construct
SEQUENCE: 49
PLILLRLLRG QF                                                         12

SEQ ID NO: 50        moltype = AA  length = 12
FEATURE              Location/Qualifiers
REGION               1..12
                     note = Description of Artificial Sequence: Synthetic peptide
source               1..12
                     mol_type = protein
                     organism = synthetic construct
SEQUENCE: 50
PLIYLRLLRG QF                                                         12

SEQ ID NO: 51        moltype = AA  length = 15
FEATURE              Location/Qualifiers
REGION               1..15
                     note = Description of Artificial Sequence: Synthetic peptide
source               1..15
                     mol_type = protein
                     organism = synthetic construct
SEQUENCE: 51
KLWMRWYSPT TRRYG                                                      15

SEQ ID NO: 52        moltype = AA  length = 23
FEATURE              Location/Qualifiers
REGION               1..23
                     note = Description of Artificial Sequence: Synthetic peptide
source               1..23
                     mol_type = protein
                     organism = synthetic construct
SEQUENCE: 52
MGLGLHLLVL AAALQGAKKK RKV                                             23

SEQ ID NO: 53        moltype = AA  length = 10
FEATURE              Location/Qualifiers
REGION               1..10
                     note = Description of Artificial Sequence: Synthetic peptide
source               1..10
                     mol_type = protein
                     organism = synthetic construct
SEQUENCE: 53
RRIPNRRPRR                                                            10

SEQ ID NO: 54        moltype = AA  length = 7
FEATURE              Location/Qualifiers
REGION               1..7
                     note = Description of Artificial Sequence: Synthetic peptide
SITE                 2
                     note = MOD_RES - L-2-naphthylalanine
source               1..7
                     mol_type = protein
                     organism = synthetic construct
SEQUENCE: 54
FXRRRRQ                                                               7

SEQ ID NO: 55        moltype =   length =
SEQUENCE: 55
000

SEQ ID NO: 56        moltype =   length =
SEQUENCE: 56
000
```

```
SEQ ID NO: 57            moltype =   length =
SEQUENCE: 57
000

SEQ ID NO: 58            moltype =   length =
SEQUENCE: 58
000

SEQ ID NO: 59            moltype =   length =
SEQUENCE: 59
000

SEQ ID NO: 60            moltype =   length =
SEQUENCE: 60
000

SEQ ID NO: 61            moltype = AA  length = 13
FEATURE                  Location/Qualifiers
REGION                   1..13
                         note = Description of Artificial Sequence: Synthetic peptide
VARIANT                  1
                         note = MOD_RES - May be D- or L-configuration
VARIANT                  2
                         note = MOD_RES - Any of the 20 natural L- or D-amino acids,
                          or L- or D- isomers of Nle - Norleucine, Met(O) -
                          Methionine sulfoxide, Met(O)2 - Methionine sulfone, Se-Met
                          - Selenomethionine, Abu (alpha- aminobutyric acid), Bal
                          (Beta-Alanine), Hse - Homoserine, nme-Ser - N-methylated
                          serine, or Ahx - Aminocaproic acid
VARIANT                  3
                         note = MOD_RES - May be D- or L-configuration
VARIANT                  4
                         note = MOD_RES - Any of the 20 natural L- or D-amino acids,
                          or L- or D- isomers of Nle - Norleucine, Met(O) -
                          Methionine sulfoxide, Met(O)2 - Methionine sulfone, Se-Met
                          - Selenomethionine, Abu (alpha- aminobutyric acid), Bal
                          (Beta-Alanine), Hse - Homoserine, nme-Ser - N-methylated
                          serine, or Ahx - Aminocaproic acid
VARIANT                  5..8
                         note = MOD_RES - May be D- or L-configuration
VARIANT                  9..10
                         note = MOD_RES - Any of the 20 natural L- or D-amino acids,
                          or L- or D- isomers of Nle - Norleucine, Met(O) -
                          Methionine sulfoxide, Met(O)2 - Methionine sulfone, Se-Met
                          - Selenomethionine, Abu (alpha- aminobutyric acid), Bal
                          (Beta-Alanine), Hse - Homoserine, nme-Ser - N-methylated
                          serine, or Ahx - Aminocaproic acid
VARIANT                  11..12
                         note = MOD_RES - May be D- or L-configuration
VARIANT                  13
                         note = MOD_RES - Any of the 20 natural L- or D-amino acids,
                          or L- or D- isomers of Nle - Norleucine, Met(O) -
                          Methionine sulfoxide, Met(O)2 - Methionine sulfone, Se-Met
                          - Selenomethionine, Abu (alpha- aminobutyric acid), Bal
                          (Beta-Alanine), Hse - Homoserine, nme-Ser - N-methylated
                          serine, or Ahx - Aminocaproic acid
source                   1..13
                         mol_type = protein
                         organism = synthetic construct
SEQUENCE: 61
LXRXVRLRXX LRX                                                           13

SEQ ID NO: 62            moltype = AA  length = 14
FEATURE                  Location/Qualifiers
REGION                   1..14
                         note = Description of Artificial Sequence: Synthetic peptide
SITE                     1
                         note = MOD_RES - Dansyl-sarcosine
VARIANT                  2
                         note = MOD_RES - May be D- or L-configuration
VARIANT                  3
                         note = MOD_RES - Any of the 20 natural L- or D-amino acids,
                          or L- or D- isomers of Nle - Norleucine, Met(O) -
                          Methionine sulfoxide, Met(O)2 - Methionine sulfone, Se-Met
                          - Selenomethionine, Abu (alpha- aminobutyric acid), Bal
                          (Beta-Alanine), Hse - Homoserine, nme-Ser - N-methylated
                          serine, or Ahx - Aminocaproic acid
VARIANT                  4
                         note = MOD_RES - May be D- or L-configuration
```

```
VARIANT                  5
                         note = MOD_RES - Any of the 20 natural L- or D-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
VARIANT                  6..9
                         note = MOD_RES - May be D- or L-configuration
VARIANT                  10..11
                         note = MOD_RES - Any of the 20 natural L- or D-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
VARIANT                  12..13
                         note = MOD_RES - May be D- or L-configuration
VARIANT                  14
                         note = MOD_RES - Any of the 20 natural L- or D-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
source                   1..14
                         mol_type = protein
                         organism = synthetic construct
SEQUENCE: 62
XLXRXVRLRX XLRX                                                          14

SEQ ID NO: 63            moltype = AA  length = 12
FEATURE                  Location/Qualifiers
REGION                   1..12
                         note = Description of Artificial Sequence: Synthetic peptide
VARIANT                  2
                         note = MOD_RES - Any of the 20 natural L- or D-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
VARIANT                  4
                         note = MOD_RES - Any of the 20 natural L- or D-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
VARIANT                  9
                         note = MOD_RES - Any of the 20 natural L- or D-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
REGION                   1..12
                         note = See specification as filed for detailed description
                         of substitutions and preferred embodiments
source                   1..12
                         mol_type = protein
                         organism = synthetic construct
SEQUENCE: 63
LXRXVRLRXG LR                                                            12

SEQ ID NO: 64            moltype = AA  length = 14
FEATURE                  Location/Qualifiers
REGION                   1..14
                         note = Description of Artificial Sequence: Synthetic peptide
VARIANT                  2
                         note = MOD_RES - Any of the 20 natural L- or D-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
VARIANT                  4
                         note = MOD_RES - Any of the 20 natural L- or D-amino acids,
                         or L- or D- isomers of Nle - Norleucine, Met(O) -
```

-continued

```
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
VARIANT                  9
                         note = MOD_RES - Any of the 20 natural L- or D-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
VARIANT                  13
                         note = MOD_RES - Any of the 20 natural L- or D-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
VARIANT                  14
                         note = MOD_RES - L- or D- Ser, Gly, Abu - alpha-
                         aminobutyric acid, Ala, Bal - Beta-alanine, Tyr, His, Thr,
                         or Pro
REGION                   1..14
                         note = See specification as filed for detailed description
                         of substitutions and preferred embodiments
source                   1..14
                         mol_type = protein
                         organism = synthetic construct
SEQUENCE: 64
LXRXVRLRXG LRXX                                                             14

SEQ ID NO: 65            moltype = AA  length = 11
FEATURE                  Location/Qualifiers
REGION                   1..11
                         note = Description of Artificial Sequence: Synthetic peptide
VARIANT                  2
                         note = MOD_RES - Any of the 20 common D- or L-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
VARIANT                  4
                         note = MOD_RES - Any of the 20 common D- or L-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
VARIANT                  9
                         note = MOD_RES - Any of the 20 common D- or L-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
VARIANT                  10
                         note = MOD_RES - Any of the 20 common D- or L-amino acids,
                         or L- or D- isomers of Nle - Norleucine, Met(O) -
                         Methionine sulfoxide, Met(O)2 - Methionine sulfone, Se-Met
                         - Selenomethionine, Abu (alpha- aminobutyric acid), Bal
                         (Beta-Alanine), Hse - Homoserine, nme-Ser - N-methylated
                         serine, or Ahx - Aminocaproic acid
source                   1..11
                         mol_type = protein
                         organism = synthetic construct
SEQUENCE: 65
LXRXVRLRXX L                                                                11

SEQ ID NO: 66            moltype =   length =
SEQUENCE: 66
000

SEQ ID NO: 67            moltype =   length =
SEQUENCE: 67
000

SEQ ID NO: 68            moltype =   length =
SEQUENCE: 68
```

-continued

```
000

SEQ ID NO: 69          moltype =    length =
SEQUENCE: 69
000

SEQ ID NO: 70          moltype =    length =
SEQUENCE: 70
000

SEQ ID NO: 71          moltype =    length =
SEQUENCE: 71
000

SEQ ID NO: 72          moltype =    length =
SEQUENCE: 72
000

SEQ ID NO: 73          moltype =    length =
SEQUENCE: 73
000

SEQ ID NO: 74          moltype =    length =
SEQUENCE: 74
000

SEQ ID NO: 75          moltype =    length =
SEQUENCE: 75
000

SEQ ID NO: 76          moltype =    length =
SEQUENCE: 76
000

SEQ ID NO: 77          moltype =    length =
SEQUENCE: 77
000

SEQ ID NO: 78          moltype =    length =
SEQUENCE: 78
000

SEQ ID NO: 79          moltype =    length =
SEQUENCE: 79
000

SEQ ID NO: 80          moltype =    length =
SEQUENCE: 80
000

SEQ ID NO: 81          moltype =    length =
SEQUENCE: 81
000

SEQ ID NO: 82          moltype =    length =
SEQUENCE: 82
000

SEQ ID NO: 83          moltype =    length =
SEQUENCE: 83
000

SEQ ID NO: 84          moltype =    length =
SEQUENCE: 84
000

SEQ ID NO: 85          moltype =    length =
SEQUENCE: 85
000

SEQ ID NO: 86          moltype =    length =
SEQUENCE: 86
000

SEQ ID NO: 87          moltype =    length =
SEQUENCE: 87
000

SEQ ID NO: 88          moltype =    length =
```

-continued

```
SEQUENCE: 88
000

SEQ ID NO: 89          moltype =   length =
SEQUENCE: 89
000

SEQ ID NO: 90          moltype =   length =
SEQUENCE: 90
000

SEQ ID NO: 91          moltype =   length =
SEQUENCE: 91
000

SEQ ID NO: 92          moltype =   length =
SEQUENCE: 92
000

SEQ ID NO: 93          moltype =   length =
SEQUENCE: 93
000

SEQ ID NO: 94          moltype =   length =
SEQUENCE: 94
000

SEQ ID NO: 95          moltype =   length =
SEQUENCE: 95
000

SEQ ID NO: 96          moltype =   length =
SEQUENCE: 96
000

SEQ ID NO: 97          moltype =   length =
SEQUENCE: 97
000

SEQ ID NO: 98          moltype =   length =
SEQUENCE: 98
000

SEQ ID NO: 99          moltype =   length =
SEQUENCE: 99
000

SEQ ID NO: 100         moltype =   length =
SEQUENCE: 100
000

SEQ ID NO: 101         moltype =   length =
SEQUENCE: 101
000

SEQ ID NO: 102         moltype =   length =
SEQUENCE: 102
000

SEQ ID NO: 103         moltype =   length =
SEQUENCE: 103
000

SEQ ID NO: 104         moltype = AA  length = 12
FEATURE                Location/Qualifiers
REGION                 1..12
                       note = Description of Artificial Sequence: Synthetic peptide
SITE                   1
                       note = MOD_RES - D-Norleucine
SITE                   2..8
                       note = MOD_RES - D-amino acid
SITE                   10..12
                       note = MOD_RES - D-amino acid
source                 1..12
                       mol_type = protein
                       organism = synthetic construct
SEQUENCE: 104
XRSVRLRVGL RK                                                          12
```

-continued

```
SEQ ID NO: 105          moltype =    length =
SEQUENCE: 105
000

SEQ ID NO: 106          moltype =    length =
SEQUENCE: 106
000

SEQ ID NO: 107          moltype =    length =
SEQUENCE: 107
000

SEQ ID NO: 108          moltype =    length =
SEQUENCE: 108
000

SEQ ID NO: 109          moltype =    length =
SEQUENCE: 109
000

SEQ ID NO: 110          moltype =    length =
SEQUENCE: 110
000

SEQ ID NO: 111          moltype =    length =
SEQUENCE: 111
000

SEQ ID NO: 112          moltype =    length =
SEQUENCE: 112
000

SEQ ID NO: 113          moltype =    length =
SEQUENCE: 113
000

SEQ ID NO: 114          moltype =    length =
SEQUENCE: 114
000

SEQ ID NO: 115          moltype =    length =
SEQUENCE: 115
000

SEQ ID NO: 116          moltype =    length =
SEQUENCE: 116
000

SEQ ID NO: 117          moltype =    length =
SEQUENCE: 117
000

SEQ ID NO: 118          moltype =    length =
SEQUENCE: 118
000

SEQ ID NO: 119          moltype =    length =
SEQUENCE: 119
000

SEQ ID NO: 120          moltype =    length =
SEQUENCE: 120
000

SEQ ID NO: 121          moltype =    length =
SEQUENCE: 121
000

SEQ ID NO: 122          moltype =    length =
SEQUENCE: 122
000

SEQ ID NO: 123          moltype =    length =
SEQUENCE: 123
000

SEQ ID NO: 124          moltype =    length =
SEQUENCE: 124
000
```

-continued

```
SEQ ID NO: 125          moltype = AA  length = 339
FEATURE                 Location/Qualifiers
source                  1..339
                        mol_type = protein
                        organism = Homo sapiens
SEQUENCE: 125
MAMQMQLEAN ADTSVEEESF GPQPISRLEQ CGINANDVKK LEEAGFHTVE AVAYAPKKEL  60
INIKGISEAK ADKILAEAAK LVPMGFTTAT EFHQRRSEII QITTGSKELD KLLQGGIETG  120
SITEMFGEFR TGKTQICHTL AVTCQLPIDR GGGEGKAMYI DTEGTFRPER LLAVAERYGL  180
SGSDVLDNVA YARAFNTDHQ TQLLYQASAM MVESRYALLI VDSATALYRT DYSGRGELSA  240
RQMHLARFLR MLLRLADEFG VAVVITNQVV AQVDGAAMFA ADPKKPIGGN IIAHASTTRL  300
YLRKGRGETR ICKIYDSPCL PEAEAMFAIN ADGVGDAKD                        339

SEQ ID NO: 126          moltype = AA  length = 14
FEATURE                 Location/Qualifiers
REGION                  1..14
                        note = Description of Artificial Sequence: Synthetic peptide
SITE                    1
                        note = MOD_RES - Dansyl-sarcosine
VARIANT                 2
                        note = MOD_RES - May be D- or L-configuration
VARIANT                 3
                        note = MOD_RES - Any amino acid
VARIANT                 4
                        note = MOD_RES - May be D- or L-configuration
VARIANT                 5
                        note = MOD_RES - Any amino acid
VARIANT                 6..9
                        note = MOD_RES - May be D- or L-configuration
VARIANT                 10..11
                        note = MOD_RES - Any amino acid
VARIANT                 12..13
                        note = MOD_RES - May be D- or L-configuration
VARIANT                 14
                        note = MOD_RES - Any amino acid
source                  1..14
                        mol_type = protein
                        organism = synthetic construct
SEQUENCE: 126
XLXRXVRLRX XLRX                                                    14

SEQ ID NO: 127          moltype = AA  length = 12
FEATURE                 Location/Qualifiers
REGION                  1..12
                        note = Description of Artificial Sequence: Synthetic peptide
VARIANT                 2
                        note = MOD_RES - Any amino acid
VARIANT                 4
                        note = MOD_RES - Any amino acid
VARIANT                 9
                        note = MOD_RES - Any amino acid
REGION                  1..12
                        note = See specification as filed for detailed description
                         of substitutions and preferred embodiments
source                  1..12
                        mol_type = protein
                        organism = synthetic construct
SEQUENCE: 127
LXRXVRLRXG LR                                                      12

SEQ ID NO: 128          moltype = AA  length = 14
FEATURE                 Location/Qualifiers
REGION                  1..14
                        note = Description of Artificial Sequence: Synthetic peptide
VARIANT                 2
                        note = MOD_RES - Any amino acid
VARIANT                 4
                        note = MOD_RES - Any amino acid
VARIANT                 9
                        note = MOD_RES - Any amino acid
VARIANT                 13
                        note = MOD_RES - Any amino acid
VARIANT                 14
                        note = MOD_RES - L- or D- Ser, Gly, Abu - alpha-
                         aminobutyric acid, Ala, Bal - Beta-alanine, Tyr, His, Thr,
                         or Pro
REGION                  1..14
                        note = See specification as filed for detailed description
```

```
                         of substitutions and preferred embodiments
source                   1..14
                         mol_type = protein
                         organism = synthetic construct
SEQUENCE: 128
LXRXVRLRXG LRXX                                                      14

SEQ ID NO: 129           moltype = AA   length = 7
FEATURE                  Location/Qualifiers
REGION                   1..7
                         note = Description of Artificial Sequence: Synthetic peptide
source                   1..7
                         mol_type = protein
                         organism = synthetic construct
SEQUENCE: 129
RRRRRRR                                                               7

SEQ ID NO: 130           moltype = AA   length = 18
FEATURE                  Location/Qualifiers
REGION                   1..18
                         note = Description of Artificial Sequence: Synthetic peptide
source                   1..18
                         mol_type = protein
                         organism = synthetic construct
SEQUENCE: 130
PPRPPRPPRP PRPPRPPR                                                  18

SEQ ID NO: 131           moltype = AA   length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 131
RRRRRRRRR                                                             9

SEQ ID NO: 132           moltype = AA   length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 132
RRRRRRRRRR                                                           10

SEQ ID NO: 133           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 133
RRRRRRRRR R                                                          11

SEQ ID NO: 134           moltype = AA   length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 134
RRRRRRRRR RR                                                         12

SEQ ID NO: 135           moltype = AA   length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 135
RRRRRRRRRF FC                                                        12

SEQ ID NO: 136           moltype = AA   length = 11
FEATURE                  Location/Qualifiers
```

```
REGION                   1..11
                         note = Description of Artificial Sequence: Synthetic peptide
VARIANT                  1
                         note = MOD_RES - May be D- or L-configuration
VARIANT                  2
                         note = MOD_RES - Any of the 20 common D- or L-amino acids,
                          or L- or D- isomers of Nle - Norleucine, Met(O) -
                          Methionine sulfoxide, Met(O)2 - Methionine sulfone, Se-Met
                          - Selenomethionine, Abu (alpha- aminobutyric acid), Bal
                          (Beta-Alanine), Hse - Homoserine, nme-Ser - N-methylated
                          serine, or Ahx - Aminocaproic acid
VARIANT                  3
                         note = MOD_RES - May be D- or L-configuration
VARIANT                  4
                         note = MOD_RES - Any of the 20 common D- or L-amino acids,
                          or L- or D- isomers of Nle - Norleucine, Met(O) -
                          Methionine sulfoxide, Met(O)2 - Methionine sulfone, Se-Met
                          - Selenomethionine, Abu (alpha- aminobutyric acid), Bal
                          (Beta-Alanine), Hse - Homoserine, nme-Ser - N-methylated
                          serine, or Ahx - Aminocaproic acid
VARIANT                  5..8
                         note = MOD_RES - May be D- or L-configuration
VARIANT                  9..10
                         note = MOD_RES - Any of the 20 common D- or L-amino acids,
                          or L- or D- isomers of Nle - Norleucine, Met(O) -
                          Methionine sulfoxide, Met(O)2 - Methionine sulfone, Se-Met
                          - Selenomethionine, Abu (alpha- aminobutyric acid), Bal
                          (Beta-Alanine), Hse - Homoserine, nme-Ser - N-methylated
                          serine, or Ahx - Aminocaproic acid
VARIANT                  11
                         note = MOD_RES - May be D- or L-configuration
source                   1..11
                         mol_type = protein
                         organism = synthetic construct
SEQUENCE: 136
LXRXVRLRXX L                                                             11

SEQ ID NO: 137           moltype = AA  length = 18
FEATURE                  Location/Qualifiers
REGION                   1..18
                         note = Description of Artificial Sequence: Synthetic peptide
source                   1..18
                         mol_type = protein
                         organism = synthetic construct
SEQUENCE: 137
KLALKLALKA LKAALKLA                                                      18

SEQ ID NO: 138           moltype = AA  length = 12
FEATURE                  Location/Qualifiers
REGION                   1..12
                         note = Description of Artificial Sequence: Synthetic peptide
VARIANT                  1
                         note = MOD_RES - May be D- or L-configuration
VARIANT                  2
                         note = MOD_RES - Any amino acid
VARIANT                  3
                         note = MOD_RES - May be D- or L-configuration
VARIANT                  4
                         note = MOD_RES - Any amino acid
VARIANT                  5..8
                         note = MOD_RES - May be D- or L-configuration
VARIANT                  9
                         note = MOD_RES - Any amino acid
VARIANT                  11..12
                         note = MOD_RES - May be D- or L-configuration
REGION                   1..12
                         note = See specification as filed for detailed description
                          of substitutions and preferred embodiments
source                   1..12
                         mol_type = protein
                         organism = synthetic construct
SEQUENCE: 138
LXRXVRLRXG LR                                                            12

SEQ ID NO: 139           moltype = AA  length = 14
FEATURE                  Location/Qualifiers
REGION                   1..14
                         note = Description of Artificial Sequence: Synthetic peptide
VARIANT                  1
```

-continued

```
                      note = MOD_RES - May be D- or L-configuration
VARIANT               2
                      note = MOD_RES - Any amino acid
VARIANT               3
                      note = MOD_RES - May be D- or L-configuration
VARIANT               4
                      note = MOD_RES - Any amino acid
VARIANT               5..8
                      note = MOD_RES - May be D- or L-configuration
VARIANT               9
                      note = MOD_RES - Any amino acid
VARIANT               11..12
                      note = MOD_RES - May be D- or L-configuration
VARIANT               13
                      note = MOD_RES - Any amino acid
VARIANT               14
                      note = MOD_RES - L- or D-Ser, Gly, Abu - alpha-
                       aminobutyric acid, Ala, Bal - Beta-alanine, Tyr, His, Thr,
                       or Pro
REGION                1..14
                      note = See specification as filed for detailed description
                       of substitutions and preferred embodiments
source                1..14
                      mol_type = protein
                      organism = synthetic construct
SEQUENCE: 139
LXRXVRLRXG LRXX                                                                14

SEQ ID NO: 140        moltype = AA  length = 12
FEATURE               Location/Qualifiers
REGION                1..12
                      note = Description of Artificial Sequence: Synthetic peptide
SITE                  1
                      note = MOD_RES - Dansyl-sarcosine
VARIANT               2
                      note = MOD_RES - May be D- or L-configuration
VARIANT               3
                      note = MOD_RES - Any of the 20 common L- or D-amino acids,
                       or L- or D- isomers of Nle - Norleucine, Met(O) -
                       Methionine sulfoxide, Met(O)2 - Methionine sulfone, Se-Met
                       - Selenomethionine, Abu (alpha- aminobutyric acid), Bal
                       (Beta-Alanine), Hse - Homoserine, nme-Ser - N-methylated
                       serine, or Ahx - Aminocaproic acid
VARIANT               4
                      note = MOD_RES - May be D- or L-configuration
VARIANT               5
                      note = MOD_RES - Any of the 20 common L- or D-amino acids,
                       or L- or D- isomers of Nle - Norleucine, Met(O) -
                       Methionine sulfoxide, Met(O)2 - Methionine sulfone, Se-Met
                       - Selenomethionine, Abu (alpha- aminobutyric acid), Bal
                       (Beta-Alanine), Hse - Homoserine, nme-Ser - N-methylated
                       serine, or Ahx - Aminocaproic acid
VARIANT               6..9
                      note = MOD_RES - May be D- or L-configuration
VARIANT               10..11
                      note = MOD_RES - Any of the 20 common L- or D-amino acids,
                       or L- or D- isomers of Nle - Norleucine, Met(O) -
                       Methionine sulfoxide, Met(O)2 - Methionine sulfone, Se-Met
                       - Selenomethionine, Abu (alpha- aminobutyric acid), Bal
                       (Beta-Alanine), Hse - Homoserine, nme-Ser - N-methylated
                       serine, or Ahx - Aminocaproic acid
VARIANT               12
                      note = MOD_RES - May be D- or L-configuration
source                1..12
                      mol_type = protein
                      organism = synthetic construct
SEQUENCE: 140
XLXRXVRLRX XL                                                                  12

SEQ ID NO: 141        moltype = AA  length = 13
FEATURE               Location/Qualifiers
REGION                1..13
                      note = Description of Artificial Sequence: Synthetic peptide
VARIANT               2
                      note = MOD_RES - Any of the 20 common L- or D-amino acids,
                       or L- or D- isomers of Nle - Norleucine, Met(O) -
                       Methionine sulfoxide, Met(O)2 - Methionine sulfone, Se-Met
                       - Selenomethionine, Abu (alpha- aminobutyric acid), Bal
                       (Beta-Alanine), Hse - Homoserine, nme-Ser - N-methylated
```

```
                            serine, or Ahx - Aminocaproic acid
VARIANT                     4
                            note = MOD_RES - Any of the 20 common L- or D-amino acids,
                            or L- or D- isomers of Nle - Norleucine, Met(O) -
                            Methionine sulfoxide, Met(O)2 - Methionine sulfone, Se-Met
                            - Selenomethionine, Abu (alpha- aminobutyric acid), Bal
                            (Beta-Alanine), Hse - Homoserine, nme-Ser - N-methylated
                            serine, or Ahx - Aminocaproic acid
VARIANT                     9..10
                            note = MOD_RES - Any of the 20 common L- or D-amino acids,
                            or L- or D- isomers of Nle - Norleucine, Met(O) -
                            Methionine sulfoxide, Met(O)2 - Methionine sulfone, Se-Met
                            - Selenomethionine, Abu (alpha- aminobutyric acid), Bal
                            (Beta-Alanine), Hse - Homoserine, nme-Ser - N-methylated
                            serine, or Ahx - Aminocaproic acid
VARIANT                     13
                            note = MOD_RES - Any of the 20 common L- or D-amino acids,
                            or L- or D- isomers of Nle - Norleucine, Met(O) -
                            Methionine sulfoxide, Met(O)2 - Methionine sulfone, Se-Met
                            - Selenomethionine, Abu (alpha- aminobutyric acid), Bal
                            (Beta-Alanine), Hse - Homoserine, nme-Ser - N-methylated
                            serine, or Ahx - Aminocaproic acid
source                      1..13
                            mol_type = protein
                            organism = synthetic construct
SEQUENCE: 141
LXRXVRLRXX LRX                                                             13

SEQ ID NO: 142              moltype = AA  length = 12
FEATURE                     Location/Qualifiers
REGION                      1..12
                            note = Description of Artificial Sequence: Synthetic peptide
source                      1..12
                            mol_type = protein
                            organism = synthetic construct
SEQUENCE: 142
PRRPRRPRRP RR                                                              12

SEQ ID NO: 143              moltype = AA  length = 15
FEATURE                     Location/Qualifiers
REGION                      1..15
                            note = Description of Artificial Sequence: Synthetic peptide
source                      1..15
                            mol_type = protein
                            organism = synthetic construct
SEQUENCE: 143
PRRPRRPRRP RRPRR                                                           15

SEQ ID NO: 144              moltype = AA  length = 18
FEATURE                     Location/Qualifiers
REGION                      1..18
                            note = Description of Artificial Sequence: Synthetic peptide
source                      1..18
                            mol_type = protein
                            organism = synthetic construct
SEQUENCE: 144
PRRPRRPRRP RRPRRPRR                                                        18

SEQ ID NO: 145              moltype = AA  length = 12
FEATURE                     Location/Qualifiers
REGION                      1..12
                            note = Description of Artificial Sequence: Synthetic peptide
source                      1..12
                            mol_type = protein
                            organism = synthetic construct
SEQUENCE: 145
PPRPPRPPRP PR                                                              12

SEQ ID NO: 146              moltype = AA  length = 15
FEATURE                     Location/Qualifiers
REGION                      1..15
                            note = Description of Artificial Sequence: Synthetic peptide
source                      1..15
                            mol_type = protein
                            organism = synthetic construct
SEQUENCE: 146
PPRPPRPPRP PRPPR                                                           15

SEQ ID NO: 147              moltype = AA  length = 7
```

-continued

```
FEATURE              Location/Qualifiers
source               1..7
                     mol_type = protein
                     organism = synthetic construct
SITE                 1
                     note = D-amino acid
SITE                 2
                     note = D-amino acid
SITE                 3
                     note = D-amino acid
SITE                 4
                     note = D-amino acid
SITE                 5
                     note = D-amino acid
SITE                 6
                     note = D-amino acid
SITE                 7
                     note = D-amino acid
SEQUENCE: 147
RRRRRRR                                                                7

SEQ ID NO: 148       moltype = AA  length = 6
FEATURE              Location/Qualifiers
source               1..6
                     mol_type = protein
                     organism = synthetic construct
SITE                 1
                     note = D-amino acid
SITE                 2
                     note = D-amino acid
SITE                 3
                     note = D-amino acid
SITE                 4
                     note = D-amino acid
SITE                 6
                     note = D-amino acid
SEQUENCE: 148
RRRRGY                                                                 6

SEQ ID NO: 149       moltype = AA  length = 7
FEATURE              Location/Qualifiers
source               1..7
                     mol_type = protein
                     organism = synthetic construct
SITE                 1
                     note = D-amino acid
SITE                 2
                     note = D-amino acid
SITE                 3
                     note = D-amino acid
SITE                 4
                     note = D-amino acid
SITE                 5
                     note = D-amino acid
SITE                 7
                     note = L-2-naphthylalanine
SEQUENCE: 149
RRRRRGX                                                                7

SEQ ID NO: 150       moltype = AA  length = 8
FEATURE              Location/Qualifiers
source               1..8
                     mol_type = protein
                     organism = synthetic construct
SITE                 1
                     note = D-amino acid
SITE                 2
                     note = D-amino acid
SITE                 3
                     note = D-amino acid
SITE                 4
                     note = D-amino acid
SITE                 5
                     note = D-amino acid
SITE                 6
                     note = D-amino acid
SITE                 7
                     note = D-amino acid
SITE                 8
```

-continued

```
                             note = C6 linker attached to 5-Carboxyfluorescein modified
                              D-amino acid
SEQUENCE: 150
RRRRRRRK                                                                8

SEQ ID NO: 151          moltype = AA  length = 8
FEATURE                 Location/Qualifiers
source                  1..8
                        mol_type = protein
                        organism = synthetic construct
SITE                    1
                        note = D-amino acid
SITE                    2
                        note = D-amino acid
SITE                    3
                        note = D-amino acid
SITE                    4
                        note = D-amino acid
SITE                    5
                        note = D-amino acid
SITE                    6
                        note = D-amino acid
SITE                    7
                        note = Sarcosine
SITE                    8
                        note = Methoxy sarcosine
SEQUENCE: 151
RRRRRRXX                                                                8

SEQ ID NO: 152          moltype = AA  length = 11
FEATURE                 Location/Qualifiers
source                  1..11
                        mol_type = protein
                        organism = synthetic construct
SITE                    1
                        note = D-amino acid
SITE                    2
                        note = 6-aminohexanoic acid
SITE                    3
                        note = D-amino acid
SITE                    4
                        note = 6-aminohexanoic acid
SITE                    5
                        note = D-amino acid
SITE                    6
                        note = 6-aminohexanoic acid
SITE                    7
                        note = D-amino acid
SITE                    8
                        note = 6-aminohexanoic acid
SITE                    9
                        note = D-amino acid
SITE                    10
                        note = 6-aminohexanoic acid
SITE                    11
                        note = D-amino acid
SEQUENCE: 152
RXRXRXRXRX R                                                            11

SEQ ID NO: 153          moltype = AA  length = 13
FEATURE                 Location/Qualifiers
source                  1..13
                        mol_type = protein
                        organism = synthetic construct
SITE                    1
                        note = D-amino acid
SITE                    2
                        note = 6-aminohexanoic acid
SITE                    3
                        note = D-amino acid
SITE                    4
                        note = 6-aminohexanoic acid
SITE                    5
                        note = D-amino acid
SITE                    6
                        note = 6-aminohexanoic acid
SITE                    7
                        note = D-amino acid
SITE                    8
```

-continued

```
                            note = 6-aminohexanoic acid
SITE                        9
                            note = D-amino acid
SITE                        10
                            note = 6-aminohexanoic acid
SITE                        11
                            note = D-amino acid
SITE                        12
                            note = 6-aminohexanoic acid
SITE                        13
                            note = D-amino acid
SEQUENCE: 153
RXRXRXRXRX RXY                                              13

SEQ ID NO: 154              moltype = AA  length = 13
FEATURE                     Location/Qualifiers
source                      1..13
                            mol_type = protein
                            organism = synthetic construct
SITE                        1
                            note = D-amino acid
SITE                        2
                            note = D-amino acid
SITE                        3
                            note = D-amino acid
SITE                        4
                            note = D-amino acid
SITE                        5
                            note = D-amino acid
SITE                        6
                            note = D-amino acid
SITE                        7
                            note = D-amino acid
SITE                        8
                            note = D-amino acid
SITE                        9
                            note = D-amino acid
SITE                        11
                            note = D-amino acid
SITE                        12
                            note = D-amino acid
SITE                        13
                            note = D-amino acid
SEQUENCE: 154
LMRSVRLRVG LRK                                              13

SEQ ID NO: 155              moltype = AA  length = 20
FEATURE                     Location/Qualifiers
source                      1..20
                            mol_type = protein
                            organism = synthetic construct
SITE                        1
                            note = D-amino acid
SITE                        2
                            note = D-amino acid
SITE                        3
                            note = D-amino acid
SITE                        4
                            note = D-amino acid
SITE                        5
                            note = D-amino acid
SITE                        6
                            note = D-amino acid
SITE                        7
                            note = D-amino acid
SITE                        8
                            note = D-amino acid
SITE                        9
                            note = D-amino acid
SITE                        11
                            note = D-amino acid
SITE                        12
                            note = D-amino acid
SITE                        13
                            note = D-amino acid
SITE                        14
                            note = D-amino acid
SITE                        15
                            note = D-amino acid
```

```
SITE                 16
                     note = D-amino acid
SITE                 17
                     note = D-amino acid
SITE                 18
                     note = D-amino acid
SITE                 19
                     note = D-amino acid
SITE                 20
                     note = Amidated D-amino acid
SEQUENCE: 155
LMRSVRLRVG LRKRRRRRRR                                            20

SEQ ID NO: 156       moltype = AA  length = 15
FEATURE              Location/Qualifiers
source               1..15
                     mol_type = protein
                     organism = synthetic construct
SITE                 1
                     note = D-amino acid
SITE                 2
                     note = D-amino acid
SITE                 3
                     note = D-amino acid
SITE                 4
                     note = D-amino acid
SITE                 5
                     note = D-amino acid
SITE                 6
                     note = D-amino acid
SITE                 7
                     note = D-amino acid
SITE                 8
                     note = D-amino acid
SITE                 9
                     note = D-amino acid
SITE                 11
                     note = D-amino acid
SITE                 12
                     note = D-amino acid
SITE                 13
                     note = D-amino acid
SITE                 14
                     note = D-amino acid
SEQUENCE: 156
LMRSVRLRVG LRKAG                                                 15

SEQ ID NO: 157       moltype = AA  length = 13
FEATURE              Location/Qualifiers
source               1..13
                     mol_type = protein
                     organism = synthetic construct
SITE                 1
                     note = D-amino acid
SITE                 2
                     note = D-amino acid
SITE                 3
                     note = D-amino acid
SITE                 4
                     note = D-amino acid
SITE                 5
                     note = D-amino acid
SITE                 6
                     note = D-amino acid
SITE                 7
                     note = D-amino acid
SITE                 8
                     note = D-amino acid
SITE                 9
                     note = D-amino acid
SITE                 11
                     note = D-amino acid
SITE                 12
                     note = D-amino acid
SITE                 13
                     note = D-amino acid
SEQUENCE: 157
LMRSVRLRVG LRR                                                   13
```

```
SEQ ID NO: 158           moltype = AA  length = 13
FEATURE                  Location/Qualifiers
source                   1..13
                         mol_type = protein
                         organism = synthetic construct
SITE                     1
                         note = D-amino acid
SITE                     2
                         note = D-amino acid
SITE                     3
                         note = D-amino acid
SITE                     4
                         note = D-amino acid
SITE                     5
                         note = D-amino acid
SITE                     6
                         note = D-amino acid
SITE                     7
                         note = D-amino acid
SITE                     8
                         note = D-amino acid
SITE                     9
                         note = D-amino acid
SITE                     11
                         note = D-amino acid
SITE                     12
                         note = D-amino acid
SITE                     13
                         note = Amidated D-amino acid
SEQUENCE: 158
LMRSVRLRVG LRR                                                              13

SEQ ID NO: 159           moltype = AA  length = 13
FEATURE                  Location/Qualifiers
source                   1..13
                         mol_type = protein
                         organism = synthetic construct
SITE                     1
                         note = D-amino acid
SITE                     2
                         note = D-amino acid
SITE                     3
                         note = D-amino acid
SITE                     5
                         note = D-amino acid
SITE                     6
                         note = D-amino acid
SITE                     7
                         note = D-amino acid
SITE                     8
                         note = D-amino acid
SITE                     9
                         note = D-amino acid
SITE                     10
                         note = D-amino acid
SITE                     11
                         note = D-amino acid
SITE                     12
                         note = D-amino acid
SITE                     13
                         note = D-amino acid
SEQUENCE: 159
KRLGVRLRVS RML                                                              13

SEQ ID NO: 160           moltype = AA  length = 20
FEATURE                  Location/Qualifiers
source                   1..20
                         mol_type = protein
                         organism = synthetic construct
SITE                     1
                         note = D-amino acid
SITE                     2
                         note = D-amino acid
SITE                     3
                         note = D-amino acid
SITE                     4
                         note = D-amino acid
SITE                     5
                         note = D-amino acid
```

```
SITE                    6
                        note = D-amino acid
SITE                    7
                        note = D-amino acid
SITE                    8
                        note = D-amino acid
SITE                    9
                        note = D-amino acid
SITE                    10
                        note = D-amino acid
SITE                    12
                        note = D-amino acid
SITE                    13
                        note = D-amino acid
SITE                    14
                        note = D-amino acid
SITE                    15
                        note = D-amino acid
SITE                    16
                        note = D-amino acid
SITE                    17
                        note = D-amino acid
SITE                    18
                        note = D-amino acid
SITE                    19
                        note = D-amino acid
SITE                    20
                        note = Amidated D-amino acid
SEQUENCE: 160
RRRRRRRKRL GVRLRVSRML                                        20

SEQ ID NO: 161          moltype = AA  length = 13
FEATURE                 Location/Qualifiers
source                  1..13
                        mol_type = protein
                        organism = synthetic construct
SITE                    1
                        note = D-amino acid
SITE                    2
                        note = D-Norleucine
SITE                    3
                        note = D-amino acid
SITE                    4
                        note = D-amino acid
SITE                    5
                        note = D-amino acid
SITE                    6
                        note = D-amino acid
SITE                    7
                        note = D-amino acid
SITE                    8
                        note = D-amino acid
SITE                    9
                        note = D-amino acid
SITE                    11
                        note = D-amino acid
SITE                    12
                        note = D-amino acid
SITE                    13
                        note = D-amino acid
SEQUENCE: 161
LXRSVRLRVG LRK                                               13

SEQ ID NO: 162          moltype = AA  length = 20
FEATURE                 Location/Qualifiers
source                  1..20
                        mol_type = protein
                        organism = synthetic construct
SITE                    1
                        note = D-amino acid
SITE                    2
                        note = D-Norleucine
SITE                    3
                        note = D-amino acid
SITE                    4
                        note = D-amino acid
SITE                    5
                        note = D-amino acid
SITE                    6
```

-continued

```
                          note = D-amino acid
SITE                      7
                          note = D-amino acid
SITE                      8
                          note = D-amino acid
SITE                      9
                          note = D-amino acid
SITE                      11
                          note = D-amino acid
SITE                      12
                          note = D-amino acid
SITE                      13
                          note = D-amino acid
SITE                      14
                          note = D-amino acid
SITE                      15
                          note = D-amino acid
SITE                      16
                          note = D-amino acid
SITE                      17
                          note = D-amino acid
SITE                      18
                          note = D-amino acid
SITE                      19
                          note = D-amino acid
SITE                      20
                          note = Amidated D-amino acid
SEQUENCE: 162
LXRSVRLRVG LRKRRRRRRR                                                    20

SEQ ID NO: 163            moltype = AA  length = 13
FEATURE                   Location/Qualifiers
source                    1..13
                          mol_type = protein
                          organism = synthetic construct
SITE                      1
                          note = D-amino acid
SITE                      2
                          note = D-Norleucine
SITE                      3
                          note = D-amino acid
SITE                      5
                          note = D-amino acid
SITE                      6
                          note = D-amino acid
SITE                      7
                          note = D-amino acid
SITE                      8
                          note = D-amino acid
SITE                      9
                          note = D-amino acid
SITE                      11
                          note = D-amino acid
SITE                      12
                          note = D-amino acid
SITE                      13
                          note = D-amino acid
SEQUENCE: 163
LXRGVRLRVG LRK                                                           13

SEQ ID NO: 164            moltype = AA  length = 20
FEATURE                   Location/Qualifiers
source                    1..20
                          mol_type = protein
                          organism = synthetic construct
SITE                      1
                          note = D-amino acid
SITE                      2
                          note = D-Norleucine
SITE                      3
                          note = D-amino acid
SITE                      5
                          note = D-amino acid
SITE                      6
                          note = D-amino acid
SITE                      7
                          note = D-amino acid
SITE                      8
                          note = D-amino acid
```

```
SITE                 9
                     note = D-amino acid
SITE                 11
                     note = D-amino acid
SITE                 12
                     note = D-amino acid
SITE                 13
                     note = D-amino acid
SITE                 14
                     note = D-amino acid
SITE                 15
                     note = D-amino acid
SITE                 16
                     note = D-amino acid
SITE                 17
                     note = D-amino acid
SITE                 18
                     note = D-amino acid
SITE                 19
                     note = D-amino acid
SITE                 20
                     note = Amidated D-amino acid
SEQUENCE: 164
LXRGVRLRVG LRKRRRRRRR                                             20

SEQ ID NO: 165       moltype = AA  length = 19
FEATURE              Location/Qualifiers
source               1..19
                     mol_type = protein
                     organism = synthetic construct
SITE                 1
                     note = D-amino acid
SITE                 2
                     note = D-Norleucine
SITE                 3
                     note = D-amino acid
SITE                 5
                     note = D-amino acid
SITE                 6
                     note = D-amino acid
SITE                 7
                     note = D-amino acid
SITE                 8
                     note = D-amino acid
SITE                 9
                     note = D-amino acid
SITE                 11
                     note = D-amino acid
SITE                 12
                     note = D-amino acid
SITE                 13
                     note = D-amino acid
SITE                 14
                     note = D-amino acid
SITE                 15
                     note = D-amino acid
SITE                 16
                     note = D-amino acid
SITE                 17
                     note = D-amino acid
SITE                 19
                     note = Amidated D-amino acid
SEQUENCE: 165
LXRGVRLRVG LRKRRRRGY                                              19

SEQ ID NO: 166       moltype = AA  length = 20
FEATURE              Location/Qualifiers
source               1..20
                     mol_type = protein
                     organism = synthetic construct
SITE                 1
                     note = D-amino acid
SITE                 2
                     note = D-Norleucine
SITE                 3
                     note = D-amino acid
SITE                 5
                     note = D-amino acid
SITE                 6
```

-continued

```
                             note = D-amino acid
SITE                         7
                             note = D-amino acid
SITE                         8
                             note = D-amino acid
SITE                         9
                             note = D-amino acid
SITE                         11
                             note = D-amino acid
SITE                         12
                             note = D-amino acid
SITE                         13
                             note = D-amino acid
SITE                         14
                             note = D-amino acid
SITE                         15
                             note = D-amino acid
SITE                         16
                             note = D-amino acid
SITE                         17
                             note = D-amino acid
SITE                         18
                             note = D-amino acid
SITE                         20
                             note = Amidated L-2-naphthylalanine
SEQUENCE: 166
LXRGVRLRVG LRKRRRRRGX                                                          20

SEQ ID NO: 167               moltype = AA  length = 21
FEATURE                      Location/Qualifiers
source                       1..21
                             mol_type = protein
                             organism = synthetic construct
SITE                         1
                             note = D-amino acid
SITE                         2
                             note = D-amino acid
SITE                         3
                             note = D-amino acid
SITE                         4
                             note = D-amino acid
SITE                         5
                             note = D-amino acid
SITE                         6
                             note = D-amino acid
SITE                         7
                             note = D-amino acid
SITE                         8
                             note = D-amino acid
SITE                         9
                             note = D-amino acid
SITE                         11
                             note = D-amino acid
SITE                         12
                             note = D-amino acid
SITE                         13
                             note = D-amino acid
SITE                         14
                             note = D-amino acid
SITE                         15
                             note = D-amino acid
SITE                         16
                             note = D-amino acid
SITE                         17
                             note = D-amino acid
SITE                         18
                             note = D-amino acid
SITE                         19
                             note = D-amino acid
SITE                         20
                             note = D-amino acid
SITE                         21
                             note = C6 linker attached to 5-Carboxyfluorescein modified
                              amidated D-amino acid
SEQUENCE: 167
LMRSVRLRVG LRKRRRRRRR K                                                        21

SEQ ID NO: 168               moltype = AA  length = 20
FEATURE                      Location/Qualifiers
```

```
source                  1..20
                        mol_type = protein
                        organism = synthetic construct
SITE                    1
                        note = D-amino acid
SITE                    2
                        note = D-Norleucine
SITE                    3
                        note = D-amino acid
SITE                    4
                        note = D-amino acid
SITE                    5
                        note = D-amino acid
SITE                    6
                        note = D-amino acid
SITE                    7
                        note = D-amino acid
SITE                    8
                        note = D-amino acid
SITE                    9
                        note = D-amino acid
SITE                    11
                        note = D-amino acid
SITE                    12
                        note = D-amino acid
SITE                    13
                        note = D-amino acid
SITE                    14
                        note = D-amino acid
SITE                    15
                        note = D-amino acid
SITE                    16
                        note = D-amino acid
SITE                    17
                        note = D-amino acid
SITE                    18
                        note = D-amino acid
SITE                    20
                        note = Amidated L-2-naphthylalanine
SEQUENCE: 168
LXRSRRLRVG LRKRRRRRGX                                                    20

SEQ ID NO: 169          moltype = AA  length = 13
FEATURE                 Location/Qualifiers
source                  1..13
                        mol_type = protein
                        organism = synthetic construct
SITE                    1
                        note = D-amino acid
SITE                    2
                        note = D-Norleucine
SITE                    3
                        note = D-amino acid
SITE                    4
                        note = alpha-aminobutyric acid
SITE                    5
                        note = D-amino acid
SITE                    6
                        note = D-amino acid
SITE                    7
                        note = D-amino acid
SITE                    8
                        note = D-amino acid
SITE                    9
                        note = D-amino acid
SITE                    11
                        note = D-amino acid
SITE                    12
                        note = D-amino acid
SITE                    13
                        note = D-amino acid
SEQUENCE: 169
LXRXVRLRVG LRK                                                           13

SEQ ID NO: 170          moltype = AA  length = 20
FEATURE                 Location/Qualifiers
source                  1..20
                        mol_type = protein
                        organism = synthetic construct
```

-continued

```
SITE                  1
                      note = D-amino acid
SITE                  2
                      note = D-Norleucine
SITE                  3
                      note = D-amino acid
SITE                  4
                      note = alpha-aminobutyric acid
SITE                  5
                      note = D-amino acid
SITE                  6
                      note = D-amino acid
SITE                  7
                      note = D-amino acid
SITE                  8
                      note = D-amino acid
SITE                  9
                      note = D-amino acid
SITE                  11
                      note = D-amino acid
SITE                  12
                      note = D-amino acid
SITE                  13
                      note = D-amino acid
SITE                  14
                      note = D-amino acid
SITE                  15
                      note = D-amino acid
SITE                  16
                      note = D-amino acid
SITE                  17
                      note = D-amino acid
SITE                  18
                      note = D-amino acid
SITE                  20
                      note = Amidated L-2-naphthylalanine
SEQUENCE: 170
LXRXVRLRVG LRKRRRRRGX                                                          20

SEQ ID NO: 171        moltype = AA  length = 13
FEATURE               Location/Qualifiers
source                1..13
                      mol_type = protein
                      organism = synthetic construct
SITE                  1
                      note = D-amino acid
SITE                  2
                      note = D-Norleucine
SITE                  3
                      note = D-amino acid
SITE                  4
                      note = D-amino acid
SITE                  5
                      note = D-amino acid
SITE                  6
                      note = D-amino acid
SITE                  7
                      note = D-amino acid
SITE                  8
                      note = D-amino acid
SITE                  9
                      note = D-Norleucine
SITE                  11
                      note = D-amino acid
SITE                  12
                      note = D-amino acid
SITE                  13
                      note = D-amino acid
SEQUENCE: 171
LXRSVRLRXG LRK                                                                 13

SEQ ID NO: 172        moltype = AA  length = 20
FEATURE               Location/Qualifiers
source                1..20
                      mol_type = protein
                      organism = synthetic construct
SITE                  1
                      note = D-amino acid
SITE                  2
```

-continued

```
                         note = D-Norleucine
SITE                     3
                         note = D-amino acid
SITE                     4
                         note = D-amino acid
SITE                     5
                         note = D-amino acid
SITE                     6
                         note = D-amino acid
SITE                     7
                         note = D-amino acid
SITE                     8
                         note = D-amino acid
SITE                     9
                         note = D-Norleucine
SITE                     11
                         note = D-amino acid
SITE                     12
                         note = D-amino acid
SITE                     13
                         note = D-amino acid
SITE                     14
                         note = D-amino acid
SITE                     15
                         note = D-amino acid
SITE                     16
                         note = D-amino acid
SITE                     17
                         note = D-amino acid
SITE                     18
                         note = D-amino acid
SITE                     20
                         note = Amidated L-2-naphthylalanine
SEQUENCE: 172
LXRSVRLRXG LRKRRRRRGX                                                      20

SEQ ID NO: 173           moltype = AA  length = 13
FEATURE                  Location/Qualifiers
source                   1..13
                         mol_type = protein
                         organism = synthetic construct
SITE                     1
                         note = D-amino acid
SITE                     2
                         note = D-Norleucine
SITE                     3
                         note = D-amino acid
SITE                     4
                         note = D-amino acid
SITE                     5
                         note = D-amino acid
SITE                     6
                         note = D-amino acid
SITE                     7
                         note = D-amino acid
SITE                     8
                         note = D-amino acid
SITE                     9
                         note = D-amino acid
SITE                     10
                         note = Beta-alanine
SITE                     11
                         note = D-amino acid
SITE                     12
                         note = D-amino acid
SITE                     13
                         note = D-amino acid
SEQUENCE: 173
LXRSVRLRVX LRK                                                             13

SEQ ID NO: 174           moltype = AA  length = 20
FEATURE                  Location/Qualifiers
source                   1..20
                         mol_type = protein
                         organism = synthetic construct
SITE                     1
                         note = D-amino acid
SITE                     2
                         note = D-Norleucine
```

-continued

```
SITE                     3
                         note = D-amino acid
SITE                     4
                         note = D-amino acid
SITE                     5
                         note = D-amino acid
SITE                     6
                         note = D-amino acid
SITE                     7
                         note = D-amino acid
SITE                     8
                         note = D-amino acid
SITE                     9
                         note = D-amino acid
SITE                     10
                         note = Beta-alanine
SITE                     11
                         note = D-amino acid
SITE                     12
                         note = D-amino acid
SITE                     13
                         note = D-amino acid
SITE                     14
                         note = D-amino acid
SITE                     15
                         note = D-amino acid
SITE                     16
                         note = D-amino acid
SITE                     17
                         note = D-amino acid
SITE                     18
                         note = D-amino acid
SITE                     20
                         note = Amidated L-2-naphthylalanine
SEQUENCE: 174
LXRSVRLRVX LRKRRRRRGX                                              20

SEQ ID NO: 175           moltype = AA  length = 14
FEATURE                  Location/Qualifiers
source                   1..14
                         mol_type = protein
                         organism = synthetic construct
SITE                     1
                         note = 5-(dimethylamino)naphthalene-1-sulfonyl chloride
                          modified sarcosine
SITE                     2
                         note = D-amino acid
SITE                     3
                         note = D-Norleucine
SITE                     4
                         note = D-amino acid
SITE                     5
                         note = D-amino acid
SITE                     6
                         note = D-amino acid
SITE                     7
                         note = D-amino acid
SITE                     8
                         note = D-amino acid
SITE                     9
                         note = D-amino acid
SITE                     10
                         note = D-amino acid
SITE                     12
                         note = D-amino acid
SITE                     13
                         note = D-amino acid
SITE                     14
                         note = D-amino acid
SEQUENCE: 175
XLXRSVRLRV GLRK                                                    14

SEQ ID NO: 176           moltype = AA  length = 14
FEATURE                  Location/Qualifiers
source                   1..14
                         mol_type = protein
                         organism = synthetic construct
SITE                     1
                         note = 5-(dimethylamino)naphthalene-1-sulfonyl chloride
```

-continued

```
                          modified sarcosine
SITE                      2
                          note = D-amino acid
SITE                      3
                          note = D-Norleucine
SITE                      4
                          note = D-amino acid
SITE                      5
                          note = D-amino acid
SITE                      6
                          note = D-amino acid
SITE                      7
                          note = D-amino acid
SITE                      8
                          note = D-amino acid
SITE                      9
                          note = D-amino acid
SITE                      10
                          note = D-amino acid
SITE                      12
                          note = D-amino acid
SITE                      13
                          note = D-amino acid
SITE                      14
                          note = D-amino acid
SEQUENCE: 176
XLXRSVRLRV GLRR                                                     14

SEQ ID NO: 177            moltype = AA  length = 20
FEATURE                   Location/Qualifiers
source                    1..20
                          mol_type = protein
                          organism = synthetic construct
SITE                      1
                          note = 5-(dimethylamino)naphthalene-1-sulfonyl chloride
                           modified sarcosine
SITE                      2
                          note = D-amino acid
SITE                      3
                          note = D-Norleucine
SITE                      4
                          note = D-amino acid
SITE                      5
                          note = D-amino acid
SITE                      6
                          note = D-amino acid
SITE                      7
                          note = D-amino acid
SITE                      8
                          note = D-amino acid
SITE                      9
                          note = D-amino acid
SITE                      10
                          note = D-amino acid
SITE                      12
                          note = D-amino acid
SITE                      13
                          note = D-amino acid
SITE                      14
                          note = D-amino acid
SITE                      15
                          note = D-amino acid
SITE                      16
                          note = D-amino acid
SITE                      17
                          note = D-amino acid
SITE                      18
                          note = D-amino acid
SITE                      19
                          note = Sarcosine
SITE                      20
                          note = Methoxy sarcosine
SEQUENCE: 177
XLXRSVRLRV GLRRRRRRXX                                               20

SEQ ID NO: 178            moltype = AA  length = 13
FEATURE                   Location/Qualifiers
source                    1..13
                          mol_type = protein
```

-continued

```
                      organism = synthetic construct
SITE                  1
                      note = D-amino acid
SITE                  2
                      note = D-Norleucine
SITE                  3
                      note = D-amino acid
SITE                  4
                      note = D-amino acid
SITE                  5
                      note = D-amino acid
SITE                  6
                      note = D-amino acid
SITE                  7
                      note = D-amino acid
SITE                  8
                      note = D-amino acid
SITE                  9
                      note = D-amino acid
SITE                  11
                      note = D-amino acid
SITE                  12
                      note = D-amino acid
SITE                  13
                      note = D-amino acid
SEQUENCE: 178
LXRSVRLRVG LRR                                                        13

SEQ ID NO: 179        moltype = AA  length = 19
FEATURE               Location/Qualifiers
source                1..19
                      mol_type = protein
                      organism = synthetic construct
SITE                  1
                      note = D-amino acid
SITE                  2
                      note = D-Norleucine
SITE                  3
                      note = D-amino acid
SITE                  4
                      note = D-amino acid
SITE                  5
                      note = D-amino acid
SITE                  6
                      note = D-amino acid
SITE                  7
                      note = D-amino acid
SITE                  8
                      note = D-amino acid
SITE                  9
                      note = D-amino acid
SITE                  11
                      note = D-amino acid
SITE                  12
                      note = D-amino acid
SITE                  13
                      note = D-amino acid
SITE                  14
                      note = D-amino acid
SITE                  15
                      note = D-amino acid
SITE                  16
                      note = D-amino acid
SITE                  17
                      note = D-amino acid
SITE                  18
                      note = Sarcosine
SITE                  19
                      note = Methoxy sarcosine
SEQUENCE: 179
LXRSVRLRVG LRRRRRRXX                                                  19

SEQ ID NO: 180        moltype = AA  length = 13
FEATURE               Location/Qualifiers
source                1..13
                      mol_type = protein
                      organism = synthetic construct
SITE                  1
                      note = D-amino acid
```

-continued

```
SITE                    2
                        note = D-Norleucine
SITE                    3
                        note = D-amino acid
SITE                    4
                        note = Beta-alanine
SITE                    5
                        note = D-amino acid
SITE                    6
                        note = D-amino acid
SITE                    7
                        note = D-amino acid
SITE                    8
                        note = D-amino acid
SITE                    9
                        note = D-amino acid
SITE                    10
                        note = Beta-alanine
SITE                    11
                        note = D-amino acid
SITE                    12
                        note = D-amino acid
SITE                    13
                        note = D-amino acid
SEQUENCE: 180
LXRXVRLRVX LRK                                                       13

SEQ ID NO: 181          moltype = AA  length = 20
FEATURE                 Location/Qualifiers
source                  1..20
                        mol_type = protein
                        organism = synthetic construct
SITE                    1
                        note = D-amino acid
SITE                    2
                        note = D-Norleucine
SITE                    3
                        note = D-amino acid
SITE                    4
                        note = Beta-alanine
SITE                    5
                        note = D-amino acid
SITE                    6
                        note = D-amino acid
SITE                    7
                        note = D-amino acid
SITE                    8
                        note = D-amino acid
SITE                    9
                        note = D-amino acid
SITE                    10
                        note = Beta-alanine
SITE                    11
                        note = D-amino acid
SITE                    12
                        note = D-amino acid
SITE                    13
                        note = D-amino acid
SITE                    14
                        note = D-amino acid
SITE                    15
                        note = D-amino acid
SITE                    16
                        note = D-amino acid
SITE                    17
                        note = D-amino acid
SITE                    18
                        note = D-amino acid
SITE                    20
                        note = Amidated L-2-naphthylalanine
SEQUENCE: 181
LXRXVRLRVX LRKRRRRRGX                                                20

SEQ ID NO: 182          moltype = AA  length = 13
FEATURE                 Location/Qualifiers
source                  1..13
                        mol_type = protein
                        organism = synthetic construct
SITE                    1
```

-continued

```
                          note = D-amino acid
SITE                      2
                          note = D-Norleucine
SITE                      3
                          note = D-amino acid
SITE                      4
                          note = D-amino acid
SITE                      5
                          note = D-amino acid
SITE                      6
                          note = D-amino acid
SITE                      7
                          note = D-amino acid
SITE                      8
                          note = D-amino acid
SITE                      9
                          note = D-amino acid
SITE                      10
                          note = Beta-alanine
SITE                      11
                          note = D-amino acid
SITE                      12
                          note = D-amino acid
SITE                      13
                          note = 6-aminohexanoic acid
SEQUENCE: 182
LXRAVRLRVX LRX                                                          13

SEQ ID NO: 183            moltype = AA   length = 22
FEATURE                   Location/Qualifiers
source                    1..22
                          mol_type = protein
                          organism = synthetic construct
SITE                      1
                          note = D-amino acid
SITE                      2
                          note = D-Norleucine
SITE                      3
                          note = D-amino acid
SITE                      4
                          note = D-amino acid
SITE                      5
                          note = D-amino acid
SITE                      6
                          note = D-amino acid
SITE                      7
                          note = D-amino acid
SITE                      8
                          note = D-amino acid
SITE                      9
                          note = D-amino acid
SITE                      10
                          note = Beta-alanine
SITE                      11
                          note = D-amino acid
SITE                      12
                          note = D-amino acid
SITE                      13
                          note = 6-aminohexanoic acid
SITE                      14
                          note = D-amino acid
SITE                      15
                          note = 6-aminohexanoic acid
SITE                      16
                          note = D-amino acid
SITE                      17
                          note = 6-aminohexanoic acid
SITE                      18
                          note = D-amino acid
SITE                      19
                          note = 6-aminohexanoic acid
SITE                      20
                          note = D-amino acid
SITE                      21
                          note = 6-aminohexanoic acid
SITE                      22
                          note = Amidated D-amino acid
SEQUENCE: 183
LXRAVRLRVX LRXRXRXRXR XR                                                22
```

```
SEQ ID NO: 184          moltype = AA  length = 24
FEATURE                 Location/Qualifiers
source                  1..24
                        mol_type = protein
                        organism = synthetic construct
SITE                    1
                        note = D-amino acid
SITE                    2
                        note = D-Norleucine
SITE                    3
                        note = D-amino acid
SITE                    4
                        note = D-amino acid
SITE                    5
                        note = D-amino acid
SITE                    6
                        note = D-amino acid
SITE                    7
                        note = D-amino acid
SITE                    8
                        note = D-amino acid
SITE                    9
                        note = D-amino acid
SITE                    10
                        note = Beta-alanine
SITE                    11
                        note = D-amino acid
SITE                    12
                        note = D-amino acid
SITE                    13
                        note = 6-aminohexanoic acid
SITE                    14
                        note = D-amino acid
SITE                    15
                        note = 6-aminohexanoic acid
SITE                    16
                        note = D-amino acid
SITE                    17
                        note = 6-aminohexanoic acid
SITE                    18
                        note = D-amino acid
SITE                    19
                        note = 6-aminohexanoic acid
SITE                    20
                        note = D-amino acid
SITE                    21
                        note = 6-aminohexanoic acid
SITE                    22
                        note = D-amino acid
SITE                    23
                        note = 6-aminohexanoic acid
SITE                    24
                        note = Amidated D-amino acid
SEQUENCE: 184
LXRAVRLRVX LRXRXRXRXR XRXY                                        24

SEQ ID NO: 185          moltype = AA  length = 13
FEATURE                 Location/Qualifiers
source                  1..13
                        mol_type = protein
                        organism = synthetic construct
SITE                    1
                        note = D-amino acid
SITE                    2
                        note = D-Norleucine
SITE                    3
                        note = D-amino acid
SITE                    4
                        note = D-amino acid
SITE                    5
                        note = D-amino acid
SITE                    6
                        note = D-amino acid
SITE                    7
                        note = D-amino acid
SITE                    8
                        note = D-amino acid
SITE                    9
```

-continued

```
                        note = D-amino acid
SITE                    11
                        note = D-amino acid
SITE                    12
                        note = D-amino acid
SITE                    13
                        note = 6-aminohexanoic acid
SEQUENCE: 185
LXRSVRLRVG LRX                                                              13

SEQ ID NO: 186          moltype = AA  length = 22
FEATURE                 Location/Qualifiers
source                  1..22
                        mol_type = protein
                        organism = synthetic construct
SITE                    1
                        note = D-amino acid
SITE                    2
                        note = D-Norleucine
SITE                    3
                        note = D-amino acid
SITE                    4
                        note = D-amino acid
SITE                    5
                        note = D-amino acid
SITE                    6
                        note = D-amino acid
SITE                    7
                        note = D-amino acid
SITE                    8
                        note = D-amino acid
SITE                    9
                        note = D-amino acid
SITE                    11
                        note = D-amino acid
SITE                    12
                        note = D-amino acid
SITE                    13
                        note = 6-aminohexanoic acid
SITE                    14
                        note = D-amino acid
SITE                    15
                        note = 6-aminohexanoic acid
SITE                    16
                        note = D-amino acid
SITE                    17
                        note = 6-aminohexanoic acid
SITE                    18
                        note = D-amino acid
SITE                    19
                        note = 6-aminohexanoic acid
SITE                    20
                        note = D-amino acid
SITE                    21
                        note = 6-aminohexanoic acid
SITE                    22
                        note = Amidated D-amino acid
SEQUENCE: 186
LXRSVRLRVG LRXRXRXRXR XR                                                    22

SEQ ID NO: 187          moltype = AA  length = 26
FEATURE                 Location/Qualifiers
source                  1..26
                        mol_type = protein
                        organism = synthetic construct
SITE                    4
                        note = Epsilon amine of lysine modified with palmitic acid
SITE                    8
                        note = 6-aminohexanoic acid
SITE                    10
                        note = Citrulline
SITE                    11
                        note = 4-acetamidobenzoic acid
SITE                    13
                        note = Beta-alanine
SITE                    14
                        note = D-amino acid
SITE                    15
                        note = D-Norleucine
```

-continued

```
SITE                 16
                     note = D-amino acid
SITE                 17
                     note = D-amino acid
SITE                 18
                     note = D-amino acid
SITE                 19
                     note = D-amino acid
SITE                 20
                     note = D-amino acid
SITE                 21
                     note = D-amino acid
SITE                 22
                     note = D-amino acid
SITE                 23
                     note = Beta-alanine
SITE                 24
                     note = D-amino acid
SITE                 25
                     note = D-amino acid
SITE                 26
                     note = D-amino acid
SEQUENCE: 187
EYEKEYEXVX XGXLXRSVRL RVXLRK                                            26

SEQ ID NO: 188       moltype = AA  length = 33
FEATURE              Location/Qualifiers
source               1..33
                     mol_type = protein
                     organism = synthetic construct
SITE                 4
                     note = Epsilon amine of lysine modified with palmitic acid
SITE                 8
                     note = 6-aminohexanoic acid
SITE                 10
                     note = Citrulline
SITE                 11
                     note = 4-acetamidobenzoic acid
SITE                 13
                     note = Beta-alanine
SITE                 14
                     note = D-amino acid
SITE                 15
                     note = D-Norleucine
SITE                 16
                     note = D-amino acid
SITE                 17
                     note = D-amino acid
SITE                 18
                     note = D-amino acid
SITE                 19
                     note = D-amino acid
SITE                 20
                     note = D-amino acid
SITE                 21
                     note = D-amino acid
SITE                 22
                     note = D-amino acid
SITE                 23
                     note = Beta-alanine
SITE                 24
                     note = D-amino acid
SITE                 25
                     note = D-amino acid
SITE                 26
                     note = D-amino acid
SITE                 27
                     note = D-amino acid
SITE                 28
                     note = D-amino acid
SITE                 29
                     note = D-amino acid
SITE                 30
                     note = D-amino acid
SITE                 31
                     note = D-amino acid
SITE                 33
                     note = Amidated L-2-naphthylalanine
SEQUENCE: 188
```

-continued

```
EYEKEYEXVX XGXLXRSVRL RVXLRKRRRR RGX                                    33

SEQ ID NO: 189           moltype = AA  length = 28
FEATURE                  Location/Qualifiers
source                   1..28
                         mol_type = protein
                         organism = synthetic construct
SITE                     1
                         note = D-amino acid
SITE                     2
                         note = D-amino acid
SITE                     3
                         note = D-amino acid
SITE                     4
                         note = D-amino acid
SITE                     5
                         note = D-amino acid
SITE                     6
                         note = D-amino acid
SITE                     7
                         note = D-amino acid
SITE                     8
                         note = D-amino acid
SITE                     9
                         note = 6-aminohexanoic acid
SITE                     16
                         note = D-amino acid
SITE                     17
                         note = D-Norleucine
SITE                     18
                         note = D-amino acid
SITE                     19
                         note = Beta-alanine
SITE                     20
                         note = D-amino acid
SITE                     21
                         note = D-amino acid
SITE                     22
                         note = D-amino acid
SITE                     23
                         note = D-amino acid
SITE                     24
                         note = D-amino acid
SITE                     25
                         note = Beta-alanine
SITE                     26
                         note = D-amino acid
SITE                     27
                         note = D-amino acid
SITE                     28
                         note = D-amino acid
SEQUENCE: 189
EEEEEEEEXP LGLAGLXRXV RLRVXLRK                                          28

SEQ ID NO: 190           moltype = AA  length = 12
FEATURE                  Location/Qualifiers
source                   1..12
                         mol_type = protein
                         organism = synthetic construct
SITE                     1
                         note = D-amino acid
SITE                     2
                         note = D-Norleucine
SITE                     3
                         note = D-amino acid
SITE                     4
                         note = Beta-alanine
SITE                     5
                         note = D-amino acid
SITE                     6
                         note = D-amino acid
SITE                     7
                         note = D-amino acid
SITE                     8
                         note = D-amino acid
SITE                     9
                         note = D-amino acid
SITE                     10
                         note = Beta-alanine
```

-continued

```
SITE            11
                note = D-amino acid
SITE            12
                note = D-amino acid
SEQUENCE: 190
LXRXVRLRVX LR                                    12
```